(12) United States Patent
Levy et al.

(10) Patent No.: US 10,722,572 B2
(45) Date of Patent: Jul. 28, 2020

(54) METHODS AND COMPOSITIONS FOR TREATING AND PREVENTING HIV

(71) Applicants: INSERM (Institut National de la Sante et de la Recherche Medicale), Paris (FR); Baylor Research Institute, Dallas, TX (US); Universite Paris Est Creteil Val De Marne, Creteil (FR); Assistance Publique Hopitaux de Paris, Paris (FR)

(72) Inventors: Yves Levy, Paris (FR); Gerard Zurawski, Midlothian, TX (US); Sandra Zurawski, Midlothian, TX (US); Anne-Laure Flamar, New York, NY (US)

(73) Assignees: INSTITUT NATIONAL DE LA SANTE ET DE LA RECHERCHE MEDICALE INSERM, Paris (FR); UNIVERSITE PARIS EST CRETEIL VAL DE MARNE, Creteil (FR); BAYLOR RESEARCH INSTITUTE, Dallas, TX (US); ASSISTANCE PUBLIQUE HOPITAUX DE PARIS, Paris (FR)

( * ) Notice: Subject to any disclaimer, the term of this patent is extended or adjusted under 35 U.S.C. 154(b) by 0 days.

(21) Appl. No.: 16/708,787

(22) Filed: Dec. 10, 2019

(65) Prior Publication Data
US 2020/0101152 A1  Apr. 2, 2020

Related U.S. Application Data

(63) Continuation of application No. 16/141,157, filed on Sep. 25, 2018, now Pat. No. 10,610,585.

(60) Provisional application No. 62/563,158, filed on Sep. 26, 2017.

(51) Int. Cl.
| *C07K 16/28* | (2006.01) |
| *A61K 39/00* | (2006.01) |
| *A61K 39/395* | (2006.01) |
| *A61K 39/12* | (2006.01) |
| *A61K 39/21* | (2006.01) |
| *C07K 14/005* | (2006.01) |
| *C12N 7/00* | (2006.01) |
| *C07K 16/10* | (2006.01) |
| *A61P 31/18* | (2006.01) |

(52) U.S. Cl.
CPC .............. *A61K 39/21* (2013.01); *A61K 39/12* (2013.01); *A61P 31/18* (2018.01); *C07K 14/005* (2013.01); *C07K 16/1063* (2013.01); *C07K 16/28* (2013.01); *C07K 16/2878* (2013.01); *C12N 7/00* (2013.01); *A61K 2039/505* (2013.01); *A61K 2039/572* (2013.01); *A61K 2039/575* (2013.01); *A61K 2039/6056* (2013.01); *A61K 2039/627* (2013.01); *C07K 2317/24* (2013.01); *C07K 2317/34* (2013.01); *C07K 2317/732* (2013.01); *C07K 2317/76* (2013.01); *C07K 2319/02* (2013.01); *C07K 2319/40* (2013.01); *C12N 2740/16034* (2013.01); *C12N 2740/16134* (2013.01); *C12N 2740/16171* (2013.01)

(58) Field of Classification Search
CPC ............ A61K 2039/6056; A61K 39/00; C07K 16/2878; C07K 14/005; C07K 2319/00
See application file for complete search history.

(56) References Cited

U.S. PATENT DOCUMENTS

| 4,235,871 A | 11/1980 | Papahadjopoulos et al. |
| 4,501,728 A | 2/1985 | Geho et al. |
| 4,578,770 A | 3/1986 | Mitani |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,837,028 A | 6/1989 | Allen |
| 4,902,505 A | 2/1990 | Pardridge et al. |
| 4,957,735 A | 9/1990 | Huang |
| 5,004,697 A | 4/1991 | Pardridge |
| 5,019,369 A | 5/1991 | Presant et al. |
| 5,055,303 A | 10/1991 | Riley, Jr. |
| 5,188,837 A | 2/1993 | Domb |
| 5,254,342 A | 10/1993 | Shen et al. |
| 5,268,164 A | 12/1993 | Kozarich et al. |
| 5,271,961 A | 12/1993 | Mathiowitz et al. |

(Continued)

FOREIGN PATENT DOCUMENTS

| AU | 2009/270771 | 1/2010 |
| CN | 1307484 | 8/2001 |

(Continued)

OTHER PUBLICATIONS

Attwood, "The Babel of Bioinformatics," *Science* 2000; 290: 471-473.

(Continued)

*Primary Examiner* — Barry A Chestnut
(74) *Attorney, Agent, or Firm* — Norton Rose Fulbright US LLP

(57) ABSTRACT

Methods and compositions are provided that can be used to vaccinate against and treat HIV. Specifically contemplated are vaccine compositions and methods of using these compositions treat HIV in patients. Aspects of the disclosure relate to an anti-CD40 antibody-HIV antigen fusion protein comprising (i) an anti-CD40 heavy chain (HCD40)-HIV antigen (Ag) fusion protein comprising the formula: HCD40-Ag, wherein Ag is a polypeptide with at least 80% sequence identity to SEQ ID NO:1; and (ii) an anti-CD40 light chain (LCD40).

29 Claims, 17 Drawing Sheets
Specification includes a Sequence Listing.

(56) References Cited

U.S. PATENT DOCUMENTS

| | | |
|---|---|---|
| 5,413,797 A | 5/1995 | Khan et al. |
| 5,506,206 A | 4/1996 | Kozarich et al. |
| 5,514,670 A | 5/1996 | Friedman et al. |
| 5,534,496 A | 7/1996 | Lee et al. |
| 5,545,806 A | 8/1996 | Lonberg et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,770,429 A | 6/1998 | Lonberg et al. |
| 5,871,746 A | 2/1999 | Boutillon et al. |
| 6,140,059 A | 10/2000 | Shawaller |
| 6,469,143 B2 | 10/2002 | Sallberg |
| 6,541,011 B2 | 4/2003 | Punnonen et al. |
| 6,573,245 B1 | 6/2003 | Marciani |
| 7,060,495 B2 | 6/2006 | Gehrmann et al. |
| 7,067,110 B1 | 6/2006 | Gillies et al. |
| 7,118,751 B1 | 10/2006 | Ledbetter et al. |
| 7,122,187 B2 | 10/2006 | Black et al. |
| 7,261,897 B2 | 8/2007 | Skeiky et al. |
| 7,288,251 B2 | 10/2007 | Bedian et al. |
| 7,456,260 B2 | 11/2008 | Rybak et al. |
| 7,476,386 B1 | 1/2009 | Gras-Masse et al. |
| 7,560,534 B2 | 7/2009 | Deo et al. |
| 8,518,410 B2 | 8/2013 | Zurawski et al. |
| 8,961,991 B2 | 2/2015 | Zurawski et al. |
| 9,102,734 B2 | 8/2015 | Zurawski et al. |
| 9,109,011 B2 | 8/2015 | Banchereau et al. |
| 9,562,104 B2 | 2/2017 | Banchereau et al. |
| 2002/0025513 A1 | 2/2002 | Sallberg |
| 2004/0001853 A1 | 1/2004 | George et al. |
| 2004/0110226 A1 | 6/2004 | Lazar et al. |
| 2004/0120948 A1 | 6/2004 | Mikayama et al. |
| 2004/0146948 A1 | 7/2004 | Britton et al. |
| 2005/0013828 A1 | 1/2005 | George et al. |
| 2005/0221295 A1 | 10/2005 | Hu |
| 2006/0165690 A1 | 7/2006 | Heath et al. |
| 2006/0246089 A1 | 11/2006 | Wu et al. |
| 2007/0025982 A1 | 2/2007 | Ledbetter et al. |
| 2007/0148163 A1 | 6/2007 | Takahashi et al. |
| 2008/0181915 A1 | 7/2008 | Tripp et al. |
| 2008/0199471 A1 | 8/2008 | Bernett et al. |
| 2008/0226667 A1 | 9/2008 | Medzhitov |
| 2008/0233083 A1 | 9/2008 | Ansari et al. |
| 2008/0241139 A1 | 10/2008 | Delucia |
| 2008/0241170 A1 | 10/2008 | Zurawski et al. |
| 2008/0254026 A1 | 10/2008 | Long et al. |
| 2009/0004194 A1 | 1/2009 | Kedl |
| 2009/0068214 A1 | 3/2009 | Qian et al. |
| 2009/0238822 A1 | 9/2009 | George et al. |
| 2009/0324491 A1 | 12/2009 | Aburatani et al. |
| 2009/0324538 A1 | 12/2009 | Wong et al. |
| 2010/0135994 A1 | 6/2010 | Banchereau et al. |
| 2010/0239575 A1 | 9/2010 | Banchereau et al. |
| 2010/0291082 A1 | 11/2010 | Zurawski et al. |
| 2010/0297114 A1 | 11/2010 | Zurawski et al. |
| 2010/0322929 A1 | 12/2010 | Zurawski et al. |
| 2012/0244155 A1 | 9/2012 | Lecine et al. |

FOREIGN PATENT DOCUMENTS

| | | |
|---|---|---|
| CN | 1582165 | 2/2005 |
| CN | 1198647 | 4/2005 |
| EP | 0491628 | 6/1992 |
| EP | 023209400 | 8/1994 |
| EP | 0438474 | 5/1996 |
| EP | 0463151 | 6/1996 |
| EP | 0546073 | 9/1997 |
| EP | 1391464 | 2/2004 |
| GB | 2405873 | 3/2005 |
| JP | H10/504458 | 5/1998 |
| JP | 2004/192125 | 7/2004 |
| JP | 2005/527513 | 9/2005 |
| JP | 2006/501131 | 1/2006 |
| JP | 2006/342173 | 12/2006 |
| JP | 2007/026135 | 2/2007 |
| JP | 2009/022289 | 2/2009 |
| JP | 2009/259188 | 11/2009 |
| JP | 2012/520074 | 9/2012 |
| JP | 2015/028021 | 2/2015 |
| WO | WO 88/01649 | 3/1988 |
| WO | WO 90/07861 | 7/1990 |
| WO | WO 99/22008 | 5/1999 |
| WO | WO 99/27954 | 6/1999 |
| WO | WO 00/000156 | 1/2000 |
| WO | WO 2000/075348 | 12/2000 |
| WO | WO 2001/032714 | 5/2001 |
| WO | WO 2001/083755 | 11/2001 |
| WO | WO 2001/085798 | 11/2001 |
| WO | WO 2002/028905 | 4/2002 |
| WO | WO 2003/024480 | 3/2003 |
| WO | WO 2003/029296 | 4/2003 |
| WO | WO 2003/040169 | 5/2003 |
| WO | WO 2004/035619 | 4/2004 |
| WO | WO 2004/069873 | 8/2004 |
| WO | WO 2006/128103 | 11/2006 |
| WO | WO 2007/041861 | 4/2007 |
| WO | WO 2007/051169 | 5/2007 |
| WO | WO 2007/130493 | 11/2007 |
| WO | WO 2008/047723 | 4/2008 |
| WO | WO 2008/097817 | 8/2008 |
| WO | WO 2008/097870 | 8/2008 |
| WO | WO 2010/009346 | 1/2010 |
| WO | WO 2010/104747 | 9/2010 |
| WO | WO 2010/104748 | 9/2010 |
| WO | WO 2010/104749 | 9/2010 |
| WO | WO 2010/104761 | 9/2010 |
| WO | WO 2011/023785 | 3/2011 |
| WO | WO 2011/032161 | 3/2011 |
| WO | WO 2011/140255 | 11/2011 |

OTHER PUBLICATIONS

Austyn, Jonathan M., et al., "Migration Patterns of Dendritic Cells in the Mouse," J. Exp. Med., Feb. 1988, vol. 167, pp. 646-651.
Banchereau, Jacques, et al., "Immunobiology of Dendritic Cells," Annu. Rev. Immunol., (2000), 18:767-811.
Bates, et al., "APCs Express DCIR, a Novel C-Type Lectin Surface Receptor Containing an Immunoreceptor Tyrosine-Based Inhibitory Motif," J. Immunol. (1999) 163:1973-1983.
Beauchamp, Charles 0., et al., "A New Procedure for the Synthesis of Polyethylene Glycol-Protein Adducts; Effects on Function, Receptor Recognition, and Clearance of Superoxide Dismutase, Lactoferrin, and a2-Macroglobulin," Analytical Biochemistry 131 (1983), pp. 25-33.
Benton, Trish, et al., "The Use of UCOE Vectors in Combination with a Preadapted Serum Free, Suspension Cell Line Allows for Rapid Production of Large Quantities of Protein," Cytotechnology, (2002), 38:43-46.
Bonifaz, et al. "Efficient Targeting of Protein Antigen to the Dendritic Cell Receptor DEC-205 in the Stead State Leads to Antigen Presentation on major Histocompatibility Complex Class I Products and Peripheral CD8+ T Cell Tolerance." The Journal of Experimental Medicine. vol. 196(12) pp. 1627-1638, 2002.
Carlring, Jennifer, et al. "CD40 antibody as an adjuvant induces enhanced T cell responses." Vaccine, vol. 22, pp. 3323-3328; Mar. 28, 2004.
Chen et al., "A novel vaccine for mantle cell lymphoma based on targeting cyclin D1 to dendritic cells via CD40" *J. Hematol Oncol.*, 2015, 8:35.
Chen et al., "Enhancement and Destruction of Antibody Function by Somatic Mutation: Unequal Occurrence is Controlled by V Gene Combinatorial Associations," EMBO J., 14: 2784-2794, 1995.
Colman, "The Effects of Amino Acid Sequence Changes on Antibody-Antigen Interactions," *Research in Immunology* 145: 33-36, 1994.
Connick et al., "CTL fail to accumulate at sites of HIV-1 replication in lymphoid tissue" Journal of Immunology, 2007; 178: 3978-683.
Cruz H J, et al., "Process development of a recombinant antibody/interleukin-2 fusion protein expressed in protein-free medium by

(56) References Cited

OTHER PUBLICATIONS

BHK cells," Journal of Biotechnology, Elsevier Science Publishers, Amsterdam, NL, vol. 96, No. 2, Jun. 26, 2002.

Dakappagari, et al., "Internalizing antibodies to the C-Type lectins, L-SIGN and DC-SIGN, inhibit viral glycoprotein binding and deliver antigen to human dendritic cells for the induction of T Cell responses," The Journal of Immunology (2006) 176:426-440.

Diehl, et al. "CD40 activation in vivo overcomes peptide-induced peripheral cytotoxic T-lymphocyte tolerance and augments anti-tumor vaccine efficacy." Nature Medicine. vol. 5, No. 7 (Jul. 1999).

Durier et al., "Clinical safety of HIV lipopeptides used as vaccines in healthy volunteers and HIV-infected adults," Aids, 20(7):1039-49, (2006).

Dye, Christopher, et al., "Global Burden of Tuberculosis—Estimated Incidence, Prevalence, and Mortality by Country," JAMA, (1999), 282:677-686.

Extended European Search Report issued in Application No. 171537863, dated Jul. 26, 2017.

Finn, 0., "Cancer Vaccines: Between the Idea and the Reality," Nature Reviews Immunology, (Aug. 2003), 3:630-641.

Flamar et al., "Noncovalent assembly of anti-dendritic cell antibodies and antigens for evoking immune responses in vitro and in vivo." J. Immunol., 2012, 189:2645-2655.

Flamar et al., "Targeting concatenated HIV antigens to human CD40 expands a broad repertoire of multifunctional CD4+ and CD8+ T cells" AIDS, 2013, 27:2041-2051.

Fredriksen, et al., "DNA Vaccines Increase Immunogenicity of Idiotypic Tumor Antigen by Targeting Novel Fusion Proteins to Antigen-Presenting Cells," Molecular Therapy: The Journal of the American Society of Gene Therapy 13(4); 776-785, 2006.

French, et al. "CD40 antibody evokes a cytotoxic T-cell response that eradicates lymphoma and bypasses T-cell help." Nature Medicine. vol. 5, No. 5 (May 1999).

Gallo, R., "The end or the beginning of the drive to an HIV-preventative vaccine: a view from over 20 years," The Lancet, 2005; 366:1894-1898.

Grossman, Claudius, et al., "Enhancement of the Priming Efficacy of DNA Vaccines Encoding Dendritic Cell-Targeted Antigens by Synergistic Toll-Like Receptor Ligands," BMC Immunology, (2009), 10:43, 10 pages.

Hougardy, Jean-Michel, et al., "Heparin-Binding-Hemagglutinin-Induced IFN-y Release as a Diagnostic Tool for Latent Tuberculosis," PLOS ONE, Oct. 2007, Issue 10, 8 pages.

Ihara, "Human Papillomavirus and Cervical Cancer—From Molecular Biology of HPV to HPV Vaccination," Modern Media 53(5); 115-121,2007.

International Search Report and Written Opinion for PCT/US2010/026375 prepared by Korean Intellectual Property Office, dated Nov. 19, 2010.

International Search Report and Written Opinion for PCT/US2010/026268 prepared by Korean Intellectual Property Office, dated Dec. 31, 2010.

International Search Report and Written Opinion for PCT/US2010/026273 prepared by Korean Intellectual Property Office, dated Jan. 6, 2011.

International Search Report and Written Opinion for PCT/US2010/026275 prepared by Korean Intellectual Property Office, dated Jan. 7, 2011.

International Search Report and Written Opinion Issued for PCT/US2012/029802, dated May 28, 2012.

International Search Report and Written Opinion Issued for PCT/US2012/030593, dated May 28, 2012.

Keler, et al. "Antibody-targeted vaccines." Oncogene. vol. 26(25), pp. 3758-3767, 2007.

Klinguer, et al., "Characterization of a multi-lipopeptides mixture used as an HIV-1 vaccine candidate," Vaccine (2000) 18:259-267.

Kussie et al., "A Single Engineered Amino Acid Substitution Changes Antibody Fine Specificity," J. Immunol. 152:146-152, 1994.

Langer, R., "Polymer-Controlled Drug Delivery Systems," Ace. Chem. Res., (1993), 26:537-542.

Levine, A., "Why do we not yet have a human immunodeficiency virus vaccine?" Journal of Virology, 2008; 82(24): 11998-12000.

Li, Wei, "Synergistic Antibody Induction by Antigen-CD40 Ligand Fusion Protein as Improved Immunogen," Immunology, 115, (Jun. 2005), pp. 215-222.

Lo-Man, et al., "Anti-tumor immunity provided by a synthetic multiple antigenic glycopeptide displaying a Tri-Tn glycotope," The Journal of Immunology (2001) 166:2849-2854.

Mariani et al., "HPV Vaccine: An Overview of Immune Response, Clinical Protection, and New Approaches for the Future," Journal of Translational Medicine 8: 105, pp. 1-8, 2010.

Melero et al., "Immunostimulatory monoclonal antibodies for cancer therapy," Nat. Rev. Cancer, 2007; 7: 95-106.

Office Action issued in corresponding Canadian Patent Application No. 2,754,743, dated Jan. 10, 2018.

Office Action Issued in Corresponding Chinese Application No. 2016100873149, dated Feb. 11, 2019.

Office Action Issued in Corresponding European Application No. 17153786.3, dated Aug. 17, 2018.

Office Action issued in Japanese Application No. 2016-198376, dated Aug. 3, 2017.

Office Action Issued in Japanese Patent Application No. 2017-007783, dated Nov. 20, 2018.

Paquette, et al., "Interferon-alpha Induces Dendritic Cell Differentiation of CML Mononuclear Cells In Vitro and In Vivo," Leukemia (2002) 16, pp. 1484-1489.

Reddy, Manjula P., et al., "Elimination of Fe Receptor-Dependent Effector Functions of a Modified lgG4 Monoclonal Antibody to Human CD4," The Journal of Immunology, (2000), 164; pp. 1925-1933.

Rescigno, Maria, et al., "Bacteria-Induced Nee-Biosynthesis, Stabilization, and Surface Expression of Functional Class I Molecules in Mouse Dendritic Cells," Proc. Nail. Acad. Sci., Apr. 1998, vol. 95, pp. 5229-5234.

Rudikoff et al., "Single Amino Acid Substitution Altering-Binding Specificity," PNAS 79: 1979-1983, 1982.

Schjetne, Karoline W., et al., "Delivery of Antigen to CD40 Induces Protective Immune Responses against Tumors" The Journal of Immunology, Apr. 1, 2007, 178(7), pp. 4169-4176.

Schuurhuis et al., "Immature Dendritic Cells Acquire CD8+ Cytotoxic T Lymphocyte Priming Capacity upon Activation by T Helper Cell-independent of—dependent Stimuli," J. Exp. Med., 2000; 192: 145-150.

Search Report Issued in Corresponding Chinese Application No. 2016100873149, dated Jan. 29, 2019.

Skolnick et al., "From Genes to Protein Structure and Function: Novel Applications of Computational Approaches in the Genomic Era," Trends in Biotech 2000; 18:34-39.

Soares, et al. "Three different vaccines based on the 140-amino acid MUC1 peptide with seven tandemly repealed tumor-specific epitopes elicit distinct immune effector mechanisms in wild-type versus MUC1-Transgenic mice with different potential for tumor rejection." The Journal of Immunology (2001) 166:6555-6563.

Spitler, "Cancer Vaccines: The Interferon Analogy," Cancer Biotherapy 10: 1-3, 1995.

Steinman. Ralph M., "The Dendritic Cell System and its Role in Immunogenicity," Annual Review Immunology, (1991), 9:271-296.

Stork, Roland, et al. "N-Glycosylation as Novel Strategy to Improve Pharmacokinetic Properties of Bispecific Single-chain Diabodies." The Journal of Biological Chemistry, vol. 283, No. 12, pp. 7804-7812; Jan. 22, 2008.

Tacken, et al. "Dendritic-cell immunotherapy: from ex vivo loading to in vivo targeting." Nature Reviews. vol. 7(10) pp. 790-802, 2007.

Trumpfheller, et al. "Intensified and protective CD4+ T cell immunity in mice with anti-dendritic cell HIV gag fusion antibody vaccine." The Journal of Experimental Medicine. vol. 203(3) pp. 607-617, 2006.

Van Vliet, Sandra J., et al., "Dendritic Cells and C-Type Lectin Receptors: Coupling Innate to Adaptive Immune Responses," Immunology and Cell Biology, (2008), 86:580-587.

(56) References Cited

OTHER PUBLICATIONS

Vonderhelde et al., "Agonistic CD40 Antibodies and Cancer Therapy," *Clin Cancer Res.* 2013; 19: 1035-1043.

Walker et al. "Toward an AIDS vaccine" Science, 2008; 320: 760-764.

Wells et al., "Combined Triggering of Dendritic Cell Receptors Results in Synergistic Activation and Potent Cytotoxic Immunity," J. Immunol., 2008; 181: 3422-3431.

Winter, et al. "Antibody-based therapy Humanized Antibodies." Immunology Today. vol. 14, No. 6, 243-246, (1993).

Xiang, Rang, et al., "A Dual-Function DNA Vaccine Encoding Carcinoembryonic Antigen and CD40 Ligand Trimer Induces T Cell-Mediated Protective Immunity Against Colon Cancer in Carcinoembryonic Antigen-Transgenic Mice," The Journal of Immunology, (2001), 167;pp. 4560-4565.

Xiong, Jin-he, et al., "Expression of B-Cell Naturation Antigen mRNA in Peripheral Blood Mononuclear Cells in Patients with Systemic Lupus Erythematosus," Huaxi Yixue, (2010), 1 page (Abstract Only).

Yin et al., "Functional Specialty of CD40 and Dendritic Cell Surface Lectins for Exogenous Antigen Presentation to CD8+ and CD4+ T Cells" *EBioMed.,* 2016, 5:46-58.

Zhang, Lixin, et al., "An Adenoviral Vector Cancer Vaccine that Delivers a Tumor-Associated Antigen/CD40-Ligand Fusion Protein to Dendritic Cells," PNAS, Dec. 9, 2003, vol. 100, No. 25, pp. 15101-15106.

Zurawski et al., "Superiority in Rhesus Macaques of Targeting HIV-1 Env gp140 to CD40 versus LOX-1 in Combination with Replication-Competent NYVAC-KC for Induction of Env-Specific Antibody and T Cell Responses," *Journal of Virology,* 2017, 94(9):e01596-16.

Zurawski et al., "Targeting HIV-1 Env gp140 to LOX-1 Elicits Immune Responses in Rhesus Macaques," *PLoS One,* 2016, 11:e0153484.

FIG. 1A-1B

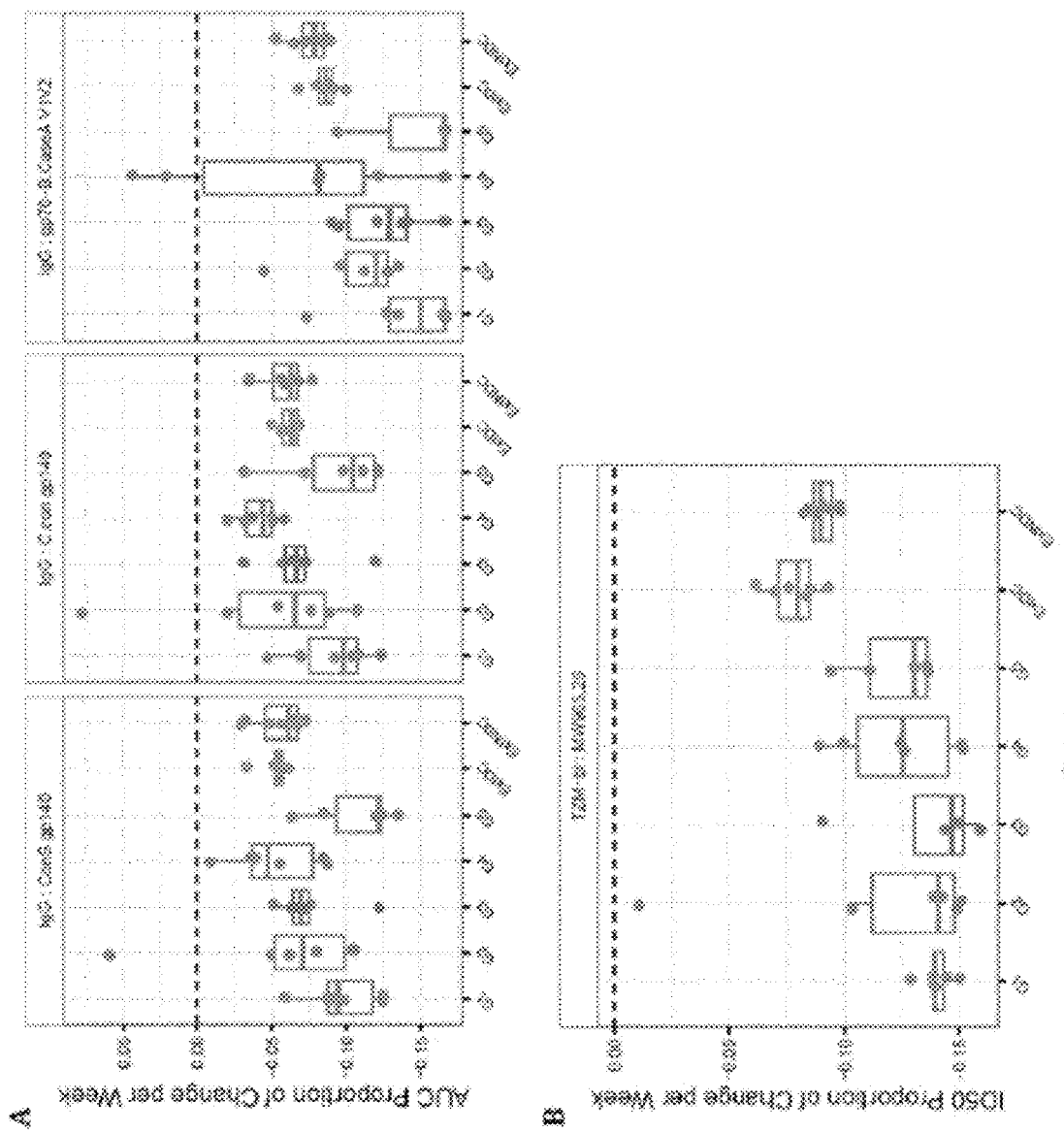
FIG. 11A-B

METHODS AND COMPOSITIONS FOR TREATING AND PREVENTING HIV

CROSS REFERENCE TO RELATED APPLICATIONS

This application is a continuation of U.S. patent application Ser. No. 16/141,157, filed Sep. 25, 2018, which claims the benefit of priority to U.S. Provisional Patent Application Ser. No. 62/563,158, filed Sep. 26, 2017, each of which are hereby incorporated by reference in their entirety.

BACKGROUND

1. Field of the Invention

The present invention relates generally to the field of prophylactic and therapeutic vaccines against an HIV infection. More specifically, the invention relates to a HIV vaccine comprising an anti-DC receptor antibody or a fragment thereof, e.g. anti-CD40 antibody or a fragment thereof, to which at least one HIV antigen is fused or conjugated.

2. Description of Related Art

While treatment for HIV/AIDS has become a reality, in the United States an average of 50,000 new HIV infections are diagnosed each year in the United States and there is an estimated 34 million people living with HIV worldwide.

While a variety of options have been explored, dendritic cells (DCs) are antigen-presenting cells that play a key role in regulating antigen-specific immunity (Mellman and Steinman 2001), (Banchereau, Briere et al. 2000), (Cella, Sallusto et al. 1997). DCs capture antigens, process them into peptides, and present these to T cells. Therefore delivering antigens directly to DC is a focus area for improving vaccines. One such example is the development of DC-based vaccines using ex-vivo antigen-loading of autologous DCs that are then re-administrated to patients (Banchereau, Schuler-Thurner et al. 2001), (Steinman and Dhodapkar 2001).

Another strategy to improve vaccine efficacy is specific targeting to DC of antigen conjugated to antibodies against internalizing DC-specific receptors. While first generation polypeptides have been created, improvements are needed to generate more efficacious therapeutic options. With the continued epidemic of AIDS throughout the world, there is still a need for HIV vaccines and treatment methods.

SUMMARY OF THE INVENTION

Methods and compositions are provided that can be used to vaccinate against and treat HIV. Specifically contemplated are vaccine compositions and methods of using these compositions treat or prevent a subject in need thereof from HIV infection. Aspects of the disclosure relate to an anti-dendritic cell (DC) receptor antibody-HIV antigen fusion protein comprising (i) an anti-DC receptor heavy chain (HDCR)-HIV antigen (Ag) fusion protein comprising the formula: HDCR-Ag, wherein Ag is a polypeptide with at least 80% sequence identity to SEQ ID NO:1; and (ii) an anti-DC receptor light chain (LDCR).

In some embodiments, the anti-DC receptor antibody is selected from the group consisting of anti-DCIR antibody, anti-LOX-1 antibody, anti-langerin antibody and anti-CD40 antibody.

In a specific embodiment, the anti-DC receptor antibody is an anti-CD40 antibody having a heavy chain (HCD40) and a light chain (LCD40).

In some embodiments, the fusion protein further comprises one or more peptide linkers (PL). In some embodiments, the fusion protein comprises: (i) HCD40-PL-Ag; and (ii) LCD40. In some embodiments, the fusion protein further comprises one or more joining sites (JS), wherein the joining site comprises alanine and serine residues. In some embodiments, the joining site consists of alanine and serine residues. In some embodiments, the fusion protein comprises: (i) HDCR-JS-Ag-JS; and (ii) LDCR. In some embodiments, the fusion protein comprises (i) HCD40-JS-PL-JS-Ag-JS; and (ii) LCD40. In some embodiments, the peptide linker comprises a polypeptide with at least 80% sequence identity to SEQ ID NO:2. In some embodiments, the peptide linker comprises a polypeptide with at least 70, 75, 80, 81, 82, 83, 84, 85, 86, 87, 88, 89, 90, 91, 92, 93, 94, 95, 96, 97, 98, 99, or 100% sequence identity (or any derivable range therein) to SEQ ID NO:2, or a fragment of at least 7, 8, 9, 10, 11, 12, 13, 14, 15, 16, 17, 18, 19, 20, 21, 22, 23, 24, 25, or 26 (or any derivable range therein) contiguous amino acids of SEQ ID NO:2.

In some embodiments, PL-JS-Ag-JS comprises a polypeptide with at least 80% identity to SEQ ID NO:3. In some embodiments, PL-JS-Ag-JS comprises a polypeptide with at least 70, 75, 80, 81, 82, 83, 84, 85, 86, 87, 88, 89, 90, 91, 92, 93, 94, 95, 96, 97, 98, 99, or 100% sequence identity (or any derivable range therein) to SEQ ID NO:3, or a fragment of at least 100, 200, 300, 400, 500, 600, 610, 615, 620, 625, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, or 661 (or any derivable range therein) contiguous amino acids of SEQ ID NO:3.

In some embodiments, the anti-DC receptor antibody, e.g. the anti-CD40 antibody is a human or humanized antibody. In some embodiments, the anti-DC receptor antibody, e.g. the anti-CD40 antibody, comprises human IgG4 heavy chain constant region. In some embodiments, the human IgG4 heavy chain constant region comprises one or both of S241P and L248E substitutions according to Kabat numbering.

In some embodiments, the HCD40 comprises the complementarity determining regions CDR1H, CDR2H and CDR3H, the CDR1H having the amino acid sequence GFTFSDYYMY (SEQ ID NO:10), the CDR2H having the amino acid sequence YINSGGGSTYYPDTVKG (SEQ ID NO.:11), and the CDR3H having the amino acid sequence RGLPFHAMDY (SEQ ID NO.:12). In some embodiments, the LCD40 is comprises the complementarity determining regions CDR1L, CDR2L and CDR3L, the CDR1L having the amino acid sequence SASQGISNYLN (SEQ ID NO.:13) the CDR2L having the amino acid sequence YTSILHS (SEQ ID NO.:14) and the CDR3L having the amino acid sequence QQFNKLPPT (SEQ ID NO.:15). In some embodiments, the anti-DC receptor antibody comprises a HCD40 comprising the complementarity determining regions CDR1H, CDR2H and CDR3H, the CDR1H having the amino acid sequence GFTFSDYYMY (SEQ ID NO.:10), the CDR2H having the amino acid sequence YINSGGGSTYYPDTVKG (SEQ ID NO.:11), and the CDR3H having the amino acid sequence RGLPFHAMDY (SEQ ID NO.:12) and a LCD40 comprising the complementarity determining regions CDR1L, CDR2L and CDR3L, the CDR1L having the amino acid sequence SASQGISNYLN (SEQ ID NO.:13) the CDR2L having the amino acid sequence YTSILHS (SEQ ID NO.:14) and the CDR3L having the amino acid sequence QQFNKLPPT (SEQ ID NO.:15).

In some embodiments, the HCD40 comprises the complementarity determining regions CDR1H, CDR2H and CDR3H, the CDR1H having the amino acid sequence GYSFTGYYMH (SEQ ID NO.:18), the CDR2H having the amino acid sequence RINPYNGATSYNQNFKD (SEQ ID NO.:19), and the CDR3H having the amino acid sequence EDYVY (SEQ ID NO.:20). In some embodiments, the LCD40 is comprises the complementarity determining regions CDR1L, CDR2L and CDR3L, the CDR1L having the amino acid sequence RSSQSLVHSNGNTYLH (SEQ ID NO.:21) the CDR2L having the amino acid sequence KVSNRFS (SEQ ID NO.:22) and the CDR3L having the amino acid sequence SQSTHVPWT (SEQ ID NO.:23). In some embodiments, the anti-DC receptor antibody comprises a HCD40 comprising the complementarity determining regions CDR1H, CDR2H and CDR3H, the CDR1H having the amino acid sequence GYSFTGYYMH (SEQ ID NO.: 18), the CDR2H having the amino acid sequence RINPYNGATSYNQNFKD (SEQ ID NO.:19), and the CDR3H having the amino acid sequence EDYVY (SEQ ID NO.:20) and a LCD40 comprising the complementarity determining regions CDR1L, CDR2L and CDR3L, the CDR1L having the amino acid sequence RSSQSLVHSNGNTYLH (SEQ ID NO.:21) the CDR2L having the amino acid sequence KVSNRFS (SEQ ID NO.:22) and the CDR3L having the amino acid sequence SQSTHVPWT (SEQ ID NO.:23).

In some embodiments, the HCD40 comprises the complementarity determining regions CDR1H, CDR2H and CDR3H, the CDR1H having the amino acid sequence GYTFTDYVLH (SEQ ID NO.:26), the CDR2H having the amino acid sequence YINPYNDGTKYNEKFKG (SEQ ID NO.:27), and the CDR3H having the amino acid sequence GYPAYSGYAMDY (SEQ ID NO.:28). In some embodiments, the LCD40 is comprises the complementarity determining regions CDR1L, CDR2L and CDR3L, the CDR1L having the amino acid sequence RASQDISNYLN (SEQ ID NO.:29) the CDR2L having the amino acid sequence YTSRLHS (SEQ ID NO.:30) and the CDR3L having the amino acid sequence HHGNTLPWT (SEQ ID NO.:31). In some embodiments, the anti-DC receptor antibody comprises a HCD40 comprising the complementarity determining regions CDR1H, CDR2H and CDR3H, the CDR1H having the amino acid sequence GYTFTDYVLH (SEQ ID NO.:26), the CDR2H having the amino acid sequence YINPYNDGTKYNEKFKG (SEQ ID NO.:27), and the CDR3H having the amino acid sequence GYPAYSGYAMDY (SEQ ID NO.:28) and a LCD40 comprising the complementarity determining regions CDR1L, CDR2L and CDR3L, the CDR1L having the amino acid sequence RASQDISNYLN (SEQ ID NO.: 29) the CDR2L having the amino acid sequence YTSRLHS (SEQ ID NO.:30) and the CDR3L having the amino acid sequence HHGNTLPWT (SEQ ID NO.:31).

In some embodiments, the HCD40 comprises the complementarity determining regions CDR1H, CDR2H and CDR3H, the CDR1H having an amino acid sequence that is at least 75, 76, 77, 78, 79, 80, 81, 82, 83, 84, 85, 86, 87, 88, 89, 90, 91, 92, 93, 94, 95, 96, 97, 98, or 99% identical to one of SEQ ID NOS: 10, 18, and 26, the CDR2H having an amino acid sequence that is at least 75, 76, 77, 78, 79, 80, 81, 82, 83, 84, 85, 86, 87, 88, 89, 90, 91, 92, 93, 94, 95, 96, 97, 98, or 99% identical to one of SEQ ID NOS:11, 19, and 27, and the CDR3H having an amino acid sequence that is at least 75, 76, 77, 78, 79, 80, 81, 82, 83, 84, 85, 86, 87, 88, 89, 90, 91, 92, 93, 94, 95, 96, 97, 98, or 99% identical to one of SEQ ID NOS:12, 20, and 28. In some embodiments, the LCD40 is comprises the complementarity determining regions CDR1L, CDR2L and CDR3L, the CDR1L having an amino acid sequence that is at least 75, 76, 77, 78, 79, 80, 81, 82, 83, 84, 85, 86, 87, 88, 89, 90, 91, 92, 93, 94, 95, 96, 97, 98, or 99% identical to one of SEQ ID NOS: 13, 21, and 29, the CDR2L having an amino acid sequence that is at least 75, 76, 77, 78, 79, 80, 81, 82, 83, 84, 85, 86, 87, 88, 89, 90, 91, 92, 93, 94, 95, 96, 97, 98, or 99% identical to one of SEQ ID NOS: 14, 22, and 30, and the CDR3L having an amino acid sequence that is at least 75, 76, 77, 78, 79, 80, 81, 82, 83, 84, 85, 86, 87, 88, 89, 90, 91, 92, 93, 94, 95, 96, 97, 98, or 99% identical to one of SEQ ID NOS:15, 23, and 31.

In some embodiments, the HCD40 comprises a polypeptide with at least 80% sequence identity to SEQ ID NO:4. In some embodiments, the HCD40 comprises a polypeptide with at least 70, 75, 80, 81, 82, 83, 84, 85, 86, 87, 88, 89, 90, 91, 92, 93, 94, 95, 96, 97, 98, 99, or 100% sequence identity (or any derivable range therein) to SEQ ID NO:4. In some embodiments, the LCD40 comprises a polypeptide with at least 80% sequence identity to SEQ ID NO:5. In some embodiments, the LCD40 comprises a polypeptide with at least 70, 75, 80, 81, 82, 83, 84, 85, 86, 87, 88, 89, 90, 91, 92, 93, 94, 95, 96, 97, 98, 99, or 100% sequence identity (or any derivable range therein) to SEQ ID NO:5.

In some embodiments, the fusion protein comprises: (i) a HCD40-Ag fusion protein comprising an amino acid sequence with at least 80% sequence identity to SEQ ID NO:6; and (ii) a LCD40 comprising an amino acid sequence with at least 80% identity to SEQ ID NO:5.

Throughout the disclosure, LCD40 refers to a light chain of an anti-CD40 antibody. Likewise, HCD40 refers to a heavy chain of an anti-CD40 antibody.

Further aspects of the disclosure relate to a polynucleotide encoding for a fusion protein of the disclosure. In some embodiments, the polynucleotide comprise a nucleotide sequence that is at least 80% identical (or any derivable range therein) to SEQ ID NO: 7. In some embodiments, the polynucleotide comprise a nucleotide sequence that is at least 70, 75, 80, 81, 82, 83, 84, 85, 86, 87, 88, 89, 90, 91, 92, 93, 94, 95, 96, 97, 98, 99, or 100% identical (or any derivable range therein) to SEQ ID NO: 7. In some embodiments, the polynucleotide comprise a nucleotide sequence that is at least 80% identical (or any derivable range therein) to SEQ ID NO: 8. In some embodiments, the polynucleotide comprise a nucleotide sequence that is at least 70, 75, 80, 81, 82, 83, 84, 85, 86, 87, 88, 89, 90, 91, 92, 93, 94, 95, 96, 97, 98, 99, or 100% identical (or any derivable range therein) to SEQ ID NO: 8.

Further aspects relate to an expression vector comprising one or more polynucleotides of the disclosure. Yet further aspects relate to a host cell comprising one or more polynucleotides, expression vectors, or fusion proteins of the disclosure. In some embodiments, the host cells is a mammalian cell. In some embodiments, the mammalian cells comprise Chinese hamster ovary cells. Further aspects relate to a fusion protein isolated from a host cell of the disclosure.

Expression vectors may be constructed with diverse protein coding sequence e.g., fused in-frame to the H chain coding sequence. For example, HIV antigens may be expressed subsequently as Ab.Ag$_x$, which in the context of this invention, can have utility derived from using the anti-CD40 V-region sequence to bring the antigen directly to the surface of the antigen presenting cell bearing CD40. This permits internalization of e.g., antigen and ensuing initiation of therapeutic or protective action (e.g., via initiation of a potent immune response).

In some cases, particular amino acid sequences corresponding to anti-DC receptor monoclonal antibodies that are desirable components (in the context of e.g., humanized recombinant antibodies) of therapeutic or protective products. The following are such sequences in the context of chimeric mouse V region (underlined) human C region recombinant antibodies. These mouse V regions can be readily humanized, i.e., the combining regions grafted onto human V region framework sequences, by anyone well practiced in this art. Furthermore, the sequences can also be expressed in the context of fusion proteins that preserve antibody functionality, but add e.g., antigen for desired therapeutic applications.

Further aspects relate to a vaccine comprising a fusion protein of the disclosure and a pharmaceutically acceptable vehicle.

Further aspects relate to a method for treating or preventing from HIV infection in a subject comprising administering a fusion protein of the disclosure to the subject. Yet further aspects relate to a method for eliciting and/or enhancing B-cell and/or T-cell response against HIV, in a subject in need thereof, comprising administering to said subject in need thereof, a fusion protein or vaccine of the disclosure. Further aspects relate to a method for inducing IgG binding antibody responses to V1V2 region antigens in a subject in need thereof, the method comprising administering the fusion protein of the disclosure or the vaccine composition of the disclosure.

In some embodiments, the method further comprises administration of an immunostimulant. In some embodiments, the immunostimulant is administered sequentially or concomitantly to the vaccine composition. In some embodiments, the immunostimulant is mixed with the vaccine composition extemporaneously prior to injection of the vaccine composition to the subject.

Vaccine compositions may also contain one or more adjuvants. Additionally, the methods of the disclosure may also comprise the administration of one or more adjuvants. The adjuvants may be attached or conjugated directly or indirectly to one or more of the vaccine components, such as an antigen or antibody. In other embodiments the adjuvants may be provided or administered separately from the vaccine composition. In certain embodiments the adjuvant is poly ICLC, CpG, LPS, Immunoquid, PLA, GLA or cytokine adjuvants such as IFNα. In other embodiments the adjuvant may be a toll-like receptor agonist (TLR). Examples of TLR agonists that may be used comprise TLR1 agonist, TLR2 agonist, TLR3 agonist, TLR4 agonist, TLR5 agonist, TLR6 agonist, TLR7 agonist, TLR8 agonist or TLR9 agonist. In certain embodiments, a vaccine composition specifically does not contain PLA as an adjuvant. In some embodiments, the immunostimulant comprises a TLR agonist. In some embodiments, the TLR agonist comprises poly ICLC.

In some embodiments, the method excludes administration of a TLR agonist.

In some embodiments, an HIV vaccine comprises a population of dendritic cells (DC) activated with an antibody-antigen fusion protein (Ab.Ag) or an antibody-antigen complex (Ab:Ag) as described for anti-CD40 vaccines. In yet other embodiments a first HIV vaccine of the disclosure, e.g. anti-CD40 vaccine is combined with a second HIV vaccine. The second HIV vaccine may be selected from the group consisting of an attenuated recombinant virus or viral-vector based, Virus-like-particle (VLP) vaccine, DNA vaccine (naked or not), RNA-based vector vaccine, protein-based vaccine and a DC-targeting vaccine. In certain embodiments, the attenuated recombinant virus may be an attenuated recombinant poxvirus. In certain embodiments, the second vaccine is DNA-HIV-PT123.

In some embodiments, the method further comprises administration of an additional vaccine. In some embodiments, the additional vaccine is administered as a priming vaccine. In some embodiments, the additional vaccine comprises a vaccinia virus vaccine. In some embodiments, the additional vaccine comprises one or more of a gag, pol, and nef peptide.

In some embodiments, the administration comprises intradermal, intramuscular, or subcutaneous administration.

In some embodiments, the additional vaccine comprises an attenuated recombinant poxvirus. In some embodiments, the additional vaccine is selected from the group consisting of NYVAC, ALVAC and MVA virus. Specifically, the NYVAC virus may be a NYVAC-KC virus.

In some embodiments, the HIV vaccine, e.g. anti-CD40 HIV vaccine, is used in a method for potentiating an immune response to at least one HIV epitope comprising administering to a patient such HIV vaccine as described herein. In some embodiments, such HIV vaccine is used to prevent healthy subject to be infected by HIV, comprising administering such HIV vaccine of the present disclosure, e.g. HIV anti-CD40 vaccine to a healthy subject, not infected by HIV (preventive treatment). In other embodiments, the HIV vaccine of the present disclosure is used in a method of treating a patient in the early stages of an HIV infection comprising administering to a patient an anti-CD40 HIV vaccine.

It is contemplated that at least one HIV antigen elicits at least one of a humoral and/or a cellular immune response in a host, preferably a human patient or a primate.

Further aspects of the disclosure relate to a method for making an anti-DC receptor antibody-HIV antigen fusion protein, the method comprising expressing and polynucleotide of the disclosure or an expression vector of the disclosure in a host cell and purifying the fusion protein from the host cell. In some embodiments, the host cell is a CHO cell. In some embodiments, at least 1.5 mg/mL of the fusion protein is purified. In some embodiments, at least 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9. 3.0, 3.2, 3.4, 3.6, 3.8, or 4 mg/mL (or any derivable range therein) is purified from the host cell.

The preparation of HIV vaccine as the active immunogenic ingredient, may be prepared as injectables, either as liquid solutions or suspensions; solid forms suitable for solution in, or suspension in, liquid prior to infection can also be prepared. The preparation may be emulsified, encapsulated in liposomes. The active immunogenic ingredients are often mixed with carriers which are pharmaceutically acceptable and compatible with the active ingredient.

The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants that may be effective include but are not limited to: aluminum hydroxide, N-acetyl-muramyl-L-threonyl-D- isoglutamine (thr-MDP), N-acetyl-nor-muramyl-L-alanyl-D-isoglutamine, MTP-PE and RIBI, which contains three components extracted from bacteria, monophosphoryl lipid A, trehalose dimycolate and cell wall skeleton (MPL+ TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-[gamma], IL-2 and IL-12) or synthetic IFN-[gamma] inducers such as poly I:C or poly ICLC (Hiltonol) can be used in combination with adjuvants described herein.

Vaccines may include an effective amount of the antibody-antigen fusion protein (Ab.Ag) or the antibody-antigen complex (Ab:Ag), dissolved or dispersed in a pharmaceutically acceptable carrier or aqueous medium. Such compositions can also be referred to as inocula. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions. The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Administration of vaccines according to the present invention will be via any common route so long as the target tissue is available via that route in order to maximize the delivery of antigen to a site for maximum (or in some cases minimum) immune response. Administration will generally be by orthotopic, intradermal, mucosally, subcutaneous, intramuscular, intraperitoneal or intravenous injection. Other areas for delivery include: oral, nasal, buccal, rectal, vaginal or topical. Vaccines of the invention are preferably administered parenterally, by injection, for example, either subcutaneously or intramuscularly.

Vaccines may be administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms active ingredient per vaccination with a range from about 0.1 mg to 1000 mg, such as in the range from about 1 mg to 300 mg, or in the range from about 10 mg to 50 mg. Suitable regiments for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of nucleic acid molecule or fusion polypeptides of this invention will depend, inter alia, upon the administration schedule, the unit dose of antigen administered, whether the antibody-antigen fusion protein (Ab.Ag) or the antibody-antigen complex (Ab:Ag) is administered in combination with other therapeutic agents, the immune status and health of the recipient, and the therapeutic activity of the particular the Ab.Ag or the Ab:Ag.

A vaccine may be given in a single dose schedule or in a multiple dose schedule. A multiple dose schedule is one in which a primary course of vaccination may include, e.g., 1-10 separate doses, followed by other doses given at subsequent time intervals required to maintain and or reinforce the immune response, for example, at 1-4 months for a second dose, and if needed, a subsequent dose(s) after several months. Periodic boosters at intervals of 1-5 years, usually 3 years, are desirable to maintain the desired levels of protective immunity. The course of the immunization can be followed by in vitro proliferation assays of peripheral blood lymphocytes (PBLs) co-cultured with gp140 antigen, and by measuring the levels of IFN-[gamma] released from the primed lymphocytes. The assays may be performed using conventional labels, such as radionucleotides, enzymes, fluorescent labels and the like. These techniques are known to one skilled in the art and can be found in U.S. Pat. Nos. 3,791,932, 4,174,384 and 3,949,064, relevant portions incorporated by reference.

A vaccine may be provided in one or more "unit doses". Unit dose is defined as containing a predetermined-quantity of the vaccine calculated to produce the desired responses in association with its administration, i.e., the appropriate route and treatment regimen. The quantity to be administered, and the particular route and formulation, are within the skill of those in the clinical arts. The subject to be treated may also be evaluated, in particular, the state of the subject's immune system and the protection desired. A unit dose need not be administered as a single injection but may include continuous infusion over a set period of time. The amount of vaccine delivered can vary from about 0.001 to about 0.05 mg/kg body weight, for example between 0.1 to 5 mg per subject. Thus, in particular embodiments, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg (or any derivable range therein), of the antibody-HIV antigen fusion protein in the vaccine and/or additional vaccine may be delivered to an individual in vivo. In some embodiments, the amount of vaccine delivered can be at least, at most, or exactly about 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.012 mg/kg, 0.014 mg/kg, 0.016 mg/kg, 0.018 mg/kg, 0.02 mg/kg, 0.022 mg/kg, 0.024 mg/kg, 0.026 mg/kg, 0.028 mg/kg, 0.03 mg/kg, 0.032 mg/kg, 0.034 mg/kg, 0.036 mg/kg, 0.038 mg/kg, 0.04 mg/kg, 0.042 mg/kg, 0.044 mg/kg, 0.046 mg/kg, 0.048 mg/kg, 0.05 mg/kg, 0.052 mg/kg, 0.054 mg/kg, 0.056 mg/kg, 0.058 mg/kg, 0.06 mg/kg, 0.062 mg/kg, 0.064 mg/kg, 0.066 mg/kg, 0.068 mg/kg, or 0.07 mg/kg (or any derivable range therein), of the antibody-HIV antigen fusion protein in the vaccine and/or additional vaccine may be delivered to an individual in vivo. The dosage of vaccine to be administered depends to a great extent on the weight and physical condition of the subject being treated as well as the route of administration and the frequency of treatment.

In another aspect, embodiments relate to a combined HIV vaccine comprising a first HIV vaccine as described above and a second HIV vaccine. Therefore, in some methods a patient may be administered both an HIV vaccine composition discussed above, such as a dendritic-cell antibody attached to an HIV antigen, and a recombinant attenuated poxvirus that encodes for at least one HIV antigen. It is contemplated that in some embodiments the recombinant attenuated poxvirus is administered after the first HIV vaccine composition has been administered. It is further contemplated that the HIV antigens provided to the patient in the first and second HIV vaccines may be the same or they may be different. It is also contemplated that the administration of the first and second vaccines can be reversed such that the second vaccine is administered first and the first vaccine is administered second. It additionally contemplated that the first and second vaccines be administered at the same time. In instances when the first and second vaccines are not administered at the same time it is contemplated that the vaccines may be administered 1, 2, 3, 4, 5, 6, 7, 8, 9, 10, 11, 12, 13 or 14 days apart or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 or 52 weeks apart or 1, 2, 3, 4, 5, 6, 7, 8, 9, 10, 11, 12, 13, 14, 15, 16, 17, 18, 19, 20, 21, 22, 23, 24, 36, 48, 60, 72, 84 or 96 months apart or 1, 2, 3, 4, 5, 6, 7, 8, 9, 10, 11, 12, 13, 14, 15, 16, 17, 18, 19 or 20 years apart (or any derivable range therein. Furthermore, any one vaccine (either the fusion protein of the disclosure or the additional vaccine) may be administered at least, at most, or exactly 1, 2, 3, 4, 5, 6, 7, 8, 9, or 10 times (or any derivable range therein) through one course of treatment, such as a prescribed course of treatment by a medical professional. When the vaccine is administered more than once, it may be administered at least, at most, or exactly 1, 2, 3, 4, 5, 6, 7, 8, 9, 10, 11, 12, 13 or 14 days apart or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 or 52 weeks apart or 1, 2, 3, 4, 5, 6, 7, 8, 9, 10, 11, 12, 13, 14, 15, 16, 17, 18, 19, 20, 21, 22, 23, 24, 36, 48, 60, 72, 84 or 96 months apart or 1, 2, 3, 4, 5, 6, 7, 8, 9, 10, 11, 12, 13, 14, 15, 16, 17, 18, 19 or 20 years apart (or any derivable range therein).

In one embodiment, the second HIV vaccine is selected from the group consisting of an attenuated recombinant virus or viral-vector based, Virus-like-particle (VLP) vaccine, DNA vaccine (naked or not), RNA-based vector vaccine, protein-based vaccine and a DC-targeting vaccine. In certain embodiments, the attenuated recombinant virus may be an attenuated recombinant poxvirus.

Further aspects relate to a kit comprising a fusion protein of the disclosure, a polynucleotide of the disclosure, an expression vector of the disclosure, or a host cell of the disclosure, and; optionally, instructions for use of the kit. The kit may be used to perform the methods described herein. In some embodiments, the kit is for eliciting a T cell response and/or a B cell response in a subject; wherein the kit comprises the fusion protein of the disclosure or the vaccine of the disclosure.

As used herein, the term "attenuated recombinant virus" refers to a virus that has been genetically altered by modern molecular biological methods, e.g. restriction endonuclease and ligase treatment, and rendered less virulent than wild type, typically by deletion of specific genes or by serial passage in a non-natural host cell line or at cold temperatures.

In one particular embodiment, the attenuated recombinant virus is an attenuated recombinant poxvirus.

"Poxviruses" are large, enveloped viruses with double-stranded DNA that is covalently closed at the ends. Pox viruses replicate entirely in the cytoplasm, establishing discrete centers of viral synthesis. Their use as vaccines has been known since the early 1980's (see, e.g. Panicali, et al., 1983).

In one particular embodiment, the attenuated recombinant poxvirus is selected from the group consisting of NYVAC, ALVAC and MVA virus. In one embodiment, the NYVAC virus is a NYVAC-KC virus. In other embodiments, the second HIV vaccine is DNA-HIV-PT123.

In some embodiments, the mAb is humanized (i.e., converted to a sequence which retains the original key residues crucial for receptor binding, but has variable region framework and constant region sequences that are typically found in human antibodies).

As used herein, the term "vaccine" is intended to mean a composition which can be administered to humans or to animals in order to induce an immune response; this immune response can result in a production of antibodies or simply in the activation of certain cells, in particular antigen-presenting cells, T lymphocytes and B lymphocytes. In certain embodiments the vaccine is capable of producing an immune response that leads to the production of neutralizing antibodies in the patient with respect to the antigen provided in the vaccine. The vaccine can be a composition for prophylactic purposes or for therapeutic purposes, or both.

As used herein, the term "antigen" refers to any antigen that can be used in a vaccine, whether it involves a whole microorganism or a portion thereof, and various types: (e.g., peptide, protein, glycoprotein, polysaccharide, glycolipid, lipopeptide, etc). Thus, the term "antigen" refers to a molecule that can initiate a humoral and/or cellular immune response in a recipient of the antigen. The antigen is usually a molecule that causes a disease for which a vaccination would be advantageous treatment. Within the context of the invention, the antigens are human immunodeficiency virus (HIV) antigens; the term "antigen" also comprises the polynucleotides, the sequences of which are chosen so as to encode the antigens whose expression by the individuals to which the polynucleotides are administered is desired, in the case of the immunization technique referred to as DNA immunization.

As used herein, the term "antibodies" refers to immunoglobulins, whether natural or partially or wholly produced artificially, e.g. recombinant. An antibody may be monoclonal or polyclonal. The antibody may, in some cases, be a member of one, or a combination immunoglobulin classes, including: IgG, IgM, IgA, IgD, and IgE.

As used herein, the term "antibody or fragment thereof," includes whole antibodies or fragments of an antibody, e.g., Fv, Fab, Fab', F(ab')2, Fc, and single chain Fv fragments (ScFv) or any biologically effective fragments of an immunoglobulins that binds specifically to, e.g., CD40. Antibodies from human origin or humanized antibodies have lowered or no immunogenicity in humans and have a lower number or no immunogenic epitopes compared to non-human antibodies. Antibodies and their fragments will generally be selected to have a reduced level or no antigenicity in humans. A polypeptide that has one or more CDRs from a monoclonal antibody and that may have at least as good as a binding specificity and/or affinity of a monoclonal antibody may be referred to as an "antibody fragment" or a polypeptide comprises an antibody fragment.

Typically, the term "antibody or fragment thereof" describes a recombinant antibody system that has been engineered to provide a target specific antibody. The monoclonal antibody made using standard hybridoma techniques, recombinant antibody display, humanized monoclonal antibodies and the like. The antibody can be used to, e.g., target (via one primary recombinant antibody against an internalizing receptor, e.g., a human dendritic cell receptor such as CD40) one or several antigens and/or one adjuvant to dendritic cells. Any embodiment discussed in the context of an antibody may be implemented in the context of an antibody fragment, including a polypeptide comprising one or more CDRs from an antibody, more specifically an antibody comprising the CDRs 1, 2 and 3 of the heavy chain variable region of a specific antibody and the CDRs 1, 2 and 3 of the light chain variable region of the same specific antibody.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and other fragments that exhibit immunological binding properties of the parent monoclonal antibody molecule.

As used herein, the term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" (FRs). As used herein, the term "FR" refers to amino acid sequences which are found naturally between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions" or "CDRs".

As used herein, the term "humanized" antibody refers to those molecules comprising an antigen-binding site derived from a non-human immunoglobulin have been described, including chimeric antibodies having rodent V regions and their associated CDRs fused to human constant domains, rodent CDRs grafted into a human supporting FR prior to fusion with an appropriate human antibody constant domain, and rodent CDRs supported by recombinantly veneered rodent FRs. These "humanized" molecules are designed to minimize unwanted immunological response toward rodent antihuman antibody molecules, which limits the duration and effectiveness of therapeutic applications of those moieties in human recipients.

The terms "adjuvant" or "immunoadjuvant" may be used interchangeably and refer to a substance that enhances, augments or potentiates the host's immune response to an antigen, e.g., an antigen that is part of a vaccine. Non-limiting examples of some commonly used vaccine adjuvants include insoluble aluminum compounds, calcium phosphate, liposomes, Virosomes™, ISCOMS®, microparticles (e.g., PLG), emulsions (e.g., MF59, Montanides), virus-like particles & viral vectors. PolyICLC (a synthetic complex of carboxymethylcellulose, polyinosinic-polycytidylic acid, and poly-L-lysine double-stranded RNA), which is a TLR3 agonist, is used as an adjuvant in the present invention. It will be understood that other TLR agonists may also be used (e.g. TLR4 agonists, TLR5 agonists, TLR7 agonists, TLR9 agonists; also as described in PCT publication number WO/2012/021834 or WO/2012/122396, the contents of which are incorporated herein by reference), or any combinations or modifications thereof.

As used herein, the term "conjugate" refers to any substance formed from the joining together of two parts. Representative conjugates in accordance with the present invention include those formed by joining together of the antigen with the antibody and/or the adjuvant. The term "conjugation" refers to the process of forming the conjugate and is usually done by physical coupling, e.g. covalent binding, co-ordination covalent, or secondary binding forces, e.g. Van der Waals bonding forces. The process of linking the antigen to the antibody and/or to the adjuvant can also be done via a non-covalent association such as a dockerin-cohesin association (as described in U.S. Patent Publication No. 20100135994, Banchereau et al. relevant portions incorporated herein by reference) or by a direct chemical linkage by forming a peptide or chemical bond.

As used herein, "Dendritic Cells" (DCs) refers to any member of a diverse population of morphologically similar cell types found in lymphoid or non-lymphoid tissues. These cells are characterized by their distinctive morphology, high levels of surface MHC-class II expression (Steinman, et al., 1991); incorporated herein by reference for its description of such cells). These cells can be isolated from a number of tissue sources, and conveniently, from peripheral blood, as described herein.

As used herein, the term "HIV" refers to the human immunodeficiency virus. HIV includes, without limitation, HIV-1. HIV may be either of the two known types of HIV, i.e., HIV-1 or HIV-2. The HIV-1 virus may represent any of the known major subtypes or clades (e.g., Classes A, B, C, D, E, F, G, J, and H) or outlying subtype (Group O). Also encompassed are other HIV-1 subtypes or clades that may be isolated.

Methods are provided for preventing or treating an HIV infection comprising administering to a subject in need thereof an HIV vaccine or a combination of vaccines as discussed above or herein. In certain embodiments, there are methods for inducing an immune response to at least one HIV epitope comprising administering to a subject in need thereof an HIV vaccine or a combination of vaccines as discussed above or herein. Other methods are provided for potentiating an immune response to at least one HIV epitope comprising administering to a subject in need thereof an HIV vaccine or a combination of vaccines as discussed above or herein.

In some embodiments, there are methods of preventing a subject from being infected by HIV comprising administering to a subject, for example a healthy subject diagnosed as non-infected by HIV, an HIV vaccine or combination of vaccines as discussed above or herein.

In further embodiments there are methods of treating a patient in the early stages of an HIV infection comprising administering to the patient an HIV vaccine or a combination of vaccines as discussed above or herein.

In some cases, there are methods of treating a patient comprising administering to the patient an HIV vaccine or a combination of vaccines as discussed above or herein.

Methods may involve a patient tested for an HIV infection, a patient determined to be infected with HIV, a patient with symptoms of early stage HIV infection, a patient who is at risk for HIV infection, a patient whose HIV infection status is known, or a patient previously treated for HIV infection. In certain embodiments, the patient is a patient who is pregnant. In other embodiments, a patient is a pediatric patient whose mother was infected with HIV. In other embodiments, the patient is a pediatric patient above the age of 13 years old. In certain embodiments, the patient has been exposed to HIV.

In some embodiments, methods further comprise testing the patient for HIV infection or diagnosing a patient with HIV infection. Additional methods may also involve treating a patient also with other HIV treatments such as HIV/AIDS small molecule treatments.

In certain aspects, methods further comprise generating a neutralizing antibody. In certain instances, said method comprises administering an HIV vaccine composition of the present disclosure.

Any embodiment discussed in the context of an antibody may be implemented in any method embodiment discussed herein.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-H. Serum Env gp140-specific IgG responses elicited by αLOX-1.Env gp140 and αCD40.Env gp140 fusion protein administration. Total binding IgG antibody levels against Clade C gp140 (Vaccine Strain, ZM96) (A), Group M gp140 (Consensus) (B), Clade C gp140 (Consensus) (C), Clade B gp140 (Consensus) (D), Clade B V1-V2 Env (gp70 B.CaseA V1V2) (E), and Clade C V1-V2 (C.1086C V1V2 Tags) (F), Clade AE V1-V2 (AE.A244 V1V2 Tags) (G), Clade AE V2 (AE.A244 V2 Tags) (H) induced by the different vaccination groups are shown. Individual serum samples were obtained at weeks 6, 14, 26, and 32 from each macaque (n=6 per group) immunized as per G1 N2[LpN]2, G2 N2[CpN]2, G3 N2Lp2, G4 N2Cp2, and G5 N2C2 (Table 1). Binding antibodies were measured by BAMA as indicated in Materials and Methods. The magnitudes of the antibody responses are expressed as the AUC from serial dilutions of plasma. Each dot represents the value for one individual macaque. Weeks of sampling are indicated above each frame and groups are defined below each frame. Response rates for each group are given above each dataset. The mid-line of the box denotes the median, and the ends of the box denote the $25^{th}$ and $75^{th}$ percentiles. The whiskers that extend from the top and bottom of the box extend to the most extreme data points that are no more than 1.5 times the interquartile range (i.e., the height of the box) or if no value meets this criterion, to the data extremes. Table 2 shows statistical analysis of paired comparisons of serum IgG responses against various Env antigens, including those exemplified in this figure.

Figure 6:
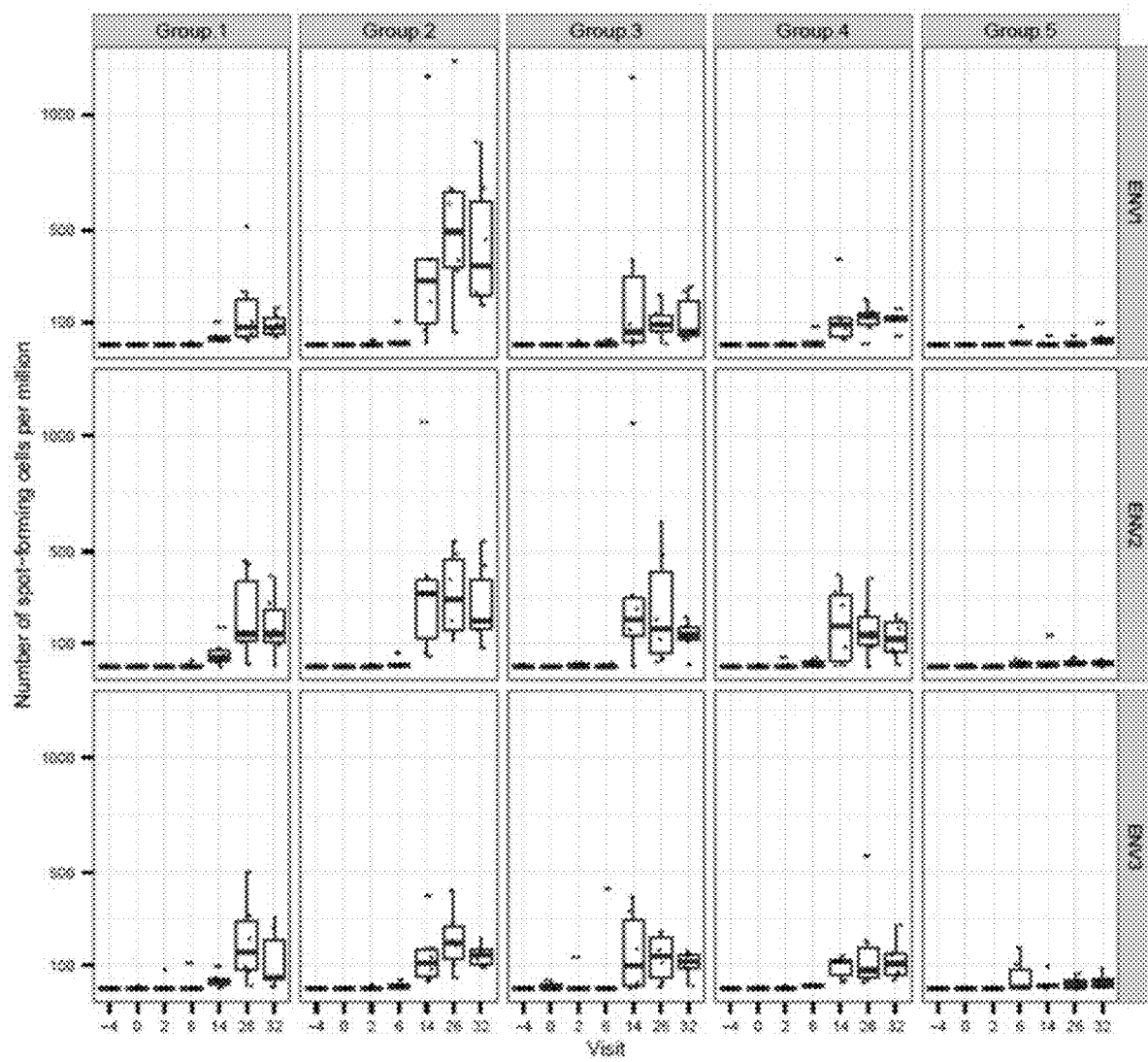
FIG. 6. Blood HIV-1 antigen-specific T cell responses elicited by αLOX-1.Env gp140 and αCD40.Env gp140 fusion protein administration. PBMCs were analyzed by IFNγ ELISPOT for responses to three Env gp140 peptide pools. Sample collection times are shown in weeks below the graph. Dots are results for individual animals and the box plots represent the distribution of values with the bars indicating the median values for the group. No significant responses were detected against non-Env HIV peptides (not shown). Statistical analysis of blood HIV-1 antigen-specific T cell responses elicited at week 26 by αLOX-1.Env gp140 and αCD40.Env gp140 fusion protein administration IFNγ ELISPOT responses summed over all antigens were by the Wilcoxon rank sum test showed G1 vs. G3 (p=0.699), G2 vs. G4 (p=0.065), G1 vs. G2 (p=0.180), G3 vs. G4 (p=0.818) and G4 vs. G5 (p=0.143). For the week 32 data the analysis showed G1 vs. G3 (p=0.699), G2 vs. G4 (p=0.009*), G1 vs. G2 (p=0.015*), G3 vs. G4 (p=1.000) and G4 vs. G5 (p=0.010*).
Figure 7:
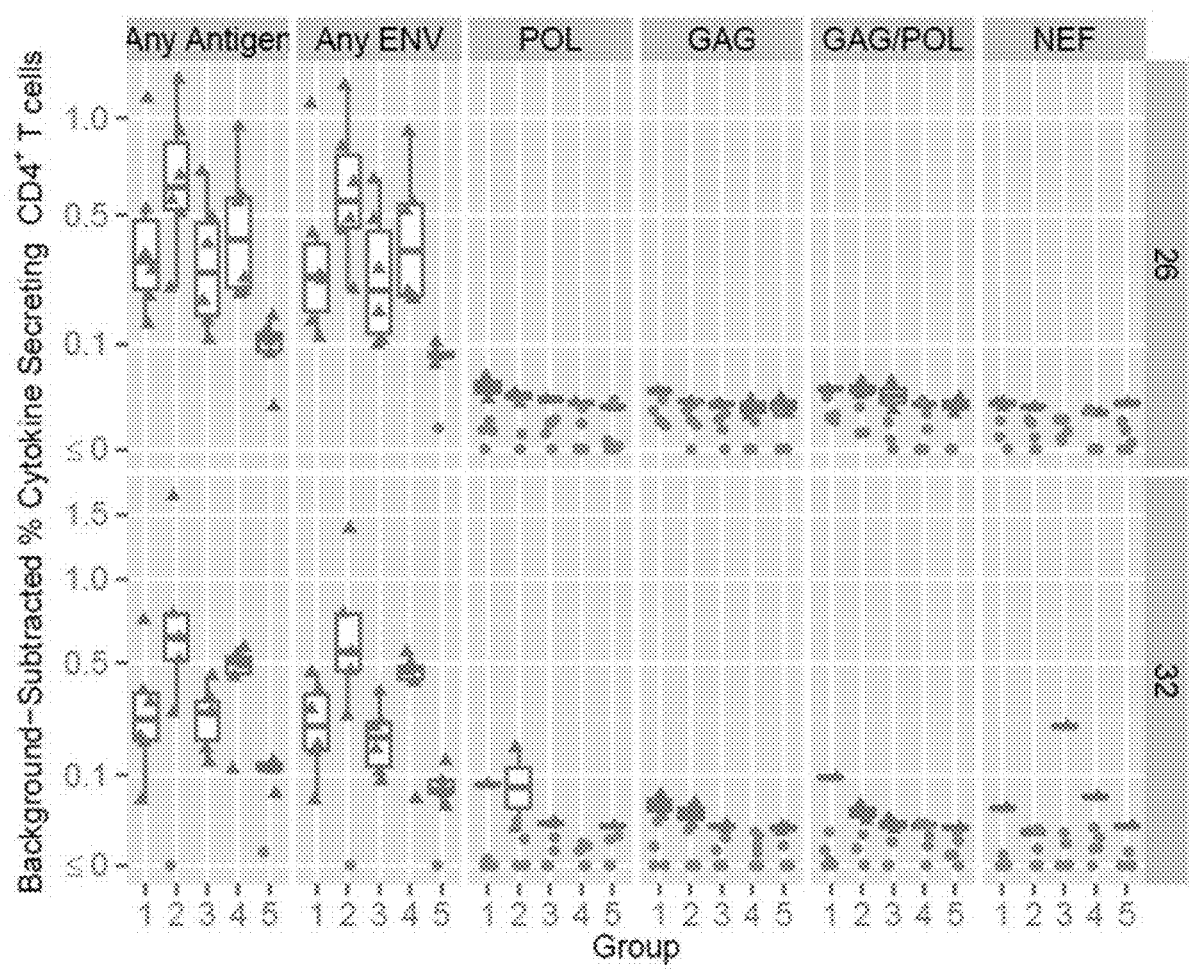

FIG. 7. Specificity and magnitude of blood HIV-1 antigen-specific CD4+ T cell responses elicited by αLOX-1.Env gp140 and αCD40.Env gp140 fusion protein administration. PBMCs from blood collected at week 26, and 32 were analyzed by ICS for CD4+ T cell responses to HIV-1 antigen peptide pools (indicated above the graph). In contrast to FIG. 6, these data combine IFNγ, IL-2, and TNFα cytokine secretion responses as well as integrating responses across All Env (the response patterns represented with combined cytokine responses were similar to those seen when the individual cytokine responses were plotted). Dots are results for individual animals and the box plots represent the distribution of values with the bars indicating the median values for the responders in the group (indicated below each panel).

Figure 8:
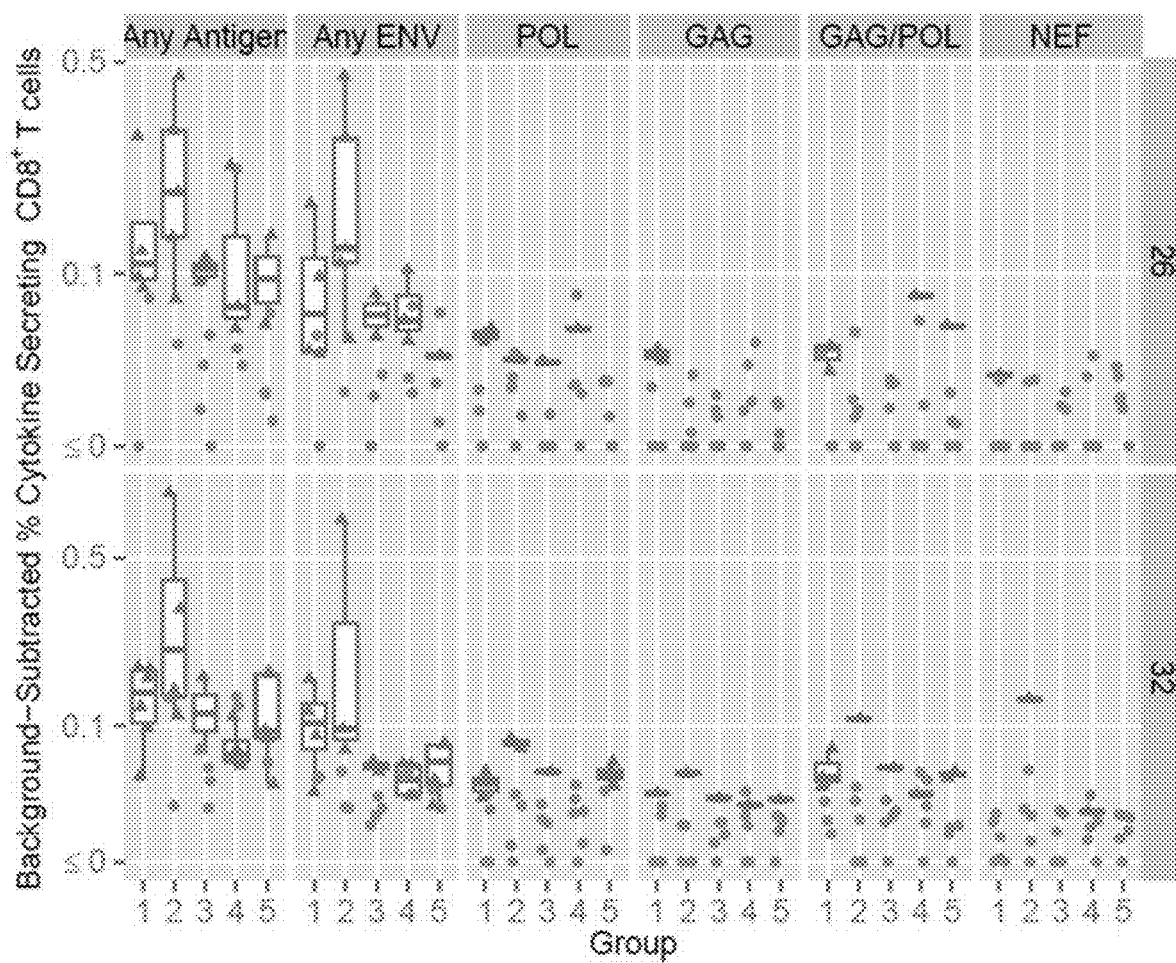

FIG. 8. Specificity and magnitude of blood HIV-1 antigen-specific CD8+ T cell responses elicited by αLOX-1.Env gp140 and αCD40.Env gp140 fusion protein administration. PBMCs from blood collected at week 26 and 32 were analyzed by ICS for CD8+ T cell responses to HIV-1 antigen peptide pools (indicated above the graph). In contrast to FIG. 6, the data combine IFNγ, IL-2, and TNFα cytokine secretion responses as well as integrating responses across All Env (the response patterns represented with combined cytokine responses were similar to those seen when the individual cytokine responses were plotted). Dots are results for individual animals and the box plots represent the distribution of values with the bars indicating the median values for the responders in the group (indicated below each panel).

Figures 9A, 9B:
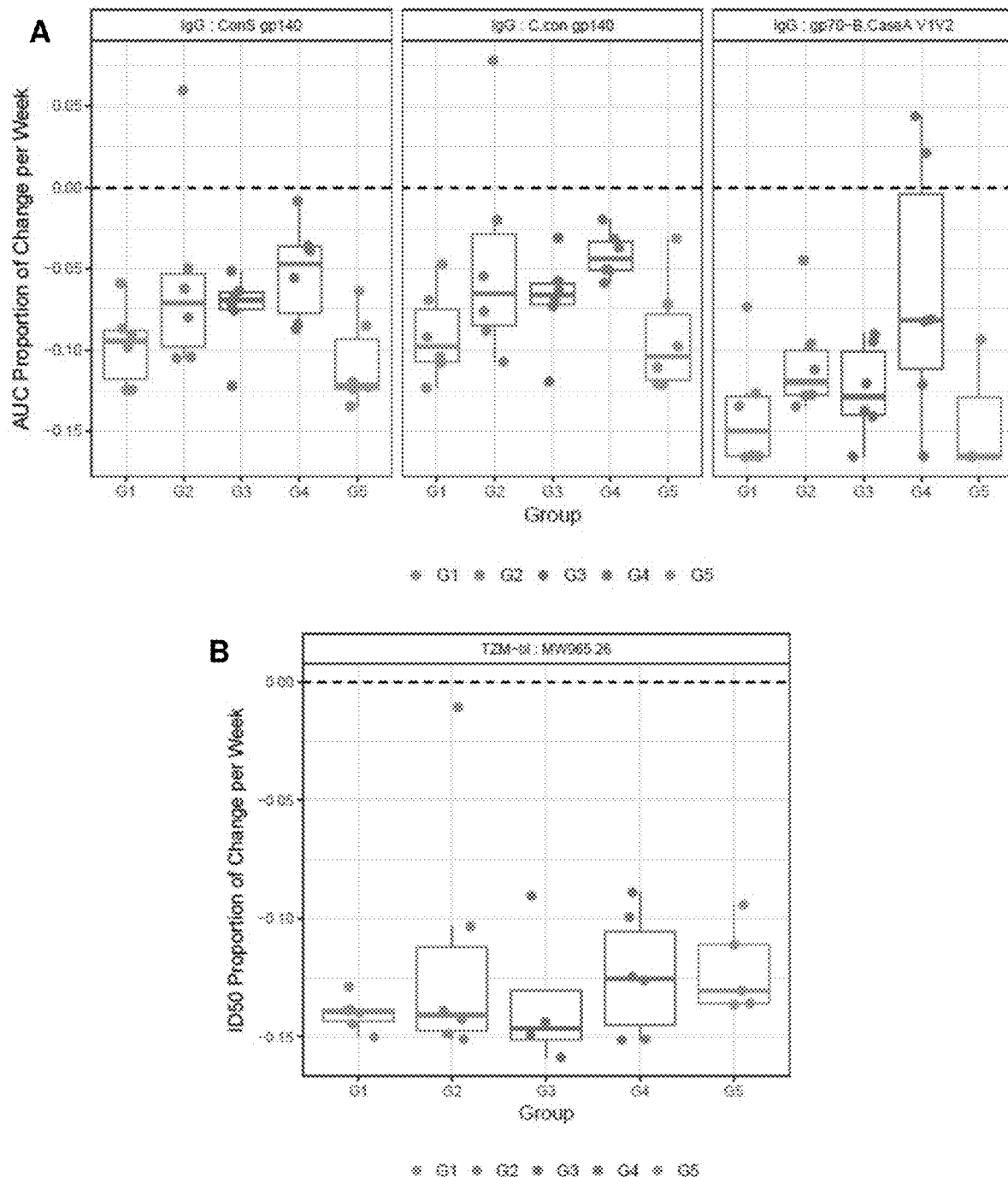

FIG. 9A-B. Durability of plasma IgG binding (A) and serum neutralizing (B) antibody responses evaluated as proportion of change per week. Proportion of change per week is calculated as [(Response at durability time point−response at peak time point)/Response at peak time point]/number of weeks between peak and durability time points, and is only calculated for animals that showed positive response for peak immunity time point. The mid-line of the box denotes the median, and the ends of the box denote the $25^{th}$ and $75^{th}$ percentiles. The whiskers that extend from the top and bottom of the box extend to the most extreme data points that are no more than 1.5 times the interquartile range (i.e., the height of the box) or if no value meets this criterion, to the data extremes. For binding antibody response, AUC from titration data in BAMA are used for the calculation. ID50 titers are used for neutralization response. Descriptive statistics of these values and results for between-group comparisons are in Table 5.

FIG. 10A-D. Pair-wise comparison of magnitude of binding (A), neutralizing (B), ADCC (C), and T cell responses (D) between DC-targeted gp140 boost regimens (G1-G5 current study and ExtDC-N2Lp3) and the non-DC-targeting gp120 boost regimen ExtNDC-N2[NP]2 at peak immunity time point. In particular note, IgG binding to Con S gp140 CF for the ExtNDC-N2[NP]2 group was 4 to 11-fold higher than G1-G5 in the current study, with P values ≤0.0002 for each group in pair-wise comparison (2-tailed t test) (Table 6). IgG binding to gp70-B.CaseA V1V2 scaffold for the ExtNDC-N2[NP]2 animals was 4 to 27-fold that of G1-G5 in the current study with P values <0.01 in pair-wise comparison (2-tailed t test). IgA response was also significantly higher for the ExtNDC-N2[NP]2 animals compared to G1-G5 in the current study (Table 6). For B values are significantly higher in the ExtNDC-N2[NP]2 group compared to G1-G5 with P values <0.01 for most (2-tailed t test) (Table 7). The highest difference was seen against Tier 1A clade C MW965.26, where ExtNDC-N2[NP]2 showed 7 to 29-fold higher ID50 titer compared to G1-G5 of current study. ADCC response measured with Env coated cells was significantly higher for ExtNDC-N2[NP]2 compared to all 5 groups in current study at week 26. The differences ranged from 3-12 fold for AUC values (Table 8).

FIG. 11A-B. Durability of binding (A) and neutralizing (B) antibody responses evaluated as proportion of change per week. See FIG. 9 legend for calculation of proportion of change per week. For binding antibody response, AUC from titration data in BAMA are used for the calculation. ID50 titers are used for neutralization response. Boxes show 95% confidence interval and thick bars show mean of group. Proportion of change per week was only calculated for animals that showed positive response for both peak and durability time points. Descriptive statistics of these values and for values on additional antigens tested in BAMA are in Table 10.

DESCRIPTION OF ILLUSTRATIVE EMBODIMENTS

As shown in the Examples of the application, anti-CD40-env gp140 fusion proteins increased B cell and T cell responses in vaccinated animals. The responses were robust, cross-reactive, and contained antibodies specific to multiple epitopes within gp140 including the C1, C2, V1-3, C4, C5, and gp41 immuno-dominant regions. The DC-targeting vaccines also elicited modest serum Env-specific IgA responses. Furthermore, CD4+ and CD8+ T cell responses specific to multiple Env epitopes were strongly boosted by the DC-targeting vaccines administered in combination with poly ICLC.

I. Nucleic Acids

In certain embodiments, there are recombinant nucleic acids encoding the proteins, polypeptides, or peptides described herein. Polynucleotide contemplated for use in methods and compositions include those encoding antibodies to CD40 or binding portions thereof.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or fewer in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode a polypeptide (e.g., an antibody or fragment thereof) that binds to DC receptors, such as CD40. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

A. Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody or fusion protein of the disclosure.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

In certain embodiments the host cell may be any prokaryotic or eukaryotic cell. In some aspects the host cell is an animal cell. Exemplary host cells include A549, B-cells, B16, BHK-21, C2C12, C6, CaCo-2, CAP/, CAP-T, CHO, CHO2, CHO-DG44, CHO-K1, COS-1, Cos-7, CV-1, Dendritic cells, DLD-1, Embryonic Stem (ES) Cell or derivative, H1299, HEK, 293, 293T, 293FT, Hep G2, Hematopoietic Stem Cells, HOS, Huh-7, Induced Pluripotent Stem (iPS) Cell or derivative, Jurkat, K562, L5278Y, LNCaP, MCF7, MDA-MB-231, MDCK, Mesenchymal Cells, Min-6, Monocytic cell, Neuro2a, NIH 3T3, NIH3T3L1, K562, NK-cells, NS0, Panc-1, PC12, PC-3, Peripheral blood cells, Plasma cells, Primary Fibroblasts, RBL, Renca, RLE, SF21, SF9, SH-SY5Y, SK-MES-1, SK-N-SH, SL3, SW403, Stimulus-triggered Acquisition of Pluripotency (STAP) cell or derivate SW403, T-cells, THP-1, Tumor cells, U2OS, U937, peripheral blood lymphocytes, expanded T cells, hematopoietic stem cells, or Vero cells.

In some embodiments, cells may be subjected to limiting dilution methods to enable the expansion of clonal populations of cells. The methods of limiting dilution cloning are well known to those of skill in the art. Such methods have been described, for example for hybridomas but can be applied to any cell. Such methods are described in (Cloning hybridoma cells by limiting dilution, Journal of tissue culture methods, 1985, Volume 9, Issue 3, pp 175-177, by Joan C. Rener, Bruce L. Brown, and Roland M. Nardone) which is incorporated by reference herein.

In other embodiments, media may be formulated using components well-known to those skilled in the art. Formulations and methods of culturing cells are described in detail in the following references: Short Protocols in Cell Biology J. Bonifacino, et al., ed., John Wiley & Sons, 2003, 826 pp; Live Cell Imaging: A Laboratory Manual D. Spector & R. Goldman, ed., Cold Spring Harbor Laboratory Press, 2004, 450 pp.; Stem Cells Handbook S. Sell, ed., Humana Press, 2003, 528 pp.; Animal Cell Culture: Essential Methods, John M. Davis, John Wiley & Sons, Mar. 16, 2011; Basic Cell Culture Protocols, Cheryl D. Helgason, Cindy Miller, Humana Press, 2005; Human Cell Culture Protocols, Series: Methods in Molecular Biology, Vol. 806, Mitry, Ragai R.; Hughes, Robin D. (Eds.), 3rd ed. 2012, XIV, 435 p. 89, Humana Press; Cancer Cell Culture: Method and Protocols, Cheryl D. Helgason, Cindy Miller, Humana Press, 2005; Human Cell Culture Protocols, Series: Methods in Molecular Biology, Vol. 806, Mitry, Ragai R.; Hughes, Robin D. (Eds.), 3rd ed. 2012, XIV, 435 p. 89, Humana Press; Cancer Cell Culture: Method and Protocols, Simon P. Langdon, Springer, 2004; Molecular Cell Biology. 4th edition, Lodish H, Berk A, Zipursky S L, et al., New York: W.H. Freeman; 2000, Section 6.2Growth of Animal Cells in Culture, all of which are incorporated herein by reference.

C. Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

II. Proteinaceous Compositions

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Table, below).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |

-continued

| Codon Table | | | |
|---|---|---|---|
| Amino Acids | | | Codons |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second or further-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein).

A. Polypeptides and Polypeptide Production

Embodiments involve polypeptides, peptides, and proteins and immunogenic fragments thereof for use in various aspects described herein. For example, specific antibodies are assayed for or used in binding to DC receptors, such as CD40, and presenting HIV antigens. In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In a certain aspects a DC receptor fragment comprises substantially all of the extracellular domain of a protein which has at least 85% identity, at least 90% identity, at least 95% identity, or at least 97-99% identity, including all values and ranges there between, to a sequence selected over the length of the fragment sequence.

Also included in immunogenic compositions are fusion proteins composed of HIV antigens, or immunogenic fragments of HIV antigens (e.g., gp140). HIV antigens may be from any type (e.g. HIV-1, HIV-2), group (e.g. group M, group N, group O, or group P), sub-type or clade (e.g. clade A, B, C, D, F, G, H, J, K) or circulating recombinant form of HIV. Alternatively, embodiments also include individual fusion proteins of HIV proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197.

B. Antibodies and Antibody-Like Molecules

In certain aspects, one or more antibodies or antibody-like molecules (e.g., polypeptides comprising antibody CDR domains) may be obtained or produced which have a specificity for Dendritic cell receptor, e.g. CD40, LOX-1, DCIR or langerin. These antibodies may be used in the therapeutic applications described herein.

The term "antibody" refers to an intact immunoglobulin of any isotype, or a fragment thereof, that can complete with the intact antibody for specific binding to the target antigen, and includes chimeric, humanized, fully human, and bispecific antibodies. An intact antibody generally will comprise at least two full-length heavy chains and two full-length light chains, but in some instances may include fewer chains such as antibodies naturally occurring in camelids which may comprise only heavy chains. Antibodies according to the disclosure may be derived solely from a single source, or may be "chimeric," that is, different portions of the antibody may be derived from two different antibodies. For example, the CDR regions may be derived from a rat or murine source, while the framework region of the V region is derived from a different animal source, such as a human. The antibodies or binding fragments of the disclosure may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below.

The term "light chain" includes a full-length light chain and fragments thereof having sufficient variable region sequence to confer binding specificity. A full-length light chain includes a variable region domain (VL), and a constant region domain (CL). The variable region domain of the light chain is at the amino-terminus of the polypeptide. Light chains according to the disclosure include kappa chains and lambda chains.

The term "heavy chain" includes a full-length heavy chain and fragments thereof having sufficient variable region sequence to confer binding specificity. A full-length heavy chain includes a variable region domain (VH), and three constant region domains (CH1, CH2, and CH3). The VH domain is at the amino-terminus of the polypeptide, and the CH domains are at the carboxy-terminus, with the CH3 being closest to the —COOH end. Heavy chains according to the invention may be of any isotype, including IgG (including IgG1, IgG2, IgG3, and IgG4 subtypes), IgA (including IgA1 and IgA2 subtypes), IgM, and IgE.

The VH and VL regions can be further subdivided into regions of hypervariability, termed "complementarity determining regions" or "CDR", interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An amino acid sequence which is substantially the same as a heavy or light chain CDR exhibits a considerable amount or extent of sequence identity when compared to a reference sequence and contributes favorably to specific binding of an antigen bound specifically by an antibody having the reference sequence. Such identity is definitively known or recognizable as representing the amino acid sequence of the particular human monoclonal antibody. Substantially the same heavy and light chain CDR amino acid sequence can have, for example, minor modifications or conservative substitutions of amino acids so long as the ability to bind a particular antigen is maintained.

The term "CDR" or "complementarity determining region" means the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987) and additionally by MacCallum et al., J. Mol. Biol. 262:732-745 (1996), which are incorporated herein by reference, where the definitions include overlapping or subsets of amino acid residues when compared against each other. Nevertheless, application of either definition to refer to a CDR of an antibody or functional fragment thereof is intended to be within the scope of the term as defined and used herein. The exact amino acid residue numbers which encompass a particular CDR will vary depending on the structure of the CDR. Those skilled in the art can routinely determine which residues comprise a particular CDR given the variable region amino acid sequence of the antibody. Those skilled in the art can compare two or more antibody sequences by defining regions or individual amino acid positions of the respective sequences with the same CDR definition.

The term "antibody" includes both glycosylated and non-glycosylated immunoglobulins of any isotype or subclass or combination thereof, including human (including CDR-grafted antibodies), humanized, chimeric, multi-specific, monoclonal, polyclonal, and oligomers thereof, irrespective of whether such antibodies are produced, in whole or in part, via immunization, through recombinant technology, by way of in vitro synthetic means, or otherwise. Thus, the term "antibody" includes those that are prepared, expressed, created or isolated by recombinant means, such as (a) antibodies isolated from an animal (e.g., a mouse) that is transgenic for human immunoglobulin genes or a hybridoma prepared therefrom, (b) antibodies isolated from a host cell transfected to express the antibody, (c) antibodies isolated from a recombinant, combinatorial library, and (d) antibodies prepared, expressed, created or isolated by any other means that involve splicing of immunoglobulin gene sequences of two distinct species of animals. In certain embodiments, however, such antibodies can be subjected to in vitro mutagenesis (or, when an animal transgenic for human immunoglobulin sequences is used, in vivo somatic mutagenesis) and thus the amino acid sequences of the VH and VL regions of the antibodies are sequences that, while derived from and related to the germline VH and VL sequences of a particular species (e.g., human), may not naturally exist within that species' antibody germline repertoire in vivo.

The term "antigen-binding fragment" of an antibody means one or more fragments of an antibody that retain the ability to specifically bind to an antigen that is specifically bound by a reference antibody, as disclosed herein. An "antigen-binding fragment" of an antibody may include, for example, polypeptides comprising individual heavy or light chains and fragments thereof, such as VL, VH, and Fd regions (consisting of the VH and CH1 domains); monovalent fragments, such as Fv, Fab, and Fab' regions; bivalent fragments, such as F(ab')$_2$; single chain antibodies, such as single chain Fv (scFv) regions; Fc fragments; diabodies; maxibodies (bivalent scFv fused to the amino terminus of the Fc (CH2-CH3 domains)) and complementary determining region (CDR) domains. Such terms are described, for example, in Harlow and Lane, Antibodies: A Laboratory Manual, Cold Spring Harbor Laboratory, NY (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, 2d ed., Wiley-Liss, Inc. New York, N.Y. (1990), which are incorporated herein by reference.

The term "antigen-binding fragment" also includes, for example, fragments produced by protease digestion or reduction of a human monoclonal antibody and by recombinant DNA methods known to those skilled in the art. One skilled in the art knows that the exact boundaries of a fragment of a human monoclonal antibody can be variable, so long as the fragment maintains a functional activity. Using well-known recombinant methods, one skilled in the art can engineer a nucleic acid to express a functional fragment with any endpoints desired for a particular application. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., Science 242:423–426 (1988); and Huston et al., Proc. Natl. Acad. Sci. USA 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Such fragments include those obtained by amino-terminal and/or carboxy-terminal deletions, but where the remaining amino acid sequence is substantially identical to the corresponding positions in the naturally-occurring sequence deduced, for example, from a full-length cDNA sequence. Antigen-binding fragments also include fragments of an antibody which retain at least one (e.g., 1, 2, 3 or more) light chain sequences for a particular complementarity determining region (CDR) (e.g., at least one or more of CDR1, CDR2, and/or CDR3 from the heavy and/or light chain). Fusions of CDR containing sequences to an Fc region (or a CH2 or CH3 region thereof) are included within the scope of this definition including, for example, scFv fused, directly or indirectly, to an Fc region are included herein. An antigen-binding fragment is inclusive of, but not limited to, those derived from an antibody or fragment thereof (e.g., by enzymatic digestion or reduction of disulfide bonds), produced synthetically using recombinant methods, created via in vitro synthetic means (e.g., Merrifield resins), combinations thereof, or through other methods. Antigen-binding fragments may also comprise multiple fragments, such as CDR fragments, linked together synthetically, chemically, or otherwise, in the form of oligomers. Thus, antigen-binding fragments of the present invention include polypeptides produced by any number of methods which comprise at least one CDR from a VH or VL chain of the present invention (e.g., derived from monoclonal antibodies 480.12 and 994.1).

The term "VL fragment" means a fragment of the light chain of a monoclonal antibody which includes all or part of the light chain variable region, including the CDRs. A VL fragment can further include light chain constant region sequences.

The term "VH fragment" means a fragment of the heavy chain of a monoclonal antibody which includes all or part of the heavy chain variable region, including the CDRs. A VH fragment can further include heavy chain constant region sequences.

The term "Fd fragment" means a fragment of the heavy chain of a monoclonal antibody which includes all or part of the VH heavy chain variable region, including the CDRs. An Fd fragment can further include CH1 heavy chain constant region sequences.

An "Fc" region contains two heavy chain fragments comprising the CH1 and CH2 domains of an antibody. The two heavy chain fragments are held together by two or more disulfide bonds and by hydrophobic interactions of the CH3 domain.

The term "Fv fragment" means a monovalent antigen-binding fragment of a monoclonal antibody, including all or part of the variable regions of the heavy and light chains, and absent of the constant regions of the heavy and light chains. The variable regions of the heavy and light chains include, for example, the CDRs.

The term "Fab fragment" means a monovalent antigen-binding fragment of an antibody consisting of the VL, VH, CL and CH1 domains, which is larger than an Fv fragment. For example, a Fab fragment includes the variable regions, and all or part of the first constant domain of the heavy and light chains.

The term "Fab' fragment" means a monovalent antigen-binding fragment of a monoclonal antibody that is larger than a Fab fragment. For example, a Fab' fragment includes all of the light chain, all of the variable region of the heavy chain, and all or part of the first and second constant domains of the heavy chain.

The term "F(ab')$_2$ fragment" means a bivalent antigen-binding fragment of a monoclonal antibody comprising two Fab fragments linked by a disulfide bridge at the hinge region. An F(ab')$_2$ fragment includes, for example, all or part of the variable regions of two heavy chains and two light chains, and can further include all or part of the first constant domains of two heavy chains and two light chains.

"Single-chain antibodies" are Fv molecules in which the heavy and light chain variable regions have been connected by a flexible linker to form a single polypeptide chain, which forms an antigen-binding fragment. Single chain antibodies are discussed in detail in International Patent Application Publication No. WO 88/01649 and U.S. Pat. Nos. 4,946,778 and 5,260,203, the disclosures of which are herein incorporated by reference.

A "domain antibody" is an antigen-binding fragment containing only the variable region of a heavy chain or the variable region of a light chain. In some instances, two or more VH regions are covalently joined with a peptide linker to create a bivalent domain antibody. The two VH regions of a bivalent domain antibody may target the same or different antigens.

The term "bivalent antibody" means an antibody that comprises two antigen binding sites. In some instances, the two binding sites have the same antigen specificities. However, bivalent antibodies may be bispecific.

The term "bispecific antibody" means an antibody that binds to two or more distinct epitopes. For example, the antibody may bind to, or interact with, (a) a cell surface antigen and (b) an Fc receptor on the surface of an effector cell. The term "multispecific antibody" or "heterospecific antibody" means an antibody that binds to more than two distinct epitopes. For example, the antibody may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific antibodies or antigen-binding fragments thereof which are directed to certain epitopes and to other targets, such as Fc receptors on effector cells. Bispecific antibodies are a species of multispecific antibody and may be produced by a variety of methods including, but not limited to, fusion of hybridomas or linking of Fab' fragments. See, e.g., Songsivilai and Lachmann, Clin. Exp. Immunol. 79:315 (1990); Kostelny et al., J. Immunol. 148: 1547 (1992). The two binding sites of a bispecific antibody will bind to two different epitopes, which may reside on the same or different protein targets. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Hollinger et al., Proc Natl. Acad. Sci. USA 90:6444-6448 (1993); Polijak et al., Structure 2:1121-1123 (1994).

The term "monoclonal antibody" or "mAb," as used herein, refers to an antibody obtained from a population of substantially homogeneous antibodies, e.g., the individual antibodies comprising the population are identical except for possible naturally occurring mutations that may be present in minor amounts. In contrast to polyclonal antibody preparations that typically include different antibodies against different determinants (epitopes), each monoclonal antibody is directed against a single determinant on the antigen. The term is not limited regarding the species or source of the antibody, nor is it intended to be limited by the manner in which it is made. The term encompasses whole immunoglobulins as well as fragments such as Fab, F(ab')$_2$, Fv, and other fragments, as well as chimeric and humanized homogeneous antibody populations, that exhibit immunological binding properties of the parent monoclonal antibody molecule.

The term "mouse monoclonal antibody" means a monoclonal antibody, as defined above, produced by immunizing a mouse, with an antigen of interest. A "mouse monoclonal antibody" is produced using conventional methods well known in the art, from mouse-mouse hybridomas, described more fully below.

The term "rabbit monoclonal antibody" as used herein means a monoclonal antibody, as defined above, produced by immunizing a rabbit with an antigen of interest. A "rabbit monoclonal antibody" can be produced using rabbit-rabbit hybridomas (e.g., fusions between an antibody-producing cell from the immunized rabbit with an immortalized cell from a rabbit), rabbit-mouse hybridomas (e.g., fusions between an antibody-producing cell from the immunized rabbit with an immortalized cell from a mouse), and the like.

The term "human monoclonal antibody" means a monoclonal antibody with substantially human CDR amino acid sequences produced, for example, by recombinant methods, by lymphocytes or by hybridoma cells.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851 (1984).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or nonhuman primate having the desired specificity, affinity, and capacity. In some instances, framework region (FR) residues of the immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522 (1986); Riechmann et al., Nature 332:323 (1988); Presta, Curr. Op. Struct. Biol. 2:593 (1992); Vaswani and Hamilton, Ann. Allergy, Asthma and Immunol. 1:105 (1998); Harris, Biochem. Soc. Transactions 23; 1035 (1995); Hurle and Gross, Curr. Op. Biotech. 5:428 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding regions.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., Bio/Technology 10:779 (1992) describes affinity maturation by VH and VL domain shuffling. Random mutagenesis of CDR and/or framework residues is described by: Barbas et al., Proc. Natl. Acad. Sci. USA 91:3809 (1994); Schier et al., Gene 169:147 (1995); Yelton et al., J. Immunol. 155:1994 (1995); Jackson et al., J. Immunol. 154:3310 (1995); and Hawkins et al., J. Mol. Biol. 226:889 (1992).

The term "antigen" refers to a molecule or a portion of a molecule capable of being bound by a selective binding agent, such as an antibody, and additionally capable of being used in an animal to produce antibodies capable of binding to that antigen. An antigen may possess one or more epitopes that are capable of interacting with different antibodies.

The term "epitope" includes any determinant capable of binding with high affinity to an immunoglobulin or to a T-cell receptor. An epitope is a region of an antigen that is bound by an antibody that specifically targets that antigen, and when the antigen is a protein, includes specific amino acids that directly contact the antibody. Most often, epitopes reside on proteins, but in some instances, may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. Proc. Natl. Acad. Sci. USA 81:3998–4002 (1984); Geysen et al. Proc. Natl. Acad. Sci. USA 82:178-182 (1985); Geysen et al. Molec. Immunol. 23:709-715 (1986). Similarly, conformational epitopes are readily identified by determining spatial conformation of amino acids such as by, e.g., x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., Proc. Natl. Acad. Sci. USA 78:3824-3828 (1981) for determining antigenicity profiles, and the Kyte-Doolittle technique, Kyte et al., J. Mol. Biol. 157:105-132 (1982) for hydropathy plots.

An antibody of the disclosure is said to "specifically bind" its target antigen when the dissociation constant ($K_D$) is $\leq 10^{-8}$ M. The antibody specifically binds antigen with "high affinity" when the $K_D$ is $\leq 5\times 10^{-9}$ M, and with "very high affinity" when the $K_D$ is $\leq 5\times 10^{-10}$ M. In one embodiment of the invention, the antibody has a $K_D$ of $\leq 10^{-9}$ M and an off-rate ($K_D$) of about $1\times 10^{-4}$/sec. In one embodiment of the invention, the off-rate is $<1\times 10^{-5}$/sec.

It is understood that the antibodies of the present disclosure may be modified, such that they are substantially identical to the antibody polypeptide sequences, or fragments thereof, and still bind the epitopes of the disclosure. Polypeptide sequences are "substantially identical" when optimally aligned using such programs as GAP or BESTFIT using default gap weights, they share at least 80% sequence identity, at least 90% sequence identity, at least 95% sequence identity, at least 96% sequence identity, at least 97% sequence identity, at least 98% sequence identity, or at least 99% sequence identity.

As discussed herein, minor variations in the amino acid sequences of antibodies or antigen-binding regions thereof are contemplated as being encompassed by the present disclosure, providing that the variations in the amino acid sequence maintain at least 75%, more preferably at least 80%, at least 90%, at least 95%, at least 96%, at least 97%, at least 98% and most preferably at least 99% sequence identity. In particular, conservative amino acid replacements are contemplated. Conservative replacements are those that take place within a family of amino acids that are related in their side chains. Genetically encoded amino acids are generally divided into families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). More preferred families are: (1) aliphatic-hydroxy (serine, threonine); (2) amide-containing (asparagine, glutamine); (3) aliphatic (alanine, valine, leucine, isoleucine); and (4) aromatic (phenylalanine, tryptophan). For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al., Science 253:164 (1991).

The antibodies of the present disclosure may also be generated using peptide analogs of the epitopic determinants disclosed herein, which analogs may consist of non-peptide compounds having properties analogous to those of the template peptide. These types of non-peptide compound are termed "peptide mimetics" or "peptidomimetics". Fauchere, J. Adv. Drug Res. 15:29 (1986); Veber and Freidinger TINS p. 392 (1985); and Evans et al., J. Med. Chem. 30:1229 (1987).

"Mini-antibodies" or "minibodies" are also contemplated for use with embodiments. Minibodies are sFv polypeptide chains which include oligomerization domains at their C-termini, separated from the sFv by a hinge region (Pack, et al., 1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in embodiments. Liu et al., 2003 describe "antibody like binding peptidomimetics" (ABiPs), which are peptides that act as pared-down antibodies and have certain advantages of longer serum half-life as well as less cumbersome synthesis methods.

Alternative scaffolds for antigen binding peptides, such as CDRs are also available and can be used to generate DC receptor-binding molecules in accordance with the embodiments. Generally, a person skilled in the art knows how to determine the type of protein scaffold on which to graft at least one of the CDRs arising from the original antibody. More particularly, it is known that to be selected such scaffolds must meet the greatest number of criteria as follows (Skerra, 2000): good phylogenetic conservation; known three-dimensional structure (as, for example, by crystallography, NMR spectroscopy or any other technique known to a person skilled in the art); small size; few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra, 2001), protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat". For example, anticalins or lipocalin derivatives are a type of binding proteins that have affinities and specificities for various target molecules and can be used as DC receptor-binding molecules. Such proteins are described in US Patent Publication Nos. 20100285564, 20060058510, 20060088908, 20050106660, and PCT Publication No. WO2006/056464, incorporated herein by reference.

Scaffolds derived from toxins such as, for example, toxins from scorpions, insects, plants, mollusks, etc., and the protein inhibitors of neuronal NO synthase (PIN) may also be used in certain aspects.

Chimeric and humanized antibodies based upon the foregoing sequences are also encompassed by the current disclosure. Monoclonal antibodies for use as therapeutic agents may be modified in various ways prior to use. One example is a "chimeric" antibody, which is an antibody composed of protein segments from different antibodies that are covalently joined to produce functional immunoglobulin light or heavy chains or antigen-binding fragments thereof. Generally, a portion of the heavy chain and/or light chain is identical with, or homologous to, a corresponding sequence in antibodies derived from a particular species or belonging to a particular antibody class or subclass, while the remainder of the chain(s) is/are identical or homologous to a corresponding sequence in antibodies derived from another species or belonging to another antibody class or subclass. For methods relating to chimeric antibodies, see, for example, U.S. Pat. No. 4,816,567; and Morrison et al. Proc. Natl. Acad. Sci. USA 81:6851-6855 (1985), which are hereby incorporated by reference. CDR grafting is described, for example, in U.S. Pat. Nos. 6,180,370, 5,693,762, 5,693,761, 5,585,089, and 5,530,101, which are all hereby incorporated by reference for all purposes.

Generally, the goal of making a chimeric antibody is to create a chimera in which the number of amino acids from the intended patent species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the V region or selected CDRs from a rodent antibody often are grafted into a human antibody, replacing the naturally-occurring V regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody or corresponding isotype. Preferably, humanized antibodies contain minimal sequence derived from non-human immunoglobulin sequences. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205. In some instances, framework residues of the human immunoglobulin are replaced by corresponding non-human residues (see, for example, U.S. Pat. Nos. 5,585,089; 5,693,761; 5,693,762). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-525 (1986); Riechmann et al., Nature 332:323-329 (1988); and Presta, Curr. Op. Struct. Biol. 2:593-596 (1992); Verhoeyen et al., Science 239:1534-36 (1988)).

In one aspect of the disclosure, the CDRs of the light and heavy chain variable regions of the antibodies provided herein are grafted to framework regions (FRs) from antibodies from the same, or a different, phylogenetic species. To create consensus human FRs, FRs from several human heavy chain or light chain amino acid sequences may be aligned to identify a consensus amino acid sequence. In one aspect of the invention, rare amino acids in the FRs of the heavy and light chains of the antibody are not replaced, while the rest of the FR amino acids are replaced. A "rare amino acid" is a specific amino acid that is in a position in which this particular amino acid is not usually found in an FR. Alternatively, the grafted variable regions from the antibody may be used with a constant region that is different from the constant region of antibody. In other embodiments of the disclosure, the grafted variable regions are part of a single chain Fv antibody.

In certain embodiments, constant regions from species other than human can be used along with the human variable region(s) to produce hybrid antibodies.

Also encompassed are xenogeneic or modified antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. No. 5,939,598.

Fully human antibodies are also provided. Methods are available for making fully human antibodies specific for a given antigen without exposing human beings to the antigen ("fully human antibodies"). One means for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derivatized mAbs to humans as therapeutic agents.

In one embodiment, human antibodies may be produced in a non-human transgenic animal, e.g., a transgenic mouse capable of producing multiple isotypes of human antibodies to CD40 (e.g., IgG, IgA, and/or IgE) by undergoing V-D-J recombination and isotype switching. Accordingly, aspects of the disclosure include not only antibodies, antibody fragments, and pharmaceutical compositions thereof, but also non-human transgenic animals, B-cells, host cells, and hybridomas which produce the antibodies. The present disclosure further encompasses pharmaceutical preparations containing the antibodies, and methods of treating physiological disorders, e.g., HIV, by administering the antibodies of the present disclosure.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, for example, Jakobovits et al., Proc. Natl. Acad. Sci. USA 90:2551-2555 (1993); Jakobovits et al., Nature 362: 255-258 (1993); Bruggermann et al., Year in Immunol. 7:33 (1993). In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then crossbred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, International Patent Application Publication Nos. WO 96/33735 and WO 94/02602, which are hereby incorporated by reference in their entirety. Additional methods relating to transgenic mice for making human antibodies are described in U.S. Pat. Nos. 5,545,807; 6,713,610; 6,673,986; 6,162,963; 6,300,129; 6,255,458; 5,877,397; 5,874,299 and 5,545,806; in International Patent Application Publication Nos. WO 91/10741 and WO 90/04036; and in European Patent Nos. EP 546073B1 and EP 546073A1, all of which are hereby incorporated by reference in their entirety for all purposes.

The transgenic mice described above, referred to herein as "HuMAb" mice, contain a human immunoglobulin gene minilocus that encodes unrearranged human heavy (μ and γ) and κ light chain immunoglobulin sequences, together with targeted mutations that inactivate the endogenous μ and κ chain loci (Lonberg et al., Nature 368:856-859 (1994)). Accordingly, the mice exhibit reduced expression of mouse IgM or κ chains and in response to immunization, the introduced human heavy and light chain transgenes undergo class switching and somatic mutation to generate high affinity human IgG kappa monoclonal antibodies (Lonberg et al., supra; Lonberg and Huszar, Intern. Ref. Immunol. 13:65-93 (1995); Harding and Lonberg, Ann. N.Y. Acad. Sci. 764:536-546 (1995)). The preparation of HuMAb mice is described in detail in Taylor et al., Nucl. Acids Res. 20:6287-6295 (1992); Chen et al., Int. Immunol. 5:647-656 (1993); Tuaillon et al., J. Immunol. 152:2912-2920 (1994); Lonberg et al., supra; Lonberg, Handbook of Exp. Pharmacol. 113:49-101 (1994); Taylor et al., Int. Immunol. 6:579-591 (1994); Lonberg and Huszar, Intern. Ref. Immunol. 13:65-93 (1995); Harding and Lonberg, Ann. N.Y. Acad. Sci. 764:536-546 (1995); Fishwild et al., Nat. Biotechnol. 14:845-851 (1996); the foregoing references are herein incorporated by reference in their entirety for all purposes. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; as well as International Patent Application Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., Nat. Genetics 15:146-156 (1997), which are herein incorporated by reference.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., J. Mol. Biol. 227:381 (1991); and Marks et al., J. Mol. Biol. 222:581 (1991)). Phage-display techniques mimic immune selection through the display of antibody repertoires on the surface of filamentous bacteriophage, and subsequent selection of phage by their binding to an antigen of choice. One such technique is described in International Patent Application Publication No. WO 99/10494 (herein incorporated by reference), which describes the isolation of high affinity and functional agonistic antibodies for MPL- and msk-receptors using such an approach.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three-dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for CD40 binding, thus yielding information gathered from such routine experiments, one skilled in the art can readily determine the amino acid positions where further substitutions should be avoided either alone or in combination with other mutations.

In some embodiments of the disclosure, amino acid substitutions are made that: (1) reduce susceptibility to proteolysis, (2) reduce susceptibility to oxidation, (3) alter binding affinity for forming protein complexes, (4) alter ligand or antigen binding affinities, and/or (5) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts. In such embodiments, conservative amino acid substitutions can be used that do not substantially change the structural characteristics of the parent sequence (e.g., one or more replacement amino acids that do not disrupt the secondary structure that characterizes the parent or native antibody). Examples of art-recognized polypeptide secondary and tertiary structures are described in Proteins, Structures and Molecular Principles (Creighton, Ed.), 1984, W.H. New York: Freeman and Company; Introduction to Protein Structure (Brandon and Tooze, eds.), 1991 New York: Garland Publishing; and Thornton et al., Nature 354:105 (1991), each of which is incorporated herein by reference in its entirety for all purposes.

The disclosure also encompasses glycosylation variants of the antibodies wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked glycosylation sites are created. Antibodies typically have a N-linked glycosylation site in the Fc region.

Additional preferred antibody variants include cysteine variants wherein one or more cysteine residues in the parent or native amino acid sequence are deleted from or substituted with another amino acid (e.g., serine). Cysteine variants are useful, inter alia, when antibodies must be refolded into a biologically active conformation. Cysteine variants may have fewer cysteine residues than the native antibody, and typically have an even number to minimize interactions resulting from unpaired cysteines.

Derivatives of the antibodies and antigen binding fragments that are described herein are also provided. The derivatized antibody or fragment may comprise any molecule or substance that imparts a desired property to the antibody or fragment, such as increased half-life in a particular use. The derivatized antibody can comprise, for example, a detectable (or labeling) moiety (e.g., a radioactive, colorimetric, antigenic or enzymatic molecule, a detectable bead [such as a magnetic or electrodense (e.g., gold) bead], or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art.

In certain embodiments, a polypeptide that specifically binds to DC receptors is able to bind a DC receptor on the surface of the cells and present an HIV antigen that allows the generation of a robust immune response. Moreover, in some embodiments, the polypeptide that is used can provided protective immunity against HIV.

1. Methods for Generating Antibodies

Methods for generating antibodies (e.g., monoclonal antibodies and/or monoclonal antibodies) are known in the art. Briefly, a polyclonal antibody is prepared by immunizing an animal with an antigenic polypeptide, such as a CD40 polypeptide or a portion thereof in accordance with embodiments and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include any acceptable immunostimulatory compound, such as cytokines, chemokines, cofactors, toxins, plasmodia, synthetic compositions or vectors encoding such adjuvants.

Adjuvants that may be used in accordance with embodiments include, but are not limited to, IL-1, IL-2, IL-4, IL-7, IL-12, -interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary adjuvants may include complete Freund's adjuvant (a non-specific stimulator of the immune response containing killed *Mycobacterium tuberculosis*), incomplete Freund's adjuvants and/or aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, Pennsylvania); low-dose Cyclophosphamide (CYP; 300 mg/m2) (Johnson/Mead, New Jersey), cytokines such as -interferon, IL-2, or IL-12 or genes encoding proteins involved in immune helper functions, such as B-7.

The amount of immunogen composition used in the production of antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of antibodies may be monitored by sampling blood of the immunized animal at various points following immunization.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. In some embodiments, Rodents such as mice and rats are used in generating monoclonal antibodies. In some embodiments, rabbit, sheep or frog cells are used in generating monoclonal antibodies. The use of rats is well known and may provide certain advantages (Goding, 1986, pp. 60 61). Mice (e.g., BALB/c mice) are routinely used and generally give a high percentage of stable fusions.

MAbs produced by either means may be further purified, if desired, using filtration, centrifugation and various chromatographic methods such as HPLC or affinity chromatography. Fragments of the monoclonal antibodies can be obtained from the monoclonal antibodies so produced by methods which include digestion with enzymes, such as pepsin or papain, and/or by cleavage of disulfide bonds by chemical reduction. Alternatively, monoclonal antibody fragments can be synthesized using an automated peptide synthesizer.

It is also contemplated that a molecular cloning approach may be used to generate monoclonal antibodies. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 104 times as many antibodies can be produced and screened in a single round, and that new specificities are generated by H and L chain combination which further increases the chance of finding appropriate antibodies.

Another embodiment concerns producing antibodies, for example, as is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments can be synthesized using an automated peptide synthesizer, or by expression of full-length gene or of gene fragments in E. coli.

It is further contemplated that monoclonal antibodies may be further screened or optimized for properties relating to specificity, avidity, half-life, immunogenicity, binding association, binding disassociation, or overall functional properties relative to being a treatment for infection. Thus, it is contemplated that monoclonal antibodies may have 1, 2, 3, 4, 5, 6, or more alterations in the amino acid sequence of 1, 2, 3, 4, 5, or 6 CDRs of monoclonal antibodies or humanized antibodies provided herein. It is contemplated that the amino acid in position 1, 2, 3, 4, 5, 6, 7, 8, 9, or 10 of CDR1, CDR2, CDR3, CDR4, CDR5, or CDR6 of the VJ or VDJ region of the light or heavy variable region of antibodies may have an insertion, deletion, or substitution with a conserved or non-conserved amino acid. Such amino acids that can either be substituted or constitute the substitution are disclosed above.

In some embodiments, fragments of a whole antibody can perform the function of binding antigens. Examples of binding fragments are (i) the Fab fragment constituted with the VL, VH, CL and CHl domains; (ii) the Fd fragment consisting of the VH and CHl domains; (iii) the Fv fragment constituted with the VL and VH domains of a single antibody; (iv) the dAb fragment (Ward, 1989; McCafferty et al., 1990; Holt et al., 2003), which is constituted with a VH or a VL domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988; Huston et al., 1988); (viii) bispecific single chain Fv dimers (PCT/US92/09965) and (ix) "diabodies", multivalent or multispecific fragments constructed by gene fusion (WO94/13804; Holliger et al., 1993). Fv, scFv or diabody molecules may be stabilized by the incorporation of disulphide bridges linking the VH and VL domains (Reiter et al., 1996). Minibodies comprising a scFv joined to a CH3 domain may also be made (Hu et al. 1996). The citations in this paragraph are all incorporated by reference.

Antibodies also include bispecific antibodies. Bispecific or bifunctional antibodies form a second generation of monoclonal antibodies in which two different variable regions are combined in the same molecule (Holliger & Winter, 1999). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger et al, 1993), e.g. prepared chemically or from hybrid hybridomas, or may be any of the bispecific antibody fragments mentioned above. These antibodies can be obtained by chemical methods (Glennie et al., 1987; Repp et al., 1995) or somatic methods (Staerz & Bevan, 1986) but likewise by genetic engineering techniques which allow the heterodimerization to be forced and thus facilitate the process of purification of the antibody sought (Merchand et al., 1998). Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction. The citations in this paragraph are all incorporated by reference.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against SpA, then a library can be made where the other arm is varied and an antibody of appropriate specificity selected. Bispecific whole antibodies may be made by alternative engineering methods as described in Ridgeway et al., 1996), which is hereby incorporated by reference.

C. Antibody and Polypeptide Conjugates

Embodiments provide antibodies and antibody-like molecules against DC receptor, e.g. CD40, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, therapeutic enzymes, antibiotics, radio-labeled nucleotides and the like. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Antibody conjugates include those intended primarily for use in vitro, where the antibody is linked to a secondary binding ligand and/or to an enzyme (an enzyme tag) that will generate a colored product upon contact with a chromogenic substrate. Examples of suitable enzymes include, but are not limited to, urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277, 437; 4,275,149 and 4,366,241; each incorporated herein by reference.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In some embodiments anti-CD40 antibodies are used to target HIV antigens to dendritic cells. Compositions and methods for the expression, secretion and use of anti-CD40 antibodies as vaccines and antigen delivery vectors with one linked antigenic peptides are described in WO 2010/104761; all methods disclosed are incorporated herein by reference.

In certain aspects, peptide linkers are used to link a dendritic cell specific antibodies and HIV antigens to be presented. Peptide linkers may incorporate glycosylation sites or introduce secondary structure. Additionally these linkers increase the efficiency of expression or stability of the fusion protein and as a result the efficiency of antigen presentation to a dendritic cell. Such linkers may include the flexV1, f1, f2, and/or f3 linkers. These examples and others are discussed in WO 2010/104747, the contents of which are incorporated herein by reference.

D. Immunostimulants

In some embodiments an immunostimulant is administered in combination with the antibody-antigen fusion protein. The term "immunostimulant" as used herein refers to a compound that can stimulate an immune response in a subject, and may include an adjuvant. In some embodiments, the immunostimulant is directly fused to the CD40 specific antibody. In either case, the immunostimulant may enhance the efficacy of the vaccine. In certain aspects the immunostimulant may be a toll-like receptor (TLR) agonist. TLR agonists comprise flagellins from *Salmonella enterica* or *Vibrio cholerae*. TLR agonists may be specific for certain TLR classes (i.e., TLR5, TLR7 or TLR9 agonists) and may be presented in any combination or as any modification.

Examples of such immune adjuvants are described in WO 2012/021834, the contents of which are incorporated herein by reference.

In some embodiments, an immunostimulant is an agent that does not constitute a specific antigen, but can boost the strength and longevity of an immune response to an antigen. Such immunostimulants may include, but are not limited to stimulators of pattern recognition receptors, such as Toll-like receptors, RIG-1 and NOD-like receptors (NLR), mineral salts, such as alum, alum combined with monphosphoryl lipid (MPL) A of Enterobacteria, such as *Escherihia coli, Salmonella minnesota, Salmonella typhimurium,* or *Shigella flexneri* or specifically with MPL.RTM. (ASO4), MPL A of above-mentioned bacteria separately, saponins, such as QS-21, Quil-A, ISCOMs, ISCOMATRIX, emulsions such as MF59, Montanide, ISA 51 and ISA 720, AS02 (QS21+squalene+MPL.), liposomes and liposomal formulations such as AS01, synthesized or specifically prepared microparticles and microcarriers such as bacteria-derived outer membrane vesicles (OMV) of *N. gonorrheae, Chlamydia trachomatis* and others, or chitosan particles, depot-forming agents, such as Pluronic block co-polymers, specifically modified or prepared peptides, such as muramyl dipeptide, aminoalkyl glucosaminide 4-phosphates, such as RC529, or proteins, such as bacterial toxoids or toxin fragments.

In some embodiments, the immunostimulant comprises an agonist for pattern recognition receptors (PRR), including, but not limited to Toll-Like Receptors (TLRs), specifically TLRs 2, 3, 4, 5, 7, 8, 9 and/or combinations thereof. In some embodiments, additional agents comprise agonists for Toll-Like Receptors 3, agonists for Toll-Like Receptors 7 and 8, or agonists for Toll-Like Receptor 9. In some embodiments, the immunostimulants comprise imidazoquinolines; such as R848; adenine derivatives, such as those disclosed in U.S. Pat. No. 6,329,381, U.S. Published Patent Application 2010/0075995, or WO 2010/018132; immunostimulatory DNA; or immunostimulatory RNA. In some embodiments, the immunostimulant may comprise immunostimulatory RNA molecules, such as but not limited to dsRNA, poly I:C, poly I:poly C12U (available as Ampligen.®, both poly I:C and poly I:polyC12U being known as TLR3 stimulants), polyICLC (such as Hiltonol), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some embodiments, an additional agent may be a TLR-4 agonist, such as bacterial lipopolysaccharide (LPS), VSV-G, and/or HMGB-1. In some embodiments, additional agents may comprise TLR-5 agonists, such as flagellin, or portions or derivatives thereof, including but not limited to those disclosed in U.S. Pat. Nos. 6,130,082, 6,585,980, and 7,192,725.

In some embodiments, the immunostimulant may be proinflammatory stimuli released from necrotic cells (e.g., urate crystals). In some embodiments, the immunostimulant may be activated components of the complement cascade (e.g., CD21, CD35, etc.). In some embodiments, the immunostimulant may be activated components of immune complexes. Immunostimulants also include complement receptor agonists, such as a molecule that binds to CD21 or CD35. In some embodiments, the complement receptor agonist induces endogenous complement opsonization of the synthetic nanocarrier. In some embodiments, immunostimulants are cytokines, which are small proteins or biological factors (in the range of 5 kD-20 kD) that are released by cells and have specific effects on cell-cell interaction, communication and behavior of other cells. In some embodiments, the cytokine receptor agonist is a small molecule, antibody, fusion protein, or aptamer.

III. Methods of Treatment

As discussed above, the compositions and methods of using these compositions can treat a subject (e.g., prevent an HIV infection or evoke a robust immune response to HIV) having, suspected of having, or at risk of developing an infection or related disease, particularly those related to HIV.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the invention in a recipient patient. Treatment or therapy can be an active immune response induced by administration of immunogen or a passive therapy effected by administration of antibody, antibody containing material, or primed T-cells.

For purposes of this specification and the accompanying claims the terms "epitope," "antigen," "Ag," and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include those methods described in Epitope Mapping Protocols (1996). T cells recognize continuous epitopes of about nine amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject. As used herein and in the claims, the terms "antibody" or "immunoglobulin" are used interchangeably.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

In one embodiment a method includes treatment for a disease or condition caused by a HIV pathogen. In certain aspects embodiments include methods of treatment of HIV infection, such as an infection acquired from an HIV positive individual. In some embodiments, the treatment is administered in the presence of HIV antigens. Furthermore, in some examples, treatment comprises administration of other agents commonly used against viral infection, such as one or more antiviral or antiretroviral compounds.

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

The manner of application may be varied widely. Any of the conventional methods for administration of a polypeptide therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, 12 twelve week intervals, including all ranges there between.

A. Combination Therapy

The compositions and related methods, particularly administration of an antibody that binds a DC receptor, e.g. CD40, and delivers an HIV antigen or a peptide to a patient/subject, may also be used in combination with the administration of traditional anti-retroviral therapies. These include, but are not limited to, entry inhibitors, CCR5 receptor antagonists, nucleoside reverse transcriptase inhibitors, nucleotide reverse transcriptase inhibitors, non-nucleoside reverse transcriptase inhibitors, protease inhibitors, integrase inhibitors and maturation inhibitors.

In one aspect, it is contemplated that a therapy is used in conjunction with antiviral or anti-retroviral treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In yet another aspect, a vaccine may be administered as part of a prime/boost strategy. A priming vaccine dose can be administered using an antibody fused to an HIV antigen in any of the embodiments described herein. A vaccine boost can be administered through the use of a second vaccine, either of the same type or from a different type of vaccine. Examples of such different vaccines include DNA vaccines (naked or not) or a recombinant poxvirus. A recombinant pox virus can be selected from the group comprising NYVAC, NYVAC-KC, ALVAC and MVA virus. In some embodiments, the second vaccine, such as a pox virus vaccine or a DNA vaccine is used in a priming dose and the vaccines of the disclosure comprising the anti-DCR-HIV antigen fusion proteins, e.g the anti-CD40-HIV antigen fusion proteins, are administered in one or more booster doses. In one embodiment, the DNA vaccine is selected from DNA-HIV-PT 123 DNA vaccine.

DNA-HIV-PT123 HIV vaccine may be presented as a solution for injection at a total DNA concentration of approximately 4.0 mg/ml in PBS buffer. The vaccine is an equi-mass mixture of three different recombinant plasmids expressing clade C 96ZM651 gp140, 96ZM651 Gag, and 97CD54 Pol-Nef. The DNA plasmid backbone was developed by the Vaccine Research Center (VRC), NIAID. The CMV/R promoter consists of the translational enhancer region of the CMV immediate early region 1 enhancer substituted with the 5'-untranslated human T cell leukemia virus type 1 (HTLV-1) R-U5 region of the long terminal repeat (LTR) to optimize gene expression. Other elements of the plasmid include a bovine growth hormone polyadenylation signal termination sequence (Tbgh) and a kanamycin resistance cassette (Kan). Enhancements made to the inserts include RNA and codon optimization, RNA secondary structure modulation, splice sites removal, TCF binding sites removal, and increasing the GC content.

The second vaccine may comprise additional HIV antigens apart from the Env antigens that may be used in the first vaccine. It is also contemplated that the second vaccine may comprise an HIV protein such as an env protein plus an adjuvant either directly linked or administered independently.

Various combinations of therapy may be employed, for example antiviral or antiretroviral therapy is "A" and an antibody vaccine that comprises an antibody that binds a DC receptor and delivers an HIV antigen or a peptide or consensus peptide thereof is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the antibody compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

B. General Pharmaceutical Compositions

In some embodiments, pharmaceutical compositions are administered to a subject. Different aspects may involve administering an effective amount of a composition to a subject. In some embodiments, an antibody that binds DC receptor, e.g. CD40, and delivers an HIV antigen or a peptide or consensus peptide thereof may be administered to the patient to protect against or treat infection by one or more HIV subtypes. Alternatively, an expression vector encoding one or more such antibodies or polypeptides or peptides may be given to a patient as a preventative treatment. Additionally, such compositions can be administered in combination with an antibiotic. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds can be formulated for parenteral administration, e.g., formulated for injection via the mucosal, intravenous, intradermal, intramuscular, subcutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

IV. Listing of Sequences

| SEQ ID NO | Brief Description | SEQUENCE |
|---|---|---|
| 1 | Amino acid sequence of Env gp140 | NLWVTVYYGVPVWKEAKTTLFCASDAKSYEKEVHNVWATHACVP TDPNPQEIVLGNVTENFNMWKNDMVDQMHEDIISLWDQSLKPCV KLTPLCVTLNCTEVNVTRNVNNSVVNNTTNVNNSMNGDMKNCSF NITTELKDKKKNVYALFYKLDIVSLNETDDSETGNSSKYYRLIN CNTSALTQACPKVSFDPIPIHYCAPAGYAILKCNNKTFNGTGPC HNVSTVQCTHGIKPVVSTQLLLNGSLAEEGIIIRSENLTNNVKT IIVHLNRSIEIVCVRPNNNTRQSIRIGPGQTFYATGDIIGDIRQ |

-continued

IV. Listing of Sequences

| SEQ ID NO | Brief Description | SEQUENCE |
|---|---|---|
| | | AHCNISRTNWTKTLREVRNKLREHFPNKNITFKPSSGGDLEITT<br>HSFNCRGEFFYCNTSGLFSINYTENNTDGTPITLPCRIRQIINM<br>WQEVGRAMYAPPIEGNIACKSDITGLLLVRDGGSTNDSTNNNTE<br>IFRPAGGDMRDNWRSELYKYKVVEIKPLGIAPTEAKRRVVEREK<br>RAVGIGAVFLGFLGAAGSTMGAASITLTAQARQVLSGIVQQQSN<br>LLRAIEAQQHLLQLTVWGIKQLQTRVLAIERYLKDQQLLGLWGC<br>SGKLICTTAVPWNISWSNKSKTDIWDNMTWMQWDREISNYTNTI<br>YRLLEDSQSQQEQNEKDLLALDSWNNLWNWFDITKWLWYIK |
| 2 | Amino acid sequence of FlexV1 | QTPTNTISVTPTNNSTPTNNSNPKPNP |
| 3 | Amino acid sequence of JS-FlexV1-JS-Env gp140-JS; JS sites are lower case; FlexV1 is in italics; Env gp140 is underlined | as*QTPTNTISVTPTNNSTPTNNSNPKPNP*asNLWVTVYYGVPVW<br>KEAKTTLFCASDAKSYEKEVHNVWATHACVPTDPNPQEIVLGNV<br>TENFNMWKNDMVDQMHEDIISLWDQSLKPCVKLTPLCVTLNCTE<br>VNVTRNVNNSVVNNTTNVNNSMNGDMKNCSFNITTELKDKKKNV<br>YALFYKLDIVSLNETDDSETGNSSKYYRLINCNTSALTQACPKV<br>SFDPIPIHYCAPAGYAILKCNNKTFNGTGPCHNVSTVQCTHGIK<br>PVVSTQLLLNGSLAEEGIIIRSENLTNNVKTIIVHLNRSIEIVC<br>VRPNNNTRQSIRIGPGQTFYATGDIIGDIRQAHCNISRTNWTKT<br>LREVRNKLREHFPNKNITFKPSSGGDLEITTHSFNCRGEFFYCN<br>TSGLFSINYTENNTDGTPITLPCRIRQIINMWQEVGRAMYAPPI<br>EGNIACKSDITGLLLVRDGGSTNDSTNNNTEIFRPAGGDMRDNW<br>RSELYKYKVVEIKPLGIAPTEAKRRVVEREKRAVGIGAVFLGFL<br>GAAGSTMGAASITLTAQARQVLSGIVQQQSNLLRAIEAQQHLLQ<br>LTVWGIKQLQTRVLAIERYLKDQQLLGLWGCSGKLICTTAVPWN<br>ISWSNKSKTDIWDNMTWMQWDREISNYTNTIYRLLEDSQSQQEQ<br>NEKDLLALDSWNNLWNWFDITKWLWYIKas |
| 4 | Amino acid sequence of humanized heavy chain of anti-CD40 antibody 12E12 (hAnti-CD40VH3-LV-hIgG4HC) | EVQLVESGGGLVQPGGSLKLSCATSGFTFSDYYMYWVRQAPGKG<br>LEWVAYINSGGGSTYYPDTVKGRFTISRDNAKNTLYLQMNSLRA<br>EDTAVYYCARRGLPFHAMDYWGQGTLVTVSSASTKGPSVFPLAP<br>CSRSTSESTAALGCLVKDYFPEPVTVSWNSGALTSGVHTFPAVL<br>QSSGLYSLSSVVTVPSSSLGTKTYTCNVDHKPSNTKVDKRVESK<br>YGPPCPPCPAPEFEGGPSVFLFPPKPKDTLMISRTPEVTCVVVD<br>VSQEDPEVQFNWYVDGVEVHNAKTKPREEQFNSTYRVVSVLTVL<br>HQDWLNGKEYKCKVSNKGLPSSIEKTISKAKGQPREPQVYTLPP<br>SQEEMTKNQVSLTCLVKGFYPSDIAVEWESNGQPENNYKTTPPV<br>LDSDGSFFLYSRLTVDKSRWQEGNVFSCSVMHEALHNHYTQKSL<br>SLSLGK |
| 5 | Amino acid sequence of humanized light chain of anti-CD40 antibody 12E12 (hAnti-CD40VH3-LV-hIgG4HC) | DIQMTQSPSSLSASVGDRVTITCSASQGISNYLNWYQQKPGKAV<br>KLLIYYTSILHSGVPSRFSGSGSGTDYTLTISSLQPEDFATYYC<br>QQFNKLPPTFGGGTKLEIKGTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| 6 | Fusion polypeptide; JS sites are lower case; FlexV1 is in italics; Env gp140 is underlined | EVQLVESGGGLVQPGGSLKLSCATSGFTFSDYYMYWVRQAPGKG<br>LEWVAYINSGGGSTYYPDTVKGRFTISRDNAKNTLYLQMNSLRA<br>EDTAVYYCARRGLPFHAMDYWGQGTLVTVSSASTKGPSVFPLAP<br>CSRSTSESTAALGCLVKDYFPEPVTVSWNSGALTSGVHTFPAVL<br>QSSGLYSLSSVVTVPSSSLGTKTYTCNVDHKPSNTKVDKRVESK<br>YGPPCPPCPAPEFEGGPSVFLFPPKPKDTLMISRTPEVTCVVVD<br>VSQEDPEVQFNWYVDGVEVHNAKTKPREEQFNSTYRVVSVLTVL<br>HQDWLNGKEYKCKVSNKGLPSSIEKTISKAKGQPREPQVYTLPP<br>SQEEMTKNQVSLTCLVKGFYPSIDAVEWESNGQPENNYKTTPPV<br>LDSDGSFFLYSRLTVDKSRWQEGNVFSCSVMHEALHNHYTQKSL<br>SLSLGKas*QTPTNTISVTPTNNSTPTNNSNPKPNP*asNLWVTVY<br>YGVPVWKEAKTTLFCASDAKVYEKEVHNVWATHACVPTDPNPQE<br>IVLGNVTENFNMWKNDMVDQMHEDIISLWDQSLKPCVKLTPLCV<br>TLNCTEVNVTRNVNNSVVNNTTNVNNSMNGDMKNCSFNITTELK<br>DKKKNVYALFYKLDIVSLNETDDSETGNSSKYYRLINCNTSALT<br>QACPKVYSFDPIPIHYCAPAGYAILKCNNKTFNGTGPCHNVSTV<br>QCTHGIKPVVSTQLLLNGSLAEEGIIIRSENLTNNVKTIIVHLN<br>RSIEIVCVRPNNNTRQSIRIGPGQTFYATGDIIGDIRQAHCNIS<br>RTNWTKTLREVRNKLREHFPNKNITFKPSSGGDLEITTHSFNCR<br>GEFFYCNTSGLFSINYTENNTDGTPITLPCRIRQIINMWQEVGR<br>AMYAPPIENGNIACKSDITGLLLVRDGGSTNDSTNNNTEIFRPA<br>GGDMRDNWRSELYKYKVVEIKPLGIAPTEAKRRVVEREKRAVGI<br>GAVFLGFLGAAGSTMGAASITLTAQARQVLSGIVQQQSNLLRAI<br>EAQQHLLQLTVWGIKQLQTRVLAIERYLKDQQLLGLWGCSGKLI |

IV. Listing of Sequences

| SEQ ID NO | Brief Description | SEQUENCE |
|---|---|---|
| | | CTTAVPWNISWSNKSKTDIWDNMTWMQWDREISNYTNTIYRLLE<br>DSQSQQEQNEKDLLALDSWNNLWNWFDITKWLWYIKas |
| 7 | Coding nt sequence of SEQ ID NO: 5 | ATGAGGGTCCCCGCTCAGCTCCTGGGGCTCCTGCTGCTCTGGCT<br>CCCAGGCGCGCGATGTGATATCCAGATGACACAGAGCCCTTCCT<br>CCCTGTCTGCCTCTGTGGGAGACAGAGTCACCATCACCTGCAGT<br>GCAAGTCAGGGCATTAGCAATTATTTAAACTGGTATCAGCAGAA<br>ACCAGGCAAGGCCGTTAAACTCCTGATCTATTACACATCAATTT<br>TACACTCAGGAGTCCCATCAAGGTTCAGTGGCAGTGGGTCTGGG<br>ACAGATTATACCCTCACCATCAGCTCCCTGCAGCCTGAAGATTT<br>CGCCACTTACTATTGTCAGCAGTTTAATAAGCTTCCTCCGACGT<br>TCGGTGGAGGCACCAAGCTGGAGATCAAAGGAACTGTGGCTGCA<br>CCATCTGTCTTCATCTTCCCGCCATCTGATGAGCAGTTGAAATC<br>TGGAACTGCCTCTGTTGTGTGCCTGCTGAATAACTTCTATCCCA<br>GAGAGGCCAAAGTACAGTGGAAGGTGGATAACGCCCTCCAATCG<br>GGTAACTCCCAGGAGAGTGTCACAGAGCAGGACAGCAAGGACAG<br>CACCTACAGCCTCAGCAGCACCCTGACGCTGAGCAAAGCAGACT<br>ACGAGAAACACAAAGTCTACGCCTGCGAAGTCACCCATCAGGGC<br>CTGAGCTCGCCCGTCACAAAGAGCTTCAACAGGGGAGAGTGTTA<br>G |
| 8 | Coding nt sequence of fusion poly-peptide with signal sequence (SEQ ID NO: 9) | ATGGGTTGGAGCCTCATCTTGCTCTTCCTTGTCGCTGTTGCTAC<br>GCGTGTCCACTCCGAAGTGCAGCTGGTGGAGTCTGGGGGAGGCT<br>TAGTGCAGCCCGGAGGGTCCCTGAAACTCTCCTGTGCAACCTCT<br>GGATTCACTTTCAGTGACTATTATATGTATTGGGTTCGCCAGGC<br>CCCAGGCAAGGGCCTGGAGTGGGTCGCATACATTAATTCTGGTG<br>GTGGTAGCACCTATTATCCAGACACTGTAAAGGGCCGATTCACC<br>ATCTCCAGAGACAATGCCAAGAACACCCTGTACCTGCAAATGAA<br>CAGCCTGAGGGCCGAGGACACAGCCGTGTATTACTGTGCAAGAC<br>GGGGGTTACCGTTCCATGCTATGGACTATTGGGTCAAGGAACC<br>CTGGTCACCGTCTCCTCAGCTTCCACCAAGGGCCCATCCGTCTT<br>CCCCCTGGCGCCCTGCTCCAGGAGCACCTCCGAGAGCACAGCCG<br>CCCTGGGCTGCCTGGTCAAGGACTACTTCCCCGAACCGGTGACG<br>GTGTCGTGGAACTCAGGCGCCCTGACCAGCGGCGTGCACACCTT<br>CCCGGCTGTCCTACAGTCCTCAGGACTCTACTCCCTCAGCAGCG<br>TGGTGACCGTGCCCTCCAGCAGCTTGGGCACGAAGACCTACACC<br>TGCAATGTAGATCACAAGCCCAGCAACACCAAGGTGGACAAGAG<br>AGTTGAGTCCAAATATGGTCCCCCATGCCCACCATGCCCAGCAC<br>CTGAGTTCGAGGGGGGACCATCAGTCTTCCTGTTCCCCCCAAAA<br>CCCAAGGACACTCTCATGATCTCCCGGACCCCTGAGGTCACGTG<br>CGTGGTGGTGGACGTGAGCCAGGAAGACCCCGAGGTCCAGTTCA<br>ACTGGTACGTGGATGGCGTGGAGGTGCATAATGCCAAGACAAAG<br>CCGCGGGAGGAGCAGTTCAACAGCACGTACCGTGTGGTCAGCGT<br>CCTCACCGTCCTGCACCAGGACTGGCTGAACGGCAAGGAGTACA<br>AGTGCAAGGTCTCCAACAAAGGCCTCCCGTCCTCCATCGAGAAA<br>ACCATCTCCAAAGCCAAAGGGCAGCCCCGAGAGCCACAGGTGTA<br>CACCCTGCCCCCATCCCAGGAGGAGATGACCAAGAACCAGGTCA<br>GCCTGACCTGCCTGGTCAAAGGCTTCTACCCCAGCGACATCGCC<br>GTGGAGTGGGAGAGCAATGGGCAGCCGGAGAACAACTACAAGAC<br>CACGCCTCCCGTGCTGGACTCCGACGGCTCCTTCTTCCTCTACA<br>GCAGGCTAACCGTGGACAAGAGCAGGTGGCAGGAGGGGAATGTC<br>TTCTCATGCTCCGTGATGCATGAGGCTCTGCACAACCACTACAC<br>AGAAGAGCCTCTCCCTGTCTCTGGGTAAAGCTAGCCAGACCCCG<br>ACCAACACCATTTCCGTGACCCCCACCAACAATAGCACTCCGAC<br>GAACAACAGCAACCCCAAGCCCAACCCGGCATCAAACCTCTGGG<br>TGACCGTGTACTATGGCGTCCCTGTGTGGAAAGAAGCCAAGACC<br>ACCCTGTTCTGCGCGTCCGACGCCAAGGTCTACGAAAAGGAGGT<br>GCACAATGTCTGGGCCACTCACGCCTGCGTCCCCACTGACCCAA<br>ACCCACAAGAAATCGTGCTGGGGAACGTGACCGAGAACTTCAAT<br>ATGTGGAAGAACGACATGGTGGACCAGATGCATGAGGATATCAT<br>CAGCCTGTGGGACCAGTCGCTCAAGCCTTGCGTCAAGCTGACTC<br>CTCTGTGTGTGACCTTGAACTGTACTGAAGTGAACGTGACCAGG<br>AACGTCAACAACAGCGTGGTCAACAACACTACCAACGTGAACAA<br>CTCCATGAACGGAGACATGAAGAATTGCTCCTTCAACATCACCA<br>CCGAACTCAAGGACAAGAAGAAGAATGTGTACGCCCTGTTCTAC<br>AAGTTGGACATCGTGTCCCTCAACGAAACTGACGATTCCGAAAC<br>CGGGAACTCGTCCAAGTATTACCGGCTCATCAACTGCAACACCT<br>CCGCCCTGACTCAGGCTTGTCCGAAAGTGTCCTTCGACCCAATT<br>CCGATCCATTACTGCGCCCCCGCCGGTTACGCCATTCTGAAGTG<br>CAACAATAAGACCTTCAACGGAACAGGCCCCTGCCACAACGTGT<br>CGACCGTGCAGTGCACACACGGTATCAAACCCGTCGTGTCCACC<br>CAACTCCTGCTGAACGGCTCACTGGCTGAGGAGGGTATTATCAT<br>CCGGTCCGAGAACCTGACTAACAACGTGAAAACCATTATCGTGC<br>ACCTGAACCGATCGATCGAAATCGTCTGCGTGCGCCCCTAACAAC<br>AATACTCGGCAGTCCATCCGGATCGGGCCTGGACAGACTTTCTA |

IV. Listing of Sequences

| SEQ ID NO | Brief Description | SEQUENCE |
|---|---|---|
| | | CGCGACCGGAGATATCATTGGAGATATCAGACAGGCGCACTGTA<br>ACATCTCCCGCACCAACTGGACCAAGACCCTGAGAGAAGTCAGG<br>AACAAGCTCCGGGAGCACTTCCCCAACAAGAACATCACCTTTAA<br>GCCCGTCCTCCGGCGGCGACCTGGAGATTACCACTCATTCGTTC<br>AACTGCCGCGGGGAATTCTTCTACTGTAATACCTCCGGACTGTT<br>TTCCATCAACTACACTGAAAACAACACCGATGGCACCCCGATTA<br>CCCTTCCGTGCCGGATTAGGCAGATCATTAATATGTGGCAGGAG<br>GTCGGACGGGCTATGTACGCCCCGCCGATTGAGGGAAATATCGC<br>CTGCAAATCCGACATTACTGGCCTGCTGCTCGTGCGCGACGGAG<br>GCTCGACCAACGACAGCACCAACAACAACACTGAGATCTTCCGG<br>CCCGCCGGCGGAGATATGAGAGATAACTGGAGGTCCGAACTTTA<br>CAAGTACAAGGTCGTGGAAATCAAGCCGCTTGGTATTGCACCTA<br>CCGAGGCCAAGAGAAGAGTGGTGGAGCGGGAGAAGCGGGCAGTG<br>GGGATCGGAGCCGTGTTCCTGGGATTCCTGGGCGCGGCGGGCTC<br>GACCATGGGAGCGGCCTCTATTACCCTGACGGCTCAGGCCCGCC<br>AAGTGCTGAGCGGAATCGTGCAGCAGCAATCGAATCTGCTGCGG<br>GCCATCGAAGCCCAGCAGCACCTCTTGCAACTTACTGTGTGGGG<br>TATCAAGCAGCTTCAAACTCGCGTGTTGGCCATAGAACGCTACC<br>TGAAGGACCAGCAGTTGCTCGGACTCTGGGGATGCAGCGGGAAG<br>CTGATTTGCACTACTGCCGTGCCGTGGAACATCTCCTGGTCAAA<br>CAAGAGCAAAACCGACATTTGGACAACATGACGTGGATGCAGT<br>GGGATCGGGAGATCTCAAACTACACTAACACCATCTACCGCCTG<br>CTGGAGGACTCCCAGTCACAACAGGAACAGAACGAAAAGGATCT<br>GCTGGCACTGGACTCATGGAACAACCTGTGGAACTGGTTTGACA<br>TCACCAAGTGGCTGTGGTACATCAAGGCGTCTTGA |
| 9 | Fusion poly-<br>peptide with<br>signal peptide<br>Signal peptide is<br>double underlined;<br>JS sites are<br>lower case;<br>FlexV1 is in<br>italics; Env<br>gp140 is<br>underlined | <u>MGWSLILLFLVAVATRVHS</u>EVQLVESGGGLVQPGGSLKLSCATS<br>GFTFSDYYMYWVRQAPGKGLEWVAYINSGGGSTYYPDTVKGRFT<br>ISRDNAKNTLYLQMNSLRAEDTAVYYCARRGLPFHAMDYWGQGT<br>LVTVSSASTKGPSVFPLAPCSRSTSESTAALGCLVKDYFPEPVT<br>VSWNSGALTSGVHTFPAVLQSSGLYSLSSVVTVPSSSGLTKTYT<br>CNVDHKPSNTKVDKRVESKYGPPCPPCPAPEFEGGPSVFLFPPPK<br>PKDTLMISRTPEVTCVVVDVSQEDPEVQFNWYVDGVEVHNAKTK<br>PREEQFNSTYRVVSVLTVLHQDWLNGKEYKCKVSNKGLPSSIEK<br>TISKAKGQPREPQVYTLPPSQEEMTKNQVSLTCLVKGFYPSDIA<br>VEWESNGQPENNYKTTPPVLDSDGSFFLYSRLTVDKSRWQEGNV<br>FSCSVMHEALHNHYTQKSLSLSLGKas*QTPTNTISVTPTNNSTP*<br>*TNNSNPKPN*as<u>NLWVTVYYGVPVWKEAKTTLFCASDAKVYEKE</u><br><u>VHNVWATHACVPTDPNPQEIVLGNVTENFNMWKNDMVDQMHEDI</u><br><u>ISLWDQSLKPCVKLTPLCVTLNCTEVNVTRNVNNSVVNNTTNVN</u><br><u>NSMNGDMKNCSFNITTELKDKKKNVYALFYKLDIVSLNETDDSE</u><br><u>TGNSSKYYRLINCNTSALTQACPKVSFDPIPIHYCAPAGYAILK</u><br><u>CNNKTFNGTGPCHNVSTVQCTHGIKPVVSTQLLLNGSLAEEGII</u><br><u>IRSENLTNNVKTIIVHLNRSIEIVCVRPNNNTRQSIRIGPGQTF</u><br><u>YATGDIIGDIRQAHCNISRTNWTKTLREVRNKLREHFPNKNITF</u><br><u>KPSSGGDLEITTHSFNCRGEFFYCNTSGLFSINYTENNTDGTPI</u><br><u>TLPCRIRQIINMWQEVGRAMYAPPIEGNIACKSDITGLLLVRDG</u><br><u>GSTNDSTNNNTEIFRPAGGDMRDNWRSELYKYKVVEIKPLGIAP</u><br><u>TEAKRRVVEREKRAVGIGAVFLGFLGAAGSTMGAASITLTAQAR</u><br><u>QVLSGIVQQQSNLLRAIEAQQHLLQLTVWGIKQLQTRVLAIERY</u><br><u>LKDQQLLGLWGCSGKLICTTAVPWNISWSNKSKTDIWDNMTWMQ</u><br><u>WDREISNYTNTIYRLLEDSQSQQEQNEKDLLALDSWNNLWNWFD</u><br><u>ITKWLWYIK</u>as |
| 10 | (12E12) HCD40-<br>CDR1H | GFTFSDYYMY |
| 11 | (12E12) HCD40-<br>CDR2H | YINSGGGSTYYPDTVKG |
| 12 | (12E12) HCD40-<br>CDR3H | RGLPFHAMDY |
| 13 | (12E12) LCD40-<br>CDR1L | SASQGISNYLN |
| 14 | (12E12) LCD40-<br>CDR2L | YTSILHS |
| 15 | (12E12) LCD40-<br>CDR3L | QQFNKLPPT |
| 16 | rAB-pIRES2[manti-<br>CD40_11B6.1C3_<br>H-LV-hIgG4H-C] | EVQLQQSGPELVKPGASVKISCKASGYSFTGYYMHWVKQSHVKS<br>LEWIGRINPYNGATSYNQNFKDKASTLVDKSSSTAYMELHSLTS<br>EDSAVYYCAREDYVYWGQGTTLTVSSAKTKGPSVFPLAPCSRST |

IV. Listing of Sequences

| SEQ ID NO | Brief Description | SEQUENCE |
|---|---|---|
| | | SESTAALGCLVKDYFPEPVTVSWNSGALTSGVHTFPAVLQSSGL YSLSSVVTVPSSSLGTKTYTCNVDHKPSNTKVDKRVESKYGPPC PPCPAPEFEGGPSVFLFPPKPKDTLMISRTPEVTCVVVDVSQED PEVQFNWYVDGVEVHNAKTKPREEQFNSTYRVVSVLTVLHQDWL NGKEYKCKVSNKGLPSSIEKTISKAKGQPREPQVYTLPPSQEEM TKNQVSLTCLVKGFYPSDIAVEWESNGQPENNYKTTPPVLDSDG SFFLYSRLTVDKSRWQEGNVFSCSVMHEALHNHYTQKSLSLSLG KAS |
| 17 | rAB-pIRES2[manti-CD40_11B6.1C3_K-LV-hIgGK-C] | DVVMTQTPLSLPVSGDQASISCRSSQSLVHSNGNTYLHWYLQKP GQSPKLLIYKVSNRFSGVPDRFSGSGSSGTDFALKISRVEAEDL GVYFCSQSTHVPWTFGGGTKLEIKRTVAAPSVFIFPPSDEQLKS GTASVVCLLNNFYPREAKVQWKVDNALQSGNSQESVTEQDSKDS TYSLSSTLTLSKADYEKHKVYACEVTHQGLSSPVTKSFNRGEC |
| 18 | (11B6) HCD40-CDR1H | GYSFTGYYMH |
| 19 | (11B6) HCD40-CDR2H | RINPYNGATSYNQNFKD |
| 20 | (11B6) HCD40-CDR3H | EDYVY |
| 21 | (11B6) LCD40-CDR1L | RSSQSLVHSNGNTYLH |
| 22 | (11B6) LCD40-CDR2L | KVSNRFS |
| 23 | (11B6) LCD40-CDR3L | SQSTHVPWT |
| 24 | rAB-pIRES2[manti-CD40_12B4.2C10_H-LV-hIgG4H-C] | EVQLQQSGPELVKPGASVKMSCKASGYTFTDYVLHWVKQKPGQG LEWIGYINPYNDGTKYNEKFKGKATLTSDKSSSTAYMELSSLTS EDSAVYYCARGYPAYSGYAMDYWGQGTSVTVSSAKTKGPSVFPL APCSRSTSESTAALGCLVKDYFPEPVTVSWNSGALTSGVHTFPA VLQSSGLYSLSSVVTVPSSSLGTKTYTCNVDHKPSNTKVDKRVE SKYGPPCPPCPAPEFEGGPSVFLFPPKPKDTLMISRTPEVTCVV VDVSEQDPEVQFNWYVDGVEVHNAKTKPREEQFNSTYRVVSVLT VLHQDWLNGKEYKCKVSNKGLPSSIEKTISKAKGQPREPQVYTL PPSQEEMTKNQVSLTCLVKGFYPSDIAVEWESNGQPENNYKTTP PVLDSDGSFFLYSRLTVDKSRWQEGNVFSCSVMHEALHNHYTQK SLSLSLGKAS |
| 25 | rAB-pIRES2[manti-CD40_12B4.2C10_K-LV-v2-hIgGK-C] | DIQMTQTTSSLSASLGDRVTISCRASQDISNYLNWYQQKPDGTV KLLIYYTSRLHSGVPSRFSGSGSGTDYSLTISNLEQEDIATYFC HHGNTLPWTFGGGTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 26 | (12B4) HCD40-CDR1H | GYTFTDYVLH |
| 27 | (12B4) HCD40-CDR2H | YINPYNDGKTYNEKFKG |
| 28 | (12B4) HCD40-CDR3H | GYPAYSGYAMDY |
| 29 | (12B4) LCD40-CDR1L | RASQDISNYLN |
| 30 | (12B4) LCD40-CDR2L | YTSRLHS |
| 31 | (12B4) LCD40-CDR3L | HHGNTLPWT |

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Superiority in Rhesus Macaques of Targeting HIV-1 Env Gp140 to CD40 Versus LOX-1 in Combination with Replication Competent NYVAC-KC for Induction of Env-Specific Antibody and T Cell Responses The inventors compared the HIV-1-specific immune responses generated by targeting HIV-1 envelope protein (Env gp140) to either CD40 or LOX-1, two endocytic receptors on dendritic cells (DCs), in Rhesus macaques primed with a poxvirus vector (NYVAC-KC) expressing Env gp140. The DC-targeting vaccines, humanized recombinant monoclonal antibodies fused to Env gp140, were administered as a boost with poly ICLC adjuvant either alone or co-administered with the NYVAC-KC vector. All the DC-targeting vaccine administrations with poly ICLC increased the low-level serum anti-Env IgG responses elicited by NYVAC-KC priming significantly more (up to P=0.01) than a group without poly ICLC. The responses were robust, cross-reactive, and contained antibodies specific to multiple epitopes within gp140 including the C1, C2, V1-3, C4, C5, and gp41 immuno-dominant regions. The DC-targeting vaccines also elicited modest serum Env-specific IgA responses. All groups gave serum neutralization activity limited to Tier 1 viruses and antibody dependent cytotoxicity responses (ADCC) after DC-targeting boosts. Furthermore, $CD4^+$ and $CD8^+$ T cell responses specific to multiple Env epitopes were strongly boosted by the DC-targeting vaccines+poly ICLC. Together, these results indicate that prime/boost immunization via NYVAC-KC and either αCD40.Env gp140/poly ICLC or αLOX-1.Env gp140/poly ICLC induced balanced antibody and T cell responses against HIV-1 Env. Co-administration of NYVAC-KC with the DC-targeting vaccines increased T cell responses, but had minimal effects on antibody responses except for suppressing serum IgA responses. Overall, compared to LOX-1, targeting Env to CD40 gave more robust T cell and serum antibody responses with broader epitope representation and greater durability.

In this study, we directly compare the efficacy of targeting HIV-1 Env gp140 to CD40 versus LOX-1 in combination with replication competent vaccinia virus vector NYVAC-KC encoding Env gp140. Specifically, this study aims to: i) establish the safety and immunogenicity of NYVAC-KC prime followed by boost via DC-targeting to either LOX-1 or CD40 formulated with poly ICLC adjuvant and either administered alone or co-administered with NYVAC-KC; ii) compare the boosting ability of DC-targeting via either LOX-1 or CD40 formulated with poly ICLC adjuvant either administered alone or co-administered with NYVAC-KC; and iii) test the boosting ability of DC-targeting via CD40 either co-administered with poly ICLC or administered alone.

A. Materials and Methods
1. Production and Quality Assurance of αCD40.Env gp140 and αLOX-1.Env gp140.

αCD40.Env gp140 was derived from the parental anti-human CD40 12E12 recombinant human IgG4 mAb (GenBank HQ738667.1 and HQ738666.1) via humanization of the mouse variable regions (Antitope, Ltd) as defined by the variable regions in GenBank KM660791 and KM660792. Env gp140 sequence derived from the codon optimized HIV-1 96ZM651 synthetic construct (NIH AIDS reagent program, GenBank AY181197.1 residues 94-2064) was inserted at the IgG4 heavy chain C-terminal codon distal to a flexV1 flexible linker spacer and proximal to 6 His codons. αLOX-1.Env gp140 was derived from the parental anti-human LOX-1 15C4 recombinant human IgG4 mAb; GenBank KM246787 and KM246788) via humanization of the mouse variable regions (Antitope, Ltd). This was fused to Env gp140 sequence as described above. Specificity and relative binding affinity of αCD40.Env gp140 and αLOX-1.Env gp140 to human and Rhesus macaque CD40 and LOX-1 ectodomains (encoded respectively by GenBank gb|AAO43990.1|residues 22-193, and ref|NP_001252791.1|residues 21-193, dbj|AB102861.1|residues 169-918 and ref|NM_001194668.1|residues 295-945) fused via the cohesion C-terminus (GenBank gb|CP000568.1|residues 3622666-3623172 with a Nhe I site linker) was tested by an adaption of multiplexed bead-based assay for equilibrium competition binding analysis of αLOX-1 Env gp140 and αCD40 Env gp140 interaction with human and NHP LOX-1 and CD40 ectodomains. In this assay, beads were coated with human LOX-1, NHP LOX-1, human CD40, or NHP CD40 ectodomains and incubated overnight with 10 ng/ml of the parental mouse αLOX-1 15C4 or αCD40 12E12 mAbs and varying concentrations of humanized αLOX-1, αLOX-1 Env gp140, αCD40, or αCD40 Env gp140, then probed with PE-labeled anti-mouse IgG, and analyzed with a Bio-Plex 200 instrument. There was no significant difference between the binding of humanized αLOX-1 vs. αLOX-1 Env gp140 to human ($EC_{50}$ 0.6 pM) or NHP LOX-1 ($IC_{50}$ 0.6 pM) coated beads, and the binding of humanized αCD40 vs. αCD40 Env gp140 to human ($IC_{50}$ 1 pM vs. 1.2 pM) or NHP ($IC_{50}$ 0.83 pM vs. 1.2 pM) CD40 coated beads was similar (data not shown). The vaccines were formulated and administered exactly as described below.

2. Animals and Assays.

Thirty male Rhesus macaques ranging in age from 3 to 6 years and weighing at least 4 kg were procured from Harlan Laboratories and housed at the Advanced Biosciences Laboratories (ABL) animal facility in Rockville, Md. The ABL in vivo facility is USDA-registered and accredited by the American Association for the Accreditation of Laboratory Animal Care International (AAALAC). ABL's veterinary practices comply with all policies of the "Guide for the Care and Use of Laboratory Animals," DHHS (NIH 85-23), Animal Welfare (DHHS-TN 73-2) the NIH Manual Issuance 4206 and 6000-3-4-58, "Responsibility for Care and Use of Animals CDC/NIH $4^{th}$ edition", "Biosafety in Microbiological and Biomedical Laboratories," and Public Health Service Policy on Humane Care and Use of Laboratory Animals under a Category 1 assurance from OLAW. All procedures were carried out under Ketamine anesthesia by trained personnel under the supervision of veterinary staff and all efforts were made to ameliorate the welfare and to minimize animal suffering in accordance with the "Weatherall report for the use of non-human primates" recommendations. Other than for a seven-day post-inoculation follow up observation period, animals were pair-housed in adjoining primate cages allowing social interactions, under controlled conditions of humidity, temperature and light (12-hour light/ 12-hour dark cycles). Food and water were available ad libitum. Animals were monitored and fed standard laboratory rations twice daily. Trained personnel offered dietary supplements with fresh fruit and occasional treats at least once a day. Early endpoint criteria, as proposed by the project team and approved by the IACUC, were used to determine when animals should be humanely euthanized. The ABL veterinarian was authorized to determine whether animals met such criteria and if necessary, was tasked to stabilize any affected animals prior to consulting with the lead investigators. ABL's Institutional Animal Care and Use Committee (IACUC) approved of the proposed study protocol prior to the initiation of any in vivo work. The protocol number assigned by the IACUC/ethics committee that approved this study is AUP567.

3. Vaccination Protocols.

The NYVAC-KC virus inoculum was provided in 0.2 ml aliquots as NYVAC-KC expressing Env gp140 (ZM96) and ZM96 Gag plus CN54 PolNef at 0.1 ml of each virus @ $1.2 \times 10^8$ pfu per vial. The immunogen mixture according to molar ratios was Env:GagPolNef=1:1. Prior to administration, the required number of vaccine vials containing the virus mixture were thawed at 37° C. and put on ice immediately after thawing. 1 ml of 1×TBS was added to each vial and briefly vortexed. Sonication with a Bransonic 1210 unit was performed according to the following procedure: fill water bath of the sonicator with water and ice; sonicate sample 3 times for 10 sec each time; after the sonication steps, vortex sample. For each animal, 1 ml of the vaccine preparation was drawn up from the vials by a 1 ml syringe and kept on ice until administration. Before immunization, the skin of the upper arm (deltoid) was shaved and cleaned with alcohol. Animals received the vaccine preparation via intramuscular injection of 1 ml of the vaccine preparation @$2 \times 10^8$ pfu/ml total of 2 viruses in the deltoid. The poly ICLC was provided in 1 ml vials at a concentration of 2 mg/ml. Vials (Hiltonol Lot: PJ215-1-10-01) were stored at 2-8° C. Administration was 1 mg (subcutaneous) in two injections of 250 µl in the center of each circular injection pattern (3-4 cm diameter) formed by the intradermal administrations of αLOX-1.Env gp140 or αCD40.Env gp140 vaccine components which were stored in 1 M Arginine+ 100 mM Tris.HCl Buffer pH 6-8. Protein vaccine administrations were at a 200 µg dose, intradermal in a total of 8 injections of 250 µl each (2 ml total injection)—four injections was performed in each side of the back placed in a circular pattern. To avoid toxicity of 1 M Arginine buffer, the concentrated protein was diluted approximately 1:4 in PBS before use. Each animal received in the upper back (dorsal thoracic) a total of 8 intradermal injections of 250 µl each. Four injections were performed in each side of the back placed in a circular pattern of 3–4 cm of diameter. Skin was shaved before injection and cleaned with 70% alcohol solution. Intradermal injections were performed using an insulin syringe. The injection of poly ICLC was performed after the i.d. injections of the proteins and in the middle of each circle with 500 µl injected s.c. This administration procedure was designed to promote drainage of antigen and adjuvant to the same lymph node site and at the recommendation of ABL's head veterinarian. The supervising veterinarian reported no adverse events from the vaccinations.

4. Neutralization Assay.

Neutralizing antibodies were measured as a function of reductions in luciferase (Luc) reporter gene expression after a single round of infection in TZM-bl cells. TZM-bl cells (also called JC57BL-13) and A3R5 cells were obtained from the NIH AIDS Research and Reference Reagent Program, as contributed by John Kappes and Xiaoyun Wu. Briefly, a pre-titrated dose of virus was incubated with serial 3-fold dilutions of test sample in duplicate in a total volume of 150 al for 1 h at 37° C. in 96-well flat-bottom culture plates. Freshly trypsinized cells (10,000 cells in 100 µl of growth medium containing 75 µg/ml DEAE dextran) were added to each well. One set of 8 control wells received cells+virus (virus control) and another set received cells only (background control). After 48 hours of incubation, 100 µl of cells was transferred to a 96-well black solid plate (Costar) for measurements of luminescence using the Britelite Luminescence Reporter Gene Assay System (PerkinElmer Life Sciences). Assay stocks of molecularly cloned Env-pseudotyped viruses were prepared by transfection in 293T/17 cells (American Type Culture Collection) and titrated in TZM-bl cells. This assay has been formally optimized and validated, and was performed in compliance with Good Clinical Laboratory Practices (GCLP), including participation in a formal proficiency testing program. Additional information on the assay and all supporting protocols may be found on the world wide web at: hiv.lanl.gov/content/nab-reference-strains/html/home.htm. The method for MB analysis of serum neutralization assays as shown in FIG. 4.

5. HIV-1 Specific Binding Antibody Assay.

HIV-1 specific IgG antibodies to gp120/gp140 proteins and V1/V2 scaffolds were measured by an HIV-1 binding antibody multiplex assay. All assays were run under GCLP compliant conditions, including tracking of positive controls by Levy-Jennings charts using 21CFR Part 11 compliant software. Positive controls included a HIVIG and CH58 mAb IgG titration. Negative controls included in every assay were blank (uncoupled) and MulVgp70_His6 (empty gp70 scaffold) coupled beads, a blank well on each assay plate, as well as HIV-1 negative sera. To control for antigen performance, we used the preset criteria that the positive control titer (HIVIG) included on each assay (and for assays with V1V2 antigens, CH58 mAb, had to be within +/−3 standard deviations of the mean for each antigen (tracked with a Levy-Jennings plot with preset acceptance of titer and calculated with a four-parameter logistic equation, Sigma-Plot, Systat Software). Antibody measurements were acquired on a Bio-Plex instrument (Bio-Rad, Hercules, Calif.) using 21CFR Part 11 compliant software and the readout is in MFI. The following antigens were examined: ZM96 gp140-C tag (Baylor Health); (Con S gp140 CF (a group M consensus envelope gp140; A1.con.env03 140 CF (clade A Consensus), B.con.env03 140 CF (clade B Consensus), C.con.env03 140 CF (clade C Consensus), clade A 00MSA 4076 gp140, gp70 control, gp70_B.CaseA2 V1/V2 (a recombinant clade B gp70 scaffold protein with the V1V2 variable region), C.1086V1-V2 Tags and C.1086 V2 tags (a transmitted clade C isolate provided by Drs. Liao and Haynes, Duke) and AE.A244 V1/V2 tags, AE.A244 V2 tags (Clade AE sequence of RV144 vaccine immunogen.

6. Serum Antibody Linear Epitope Mapping.

Serum epitope mapping of heterologous strains was performed as previously described with minor modifications. Briefly, array slides were provided by JPT Peptide Technologies GmbH (Germany) by printing a library designed by Dr. B. Korber, Los Alamos National Laboratory, onto Epoxy glass slides (PolyAn GmbH, Germany). The library contains overlapping peptides (15-mers overlapping by 12) covering 6 full length gp160 consensus sequences (Clade A, B, C, D, Group M, CRF1, and CRF2), and gp120 sequences of 6 vaccine strains (MN, A244, Th023, TV-1, ZM651, 1086C). 3 identical subarrays, each containing the full peptide library, were printed on each slide. All array slides were blocked for 1 hour, followed by a 2 hr incubation with 1:50 diluted serum samples and a subsequent 45 min incubation with Goat Anti-Hu IgG conjugated with AF647 (Jackson ImmunoResearch, PA). Array slides were scanned at a wavelength of 635 nm using an Axon Genepix 4300 Scanner (Molecular Devices, Sunnyvale, Calif., USA). Images were analyzed using Genepix Pro 7 software (Molecular Devices) to obtain binding intensity values for all peptides. Binding of postimmunization serum to each peptide was subtracted of its own baseline value, which was defined as the median signal intensity of the triplicates of the peptide for the matched prebleed serum plus 3 times the standard error of the triplicates. Binding magnitude to each identified epitope was defined as the highest binding by a single peptide within the epitope region.

7. Intracellular Cytokine Staining.

Cryopreserved PBMC were thawed and rested overnight in R10/RPMI 1640 (BioWhittaker, Walkersville, Md.), 10% FBS, 2 mM L-glutamine, 100 U/ml penicillin G, 100 µg/ml streptomycin] with 50 U/ml Benzonase (Novagen, Madison, Wis.) in a 37° C./5% $CO_2$ incubator. The following morning, cells were stimulated with peptide pools (2 µg/ml, described in 2) in the presence of GogiPlug (10 µg/ml; BD Biosciences, San Jose, Calif.) for 6 h. Negative controls received an equal concentration of DMSO instead of peptides. Subsequently, intracellular cytokine staining (ICS) was performed as described in the art. The following monoclonal antibodies were used: CD4-BV421 (clone OKT4; BioLegend), CD8-BV570 (clone RPA-T8; BioLegend), CD69-ECD (clone TP1.55.3; Beckman Coulter), CD3-Cy7APC (clone SP34.2; BD Biosciences), IFN-γ-APC (clone B27; BD Biosciences), IL-2-PE (clone MQ1-17H12; BD Biosciences), and TNF-FITC (clone Mab11; BD Biosciences). Aqua LIVE/DEAD kit (Invitrogen, Carlsbad, Calif.) was used to exclude dead cells. All antibodies were previously titrated to determine the optimal concentration. Samples were acquired on an LSR II flow cytometer and analyzed using FlowJo version 9.8 (Treestar, Inc., Ashland, Oreg.).

8. ADCC

ADCC activity against MW965.1 gp120 (provided by the Duke CAVD repository) coated CEM.NKR$_{CCR5}$ (NIH AIDS Reagent Program, Division of AIDS, NIAID, NIH: CEM.NKR-CCR5 from Dr. Alexandra Trkola) target cells was measured using the ADCC-GranToxiLux (GTL) assay as previously described in the art. The peak activity is the maximum activity observed at any dilution and considered positive if above the 8% Granzyme B activity cut-off.

9. ELISPOT

Millipore 96 well filtration plates were pre-treated with 70% EtOH, washed 5× with 1× PBS and then coated with 5 µg/ml mouse-anti-human-IFNγ antibody (BD Pharmingen) over night at 4° C. After blocking with complete RPMI for 2 h at 37° C., 2×10$^5$ PBMCs (prepared as for ICS) were stimulated in triplicates with peptide pools at 1 µg/ml, or PHA (2.5 µg/ml) as positive control, while addition of medium only served as negative control. The peptides and peptide pools used are those described in the art. Plates were incubated at 37° C. for 18-24 h before washing with cold $H_2O$ twice and PBS/T for five times. Biotinylated anti-IFNγ-antibody (Mabtech) was added at 1 µg/ml for 1 hour at 37° C. and, after washing, a 1:2000 dilution of Avidin-HRP (Vector Laboratories) was added, again for 1 h at 37° C. After final washing, stable DAB (Invitrogen) was added for 2 min, and then the reaction was stopped with water washing. After drying, the numbers of spots in each well were counted with an automated ELISPOT reader (CTL Immunospot).

10. Statistical Methods

Wilcoxon signed-rank tests or 2-tailed t tests are used to compare change of marker value at specific time points with baseline within each group. Comparison between groups at specific time points was made using the Wilcoxon rank sum test. Response rates were compared between groups using Fisher's exact test. Overall magnitude of ELISPOT response was compared between groups G1 and G2 by fitting a random effect model using log transformed data measured after W14. A p-value of less than or equal to 0.05 is considered statistically significant. Statistical analyses were done with R (version 3.1.2; The R foundation for Statistical Computing, Vienna, Austria). For the antigen-specific antibody measurements several criteria are used to determine if data from an assay are acceptable and can be statistically analyzed. The blood draw rate must be within the allowable visit window as determined by the protocol. Secondly, if the blank bead negative control exceeds 5,000 MFI, the sample will be repeated. If the repeat value exceeds 5,000 MFI, the sample will be excluded from analysis due to high background. QC and standard curve titers must fall within +/−3 standard deviations of the historical mean plotted on Levey Jennings charts. Sample and control replicates must also be within 20% CV. Samples are declared to have positive responses if they meet three conditions: i) the MFI minus Blank bead or MulVgp70 His6 values are greater than or equal to antigen-specific cutoff (based on the average+3 standard deviations of 60 seronegative plasma samples), ii) the MFI minus Blank values are greater than 3 times the baseline MFI minus blank values, and iii) the MFI values are greater than 3 times the baseline MFI values. For each antigen and visit, the magnitude of binding response among both responders and non-responders is compared between groups using the Wilcoxon rank sum test. Response rates were compared between groups using Fisher's exact test. No adjustments were made for multiple comparisons, as these are exploratory analyses for which increased Type 1 error is tolerated for better sensitivity to detect effects. A p-value of less than or equal to 0.05 is considered statistically significant.

B. Results

1. HIV-1 Env gp140 Targeted to Either LOX-1 or CD40 Elicits Env-Specific B Cell Responses in NHPs Primed with a Live Virus Vector.

The inventors previously described an anti-human LOX-1 recombinant human IgG4 antibody fused via a flexible linker to the heavy (H) chain C-terminus to codon optimized Env gp140 protein from the clade C HIV-1 96ZM651(called ZM96) strain (αLOX-1.Env gp140). A similar fusion protein (αCD40.Env gp140) was generated linking gp140 to a humanized anti-human CD40 recombinant human IgG4 antibody. αCD40.Env gp140 retained specific binding to human and Rhesus macaque CD40 (see Materials and Methods). In the previous study αLOX-1.Env gp140 administered intradermally (i.d.) with TLR3 ligand poly ICLC given nearby subcutaneously (s.c.) efficiently boosted both humoral and cellular responses in Rhesus macaques primed with two intramuscular (i.m.) injections of replication competent NYVAC-KC vaccinia virus vectors encoding HIV-1 Gag, Nef, Pol and Env gp140 sequences. To this protocol the inventors added other NHP groups to test the relative efficacy of targeting Env gp140 via CD40 versus LOX-1, to investigate potential benefits of co-administering NYVAC-KC viruses coding for Env gp140 and Gag, Nef, Pol with the DC-targeting vaccinations, and to establish the potency of CD40 targeting in the absence of TLR3 stimulation. Table 1 shows the overall study design and tissue sampling schedule.

Figures 1A, 1B:
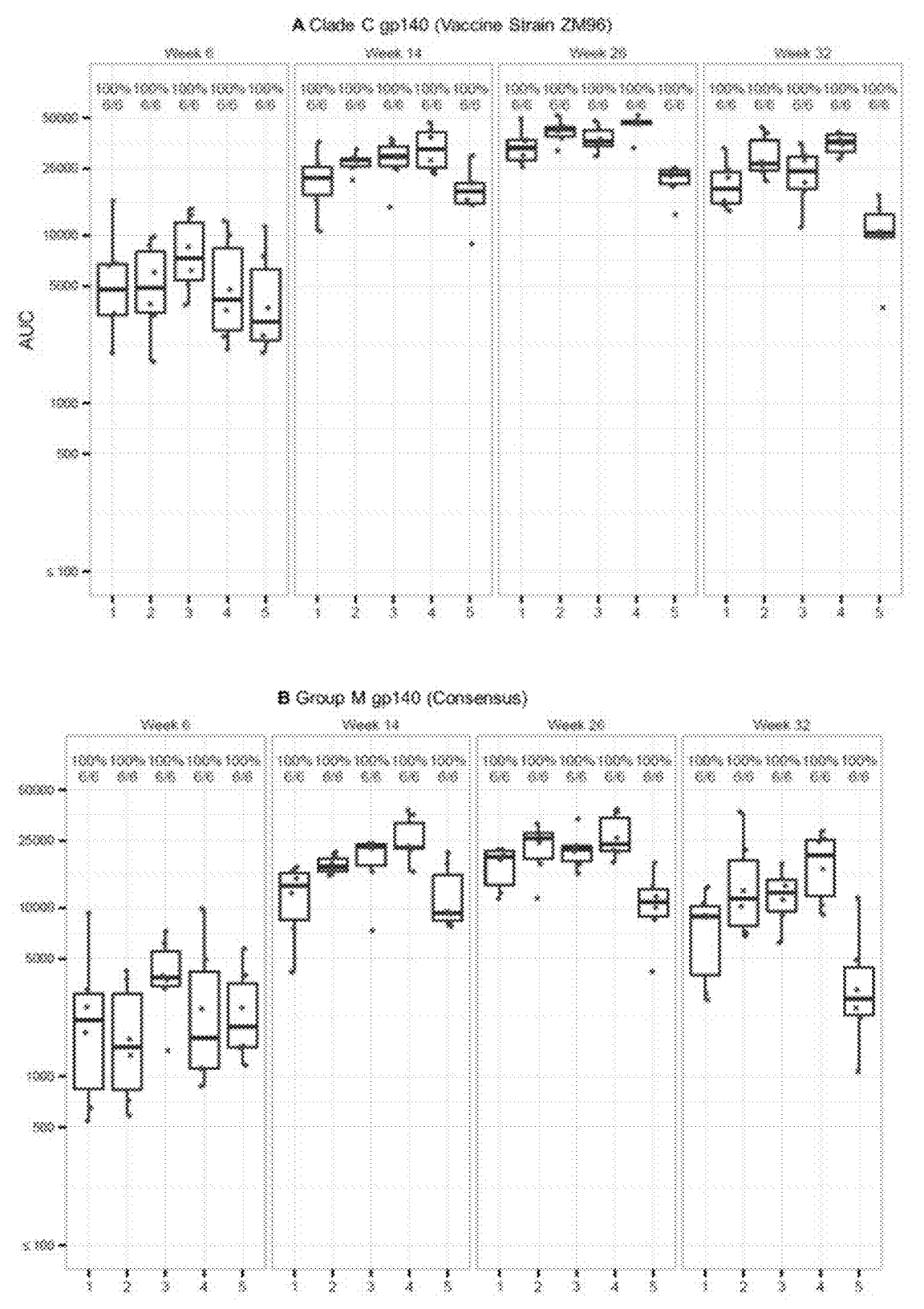
Figures 1C, 1D:
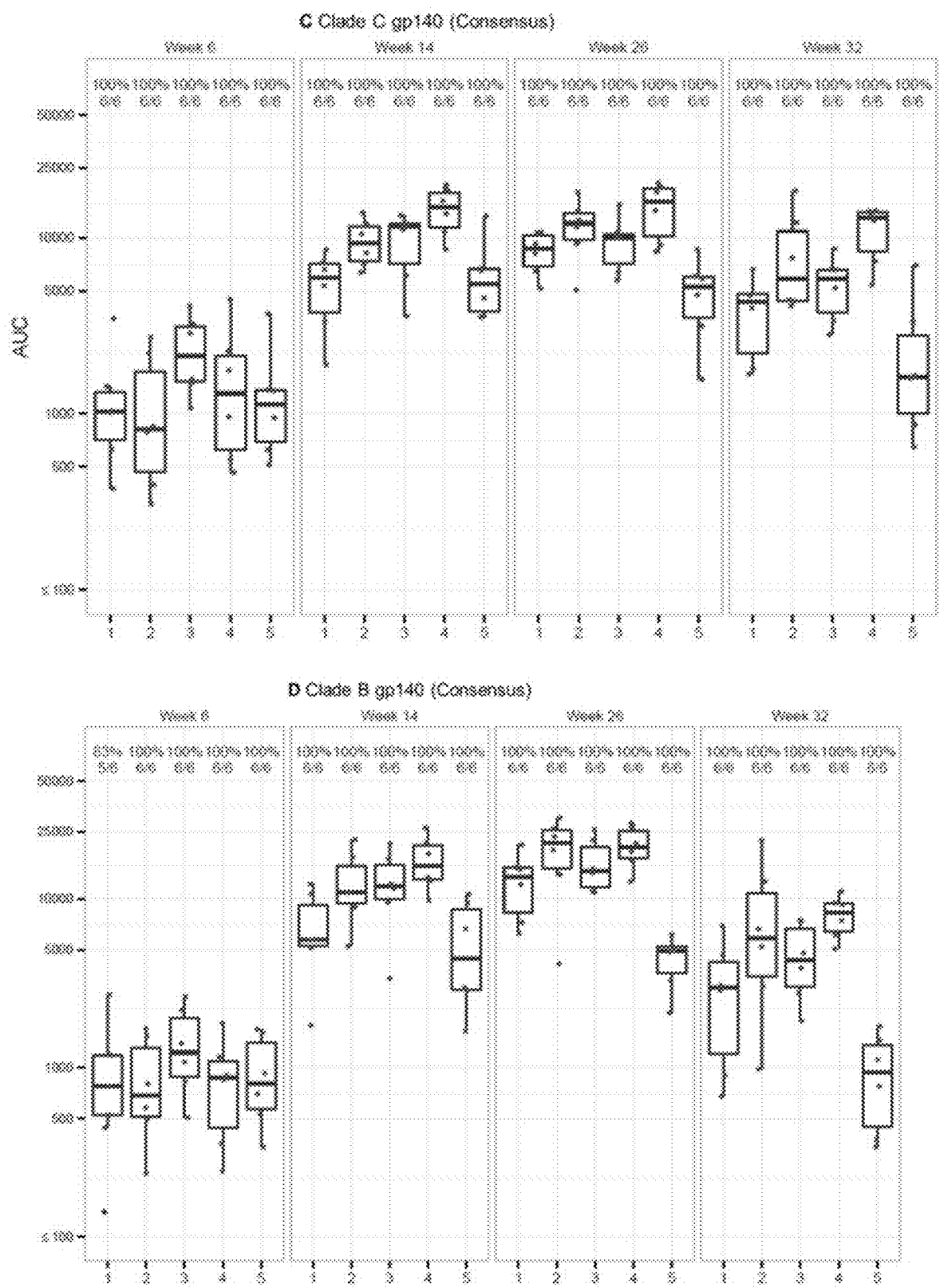
Figure 1E:
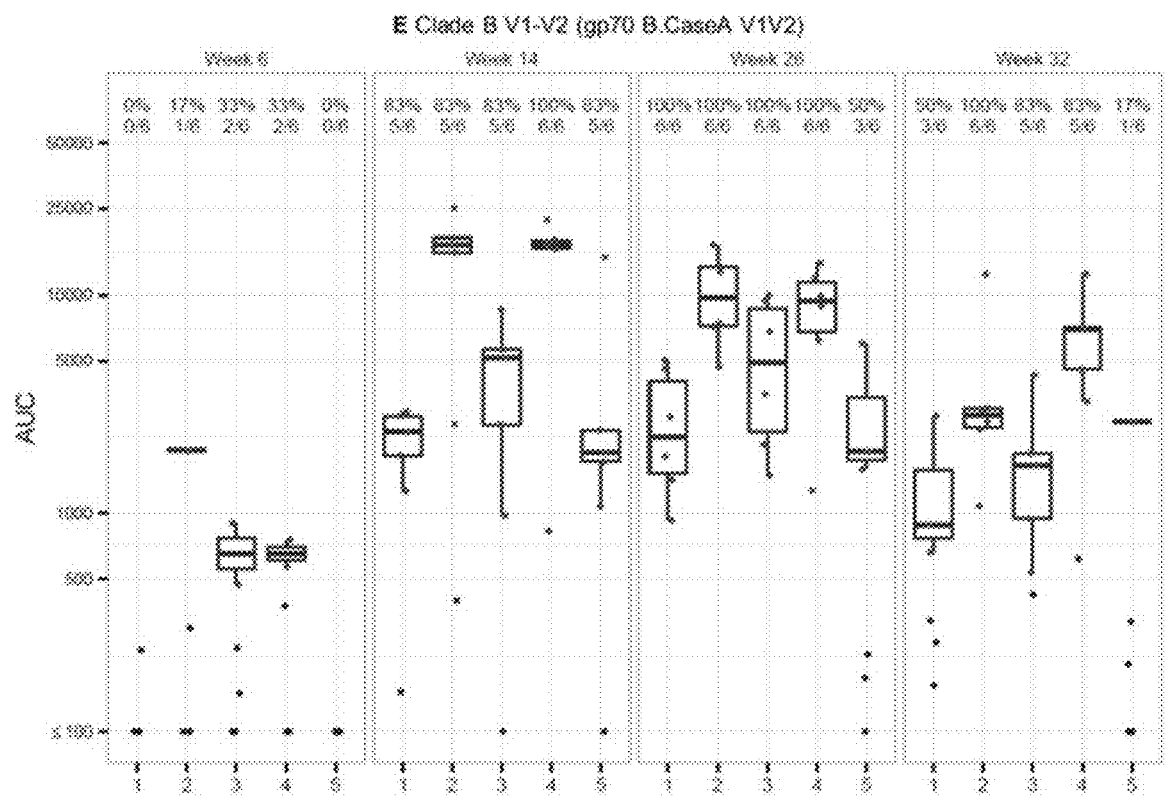
Figure 1F:
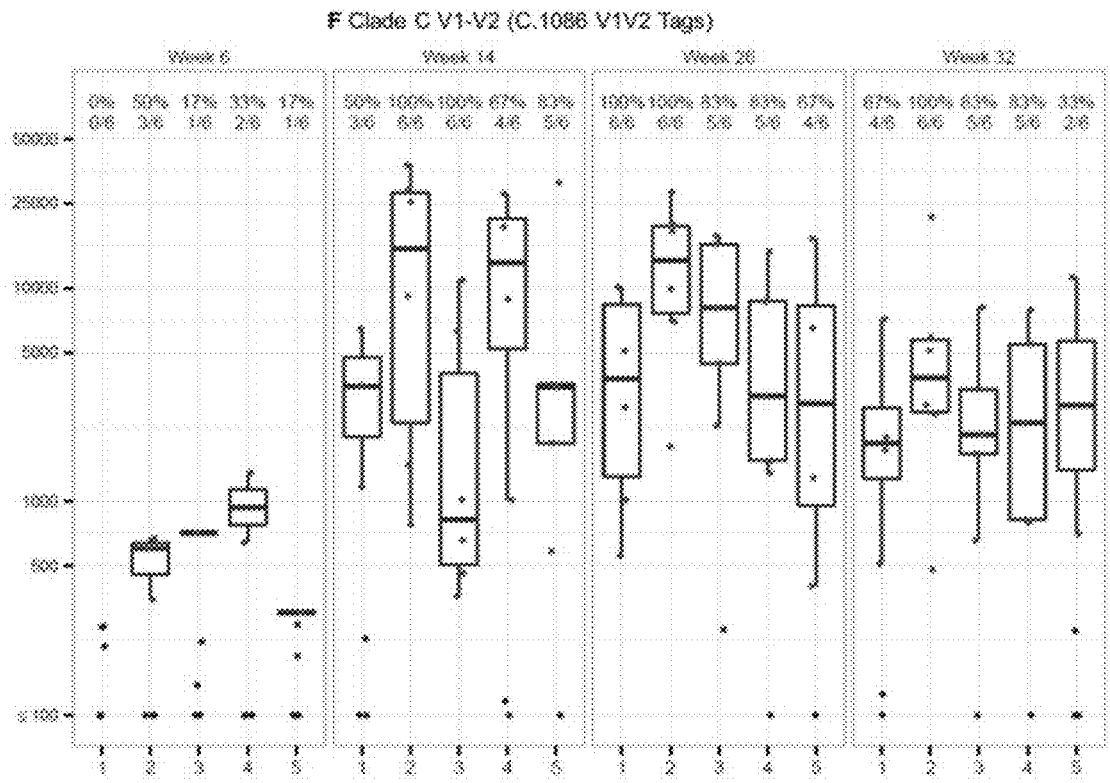
Figures 1G, 1H:
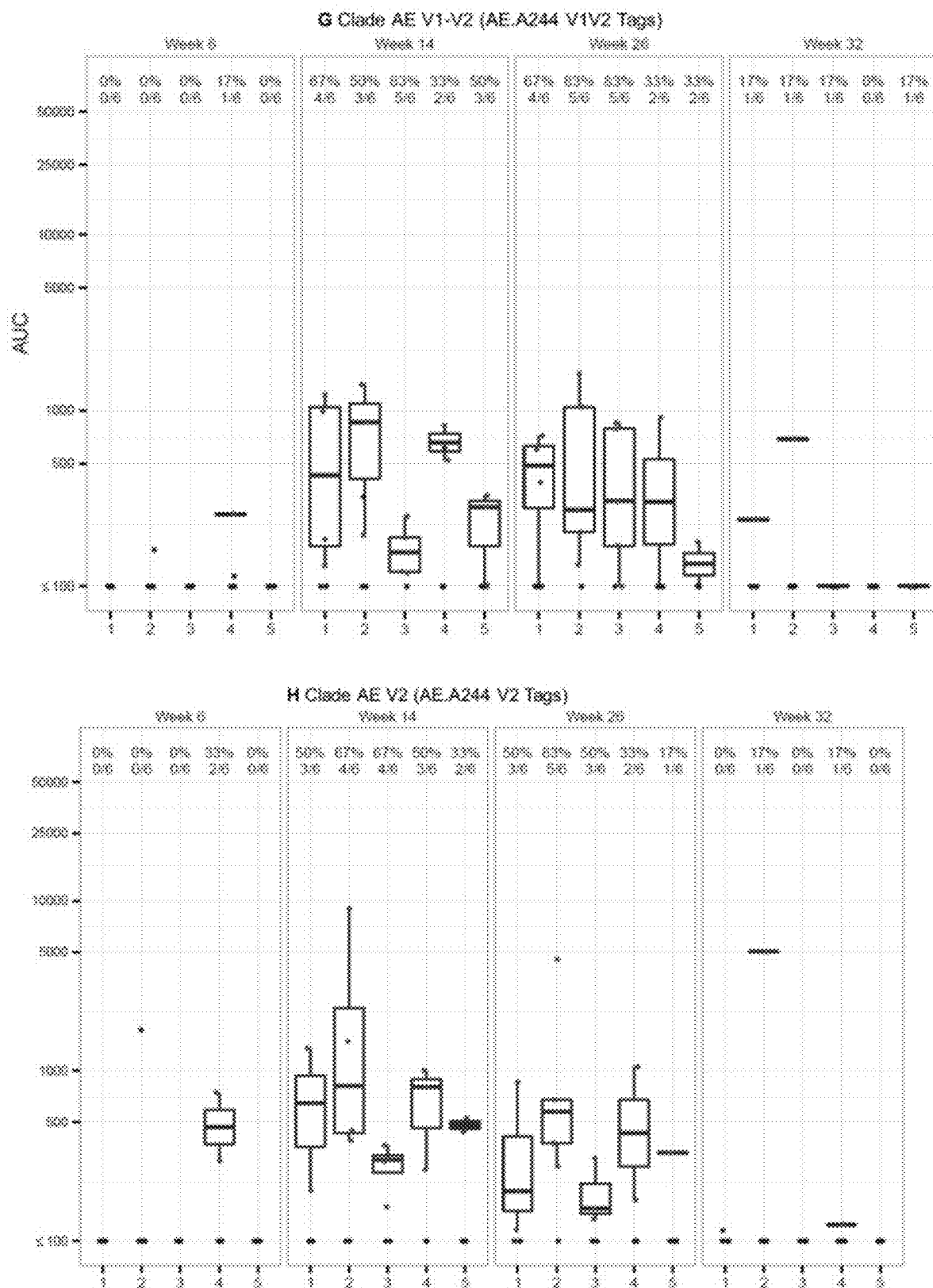

In this study, Env-specific serum IgG responses were observed in all animals at all 3 post-DC-targeting vaccination time points, including high titers against the vaccine strain ZM96 gp140 FIG. 1A) as well as group M consensus (FIG. 1B, con S gp140 CF), clade C (FIG. 1C, C.con.env03

140 CF), and clade B (FIG. 1D, B.con.env03 140 CF) cross clade sequences. Titers in response to the two NYVAC-KC vaccinations (week 6) were modest, but were boosted in all groups to almost maximal levels after one DC-targeting vaccine administration. These responses were maximal after the second DC-targeting vaccine administration (week 26, the primary immunogenicity endpoint) and waned somewhat 8 weeks after the final vaccinations (FIG. 1). IgG binding antibody responses to V1V2 region antigens (i.e., a response that correlated with decreased risk of HIV-1 infection in RV144 human clinical trial) were observed in only a few NHPs at the early time point, but were boosted or evoked to almost maximal levels by a single LOX-1 or CD40-targeting vaccination (FIG. 1E-H). Notably, IgG responses to V1V2 were significantly higher (p=0.01 week 26 and p=0.02 week 32) when NYVAC-KC was co-administered with CD40 but not LOX-1 targeting despite similar overall binding antibody levels between the paired groups (see G1/G2, FIG. 1, Table 2). The inventors next confirmed that the V1V2 response in this study was in part due to recognition of the V2 sequence (and not just C1-V1) contained within these antigens by demonstrating that all groups elicited responses to an antigen designed to only expose V2 region conformational and linear epitopes (V2 Tags) (FIG. 1, Table 2). In all cases after the DC-targeting vaccinations, G4 N2Cp2 values were significantly higher than G5 N2C2 for all gp140 antigens and the gp70 B CaseA V1V2 antigen (p-value=0.01) indicating a significant benefit to co-administering poly ICLC with the CD40-targeting vaccine (Table 2).

Figure 2:
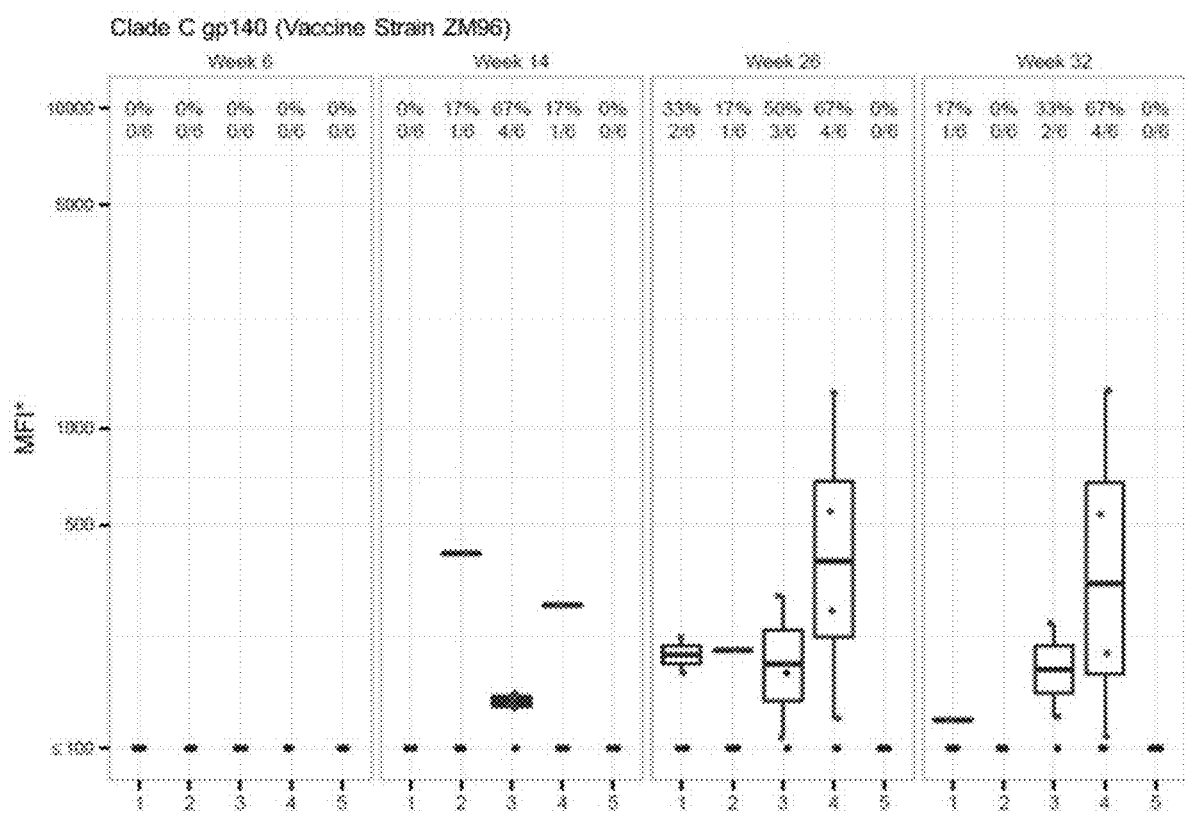
FIG. 2. Serum Env gp140-specific IgA responses elicited by αLOX-1.Env gp140 and αCD40.Env gp140 fusion protein administration. Total binding IgA antibody levels against Clade C gp140 (Vaccine Strain, ZM96) induced by the different vaccination groups are shown. Individual serum samples were obtained at weeks 6, 14, 26, and 32 from each macaque (n=6 per group) immunized as per G1 N2[LpN]2, G2 N2[CpN]2, G3 N2Lp2, G4 N2Cp2, and G5 N2C2 (Table 1). Binding antibodies were measured as indicated in Materials and Methods. Each panel shows anti-Env IgA binding units (MFI) of individual NHPs. Plotting details are as described in FIG. 1, except IgA levels were log10-transformed.

Low levels of serum IgA specific to Env gp140 was detected in a few animals after the NYVAC-KC vaccinations, but was boosted most in G4 N2Cp2 when viewed as response rate (FIG. 2).

Figure 3:
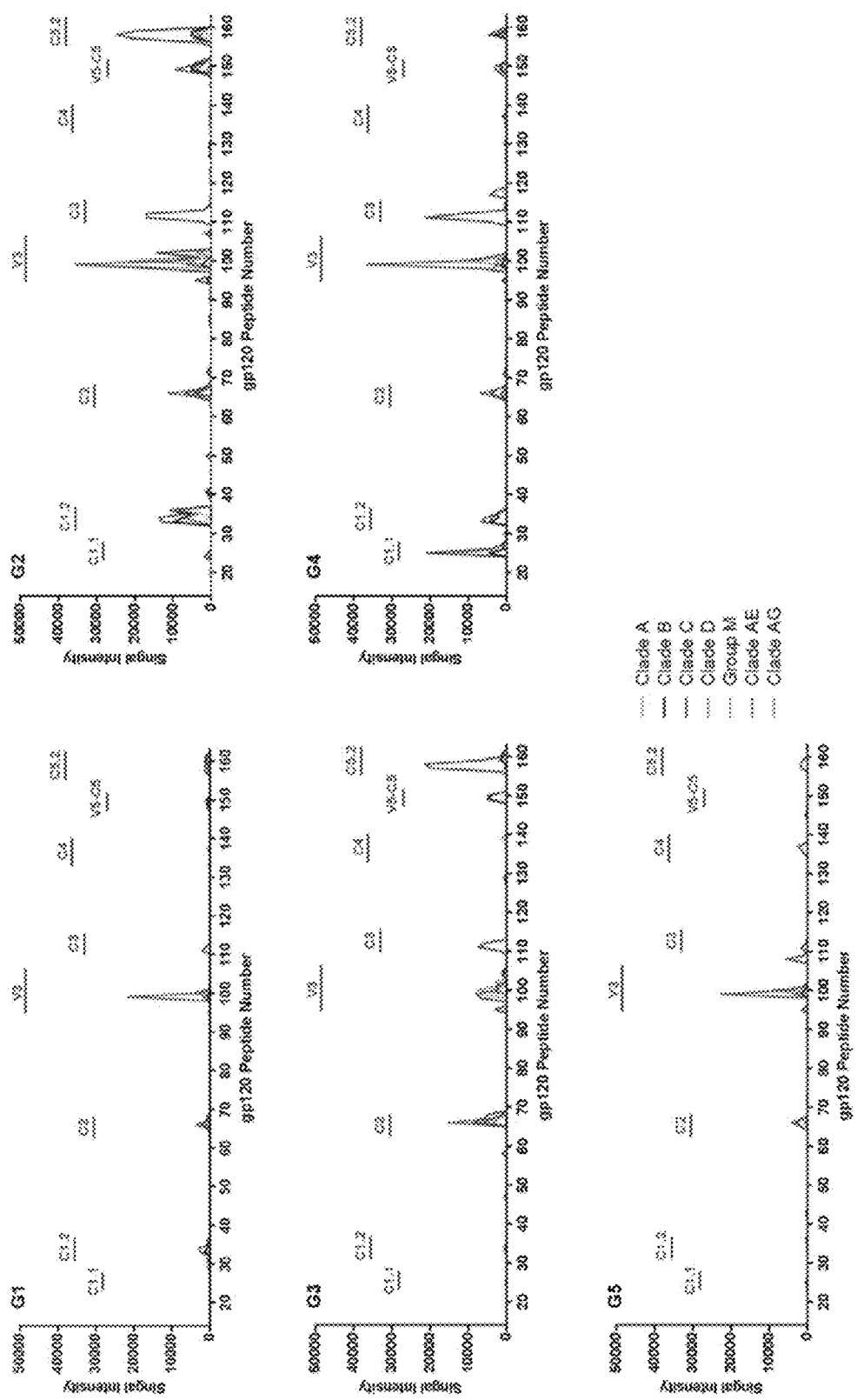
FIG. 3. Env gp120 epitope-specific IgG responses elicited by αLOX-1.Env gp140 and αCD40.Env gp140 fusion protein administration. A gp160 peptide array was probed with week 0 (for baseline) and week 26 (at peak response) plasma from 17 animals representing all 5 immunization groups, selected based on higher binding (per group) to ZM96 gp140 and/or 1086 V1V2 Tags. Three animals each were tested from Groups 1, 3, and 5, and four animals each were tested from Group 2 and 4. Mean binding values for each gp120 peptide are shown for group 1 to 5 (G1-G5). Data from vaccine strains for clade B (MN), clade C (TV1, 1086C and ZM651), and clade AE (A244 and TH023) are combined with the consensus of each to represent clade B, C, and AE, respectively. Epitope regions identified in the study are indicated with texts over horizontal bars in plots. Summary data for each epitope shown here are presented in Table 3.

Analysis of the breadth and magnitude of binding antibodies to linear epitopes was evaluated by peptide microarray mapping. Overall, the animals developed binding antibodies against gp120 linear epitopes C1, C2, V3, C3, C4, and C5, with V3 dominating the responses (FIG. 3). Linear binding responses were overall cross-clades, with a preference for Clade C sequences. The C5.2 response was focused on Clade C and the C3 response was restricted to C.ZM651, while the V3 and C1.2 binding was broader cross-clades (Table 3). The magnitude of binding trended higher in Groups G2 N2[CpN]2 and G4 N2Cp2 compared to Groups G1 N2[LpN]2, G3 N2Lp2 and G5 N2C25.

Figures 4A, 4B:
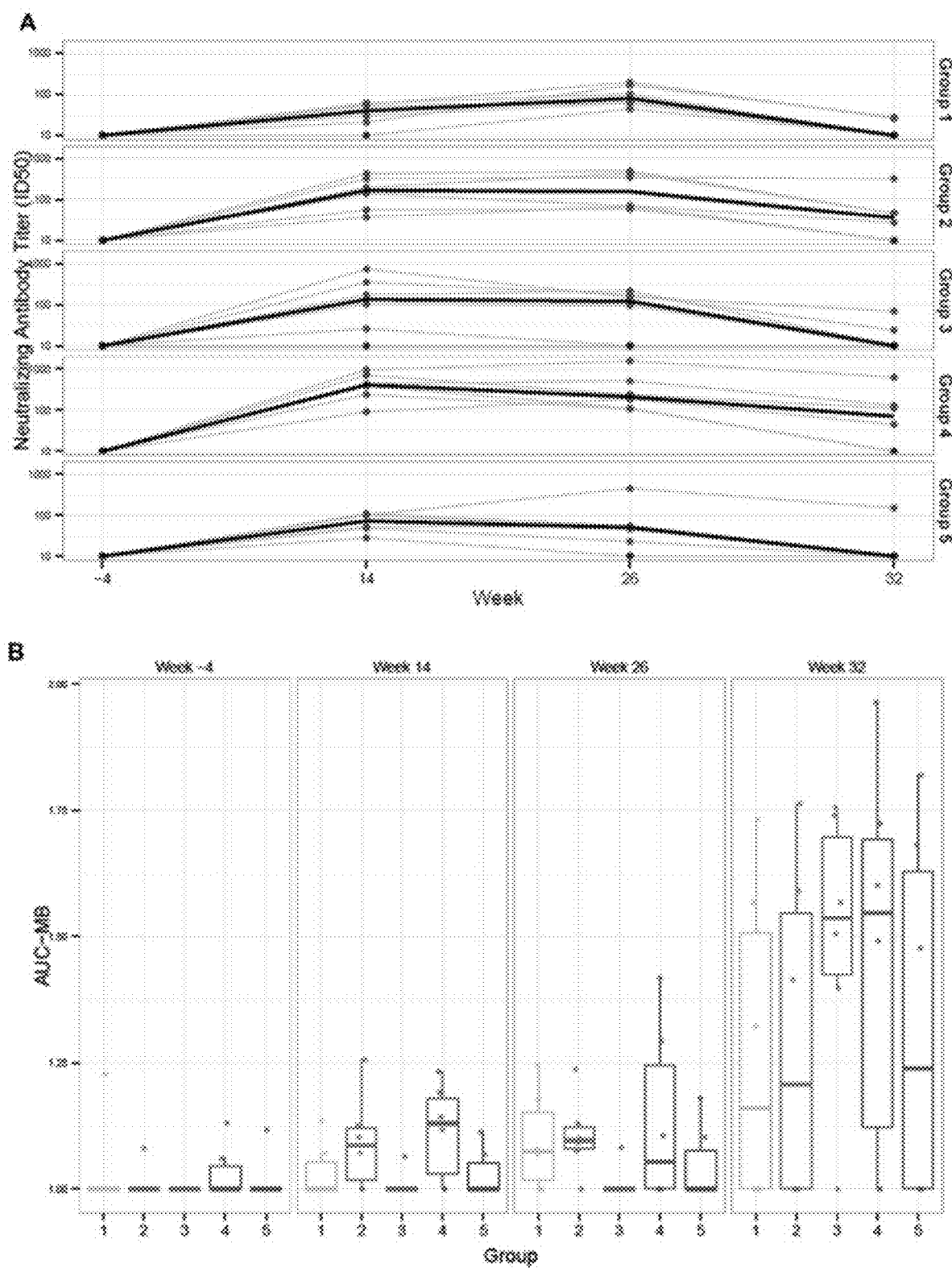
FIG. 4A-B. Serum neutralizing antibody responses elicited by αLOX-1.Env gp140 and αCD40.Env gp140 fusion protein administration. (A) Neutralizing antibodies against HIV-1 were measured as a function of reduction in Tat-regulated reporter gene expression in TZM-bl cells infected with HIV-1 isolate MW965. Neutralizing antibody titer values are ID50. Samples were tested from sera collected at weeks -4, 14, 26, and 32. Groups are indicated beside the graph. Each dot represents the value for one individual macaque. (B) The graph shows the area under MB curves (Material and Methods) used to summarize overall breadth and magnitude of neutralizing antibody activities against A3R5 virus for each individual time point. Samples were tested from sera collected at weeks -4, 14, 26, and 32. Groups are indicated below the graph. Table 4 shows analysis of paired comparisons of ID50 values for isolates MW965 and Th023.6.

Analysis of neutralizing activity in week 14, week 26, and week 32 plasma samples was performed via TZM.bl and A3R5 assays against a panel of Tier 1 and Tier 2 HIV-1 Env pseudotyped viruses. Neutralizing activity was detected against MW965.26 (clade C, Tier 1A, FIG. 4A) and TH023.6 (CRF01_AE, Tier 1A, not shown). Little or no neutralization was detected against Ce1086_B2, Ce1176_A3, C32010_F5, and DU151.2 viruses (data not shown). Also, no neutralization was detected against 96ZM651.2, Bal.26, CE1086_B2, MN.3, SF162.LS, TV1.21 or MLV (the control for nonspecific activity) (data not shown). Neutralization (NAb) titers against the sensitive viruses (MW965.26 and TH023.6) decreased somewhat from week 26 to week 32 in all groups. Group 4 N2Cp2 had significantly higher $ID_{50}$ titers to the sensitive viruses than other groups, as well as significantly higher $ID_50$ titers to MW965.26 than groups G1 N2(LpN)2 and G5 (N2C2), at weeks 14 and 26 (Table 4). At week 32, 8 weeks post completion of all vaccinations, G3 N2Lp2 and G4 N2Cp2 had the highest neutralizing scores based on individual-specific and group-specific magnitude-breadth (MB) analysis which measures the overall magnitude and breadth of NAb activities for each individual time point (FIG. 4B).

Figure 5:
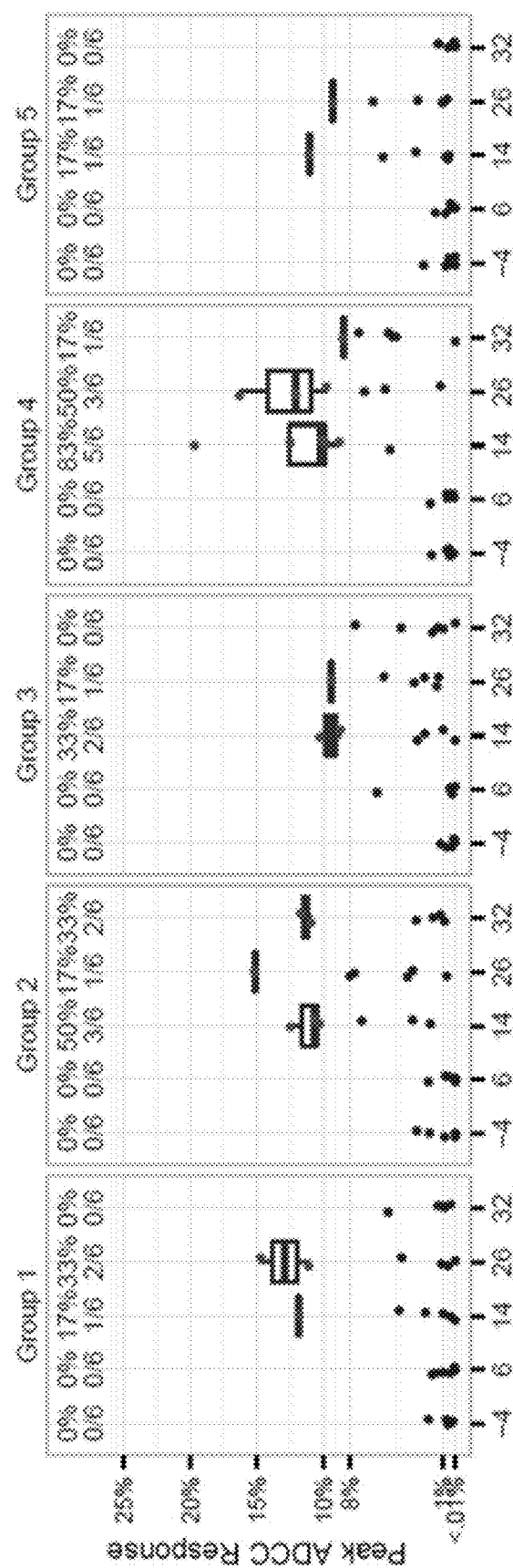
FIG. 5. ADCC-mediated antibody responses elicited by αLOX-1.Env gp140 and αCD40.Env gp140 fusion protein administration. ADCC-mediating serum antibodies were measured by the GranToxLux assay that measures percent granzyme B activity against HIV-Env protein-coated cells. Response rates are given at the top of each graph column.

Analysis of ADCC-mediated antibody responses in plasma samples collected at week −4, 14, 26, and 32 were measured via GranToxLux (GTL) assay. In all groups positive GTL responses were observed at week 14 and week 26, two weeks after the DC-targeting vaccine boosts. Group 4 (G4 N2Cp2) included more responses than other groups and positive GTL responses at week 32 were only observed in groups G2 N2(CpN)2 and G4 N2Cp2 (FIG. 5).

2. HIV-1 Env gp140 Targeted to Either LOX-1 or CD40 Elicits Env-Specific T Cell Responses in NHPs Primed with a Live Virus Vector.

Peripheral HIV-1 antigen-specific T cell responses to the vaccinations were evaluated by IFNγ ELISPOT analysis of PBMCs. Few or no responses were detected against Env gp140 antigen after the NYVAC-KC administrations, however the DC-targeting vaccine boost raised significant responses against Env gp140 in all animals in all groups except two of the six animals in G5 N2C2, and this included responses against all three Env subdomains sampled (FIG. 6). No significant responses were detected against other HIV-1 antigens represented in the NYVAC-KC Gag Nef Pol vector at any time points (not shown). In the pairwise comparisons G1 N2[LpN]2 vs. G3 N2Lp2 (i.e., LOX-1 targeting with and without co-administered NYVAC-KC) there were no significant differences in anti-Env T cell responses at weeks 26 or 32 (FIG. 6). However, in the pairwise comparisons G2 N2[CpN]2 vs. G4 N2Cp2 (i.e., CD40 targeting with and without co-administered NYVAC-KC) there were was a trend towards higher response with co-administered NYVAC-KC at week 26 (p=0.065) which became a significant difference (p=0.009) at week 32 (FIG. 6). In the pairwise comparison G4 N2Cp2 vs. G5 N2C2 (i.e., CD40 targeting with and without poly ICLC adjuvant) there was a trend to higher responses with poly ICLC (p=0.143 with 6/6 vs. 2/6 responders) at week 26, which became significant at week 32 (p=0.010 with 6/6 vs. 4/6 responders) (FIG. 6).

Peripheral HIV-1 antigen-specific CD4$^+$ T cell responses to the DC-targeting boost vaccinations (week 26 and 32) were also evaluated by intracellular cytokine staining (ICS) analysis of PBMCs. Low level responses were detected in some animals against HIV-1 antigens represented in the NYVAC-KC Gag Nef Pol vector at these sample times, but responses against Env antigens were higher in all groups and were positive in almost all animals (FIG. 7). In pairwise comparisons, there was a significant difference among responders to Env only between G4 (N2Cp2) and G5 (N2C2) (i.e., CD40 targeting with versus without poly ICLC adjuvant) at week 26 but not week 32 (p=0.004 and p=0.052; Mann-Whitney U P values). The CD4$^+$ T cell responses elicited by the DC-targeting vaccines were of a high quality as IFNγ, IL-2, and TNFα were detected in response to Env antigens (FIG. 7).

Peripheral HIV-1 antigen-specific CD8$^+$ T cell responses to the DC-targeting boost vaccinations (week 26 and 32) were also evaluated by ICS analysis of PBMCs. Low level responses were detected in some animals against HIV-1 antigens represented in the NYVAC-KC Gag Nef Pol vector at these sample times, but responses against Env antigens were generally higher for all groups (FIG. 8). In pairwise comparisons, there was a significant difference among responders to any protein only with G2 N2(CpN)2>G4 N2Cp2 at week 32 (p=0.029 Mann-Whitney U P value). High quality CD8$^+$ T cell responses (as measured by positive responders for IFNγ, IL-2, and TNFα) were especially evident in G2 N2(CpN)2 (FIG. 8). Unlike for CD4+ T cell responses, poly ICLC adjuvant did not benefit the development of Env-specific CD8+ T cell responses (see G4 (N2Cp2) versus G5 (N2C2), FIG. 8).

3. αCD40.Env gp140 Fusion Protein Elicits a More Durable Binding Antibody Response Compared to αLOX-1.Env gp140 Fusion Protein.

Durability of binding and neutralizing antibody responses were assessed by proportion of change per week, which was calculated as [(response at durability time point (wk32—response at peak time point (wk26))/response at peak time point (wk26)]/number of weeks between time points]. Durability was not evaluated for ADCC and T cell response (ICS) due to limited number of responders at the durability time point. Significant differences were observed in the rate of binding antibody response decline observed among the 5 groups of the current study (FIG. 9). Both groups with the αCD40.Env gp140 fusion protein trended for better binding response durability compared to the groups with αLOX-1.Env gp140 fusion protein, i.e., G2 N2[CpN]2>G1 N2[LpN]2 (trend) and G4 N2Cp2>G3 N2Lp2 (trend) for proportion of change per week (FIG. 9A). G4 N2Cp2 showed the best durability among the groups, with significantly slower decline of responses compared to G1 N2[LpN]2 and G5 N2C2 for binding to most gp140s including Con S gp140 CFI and C.con.env03 140 CF (P values 0.0056-0.018, 2-tailed t test) (Table 5). Durability for neutralization response was evaluated only for neutralization of MW965.26 (in TZM-bl cells), due to limited positive responders for other viruses at the durability time point. G4 N2Cp2 also trended for better neutralizing response durability compared to G3 N2Lp2 (FIG. 9B). No significant difference was observed among the groups for the rate of neutralization response decline (Table 5).

4. DC-Targeting Alters Both Humoral and Cellular Responses Compared to a Non-DC Targeted Env Boosting Regimen The current study did not have a control arm with non-DC-targeted Env gp140. However, a recent study (Garcia-Arriaza J, et al., J Virol 89:8525-8539) included a group of Rhesus macaques (called group 1 N2NP2 (C) in Garcia-Arriaza et al.; here called ExtNDC-N2[NP]2) that received the same 2 NYVAC-KC priming immunizations as in the current study, but boosted with non-DC-targeted Env gp120 (TV1 gp120+1086 gp120 in MF59, 100 µg total) administered together with NYVAC-KC at weeks 12 and 24. Also relevant is another recent study (Zurawski G, et al., PLoS One 11:e0153484) that included a group with the same 2 NYVAC-KC priming immunizations as in the current study, and boosted with the same αLOX-1.Env gp140+poly ICLC vaccine as the current study (called group 1 in 2; here called ExtDC-N2Lp3), except dosing of αLOX-1.Env gp140 was three times at weeks 12, 16, and 20 vs. twice at weeks 12 and 24 in the current study. Similar BAMA, neutralization, ADCC and ICS assays by the same laboratories were performed on those samples as were done for the current study.

Figure 10A:
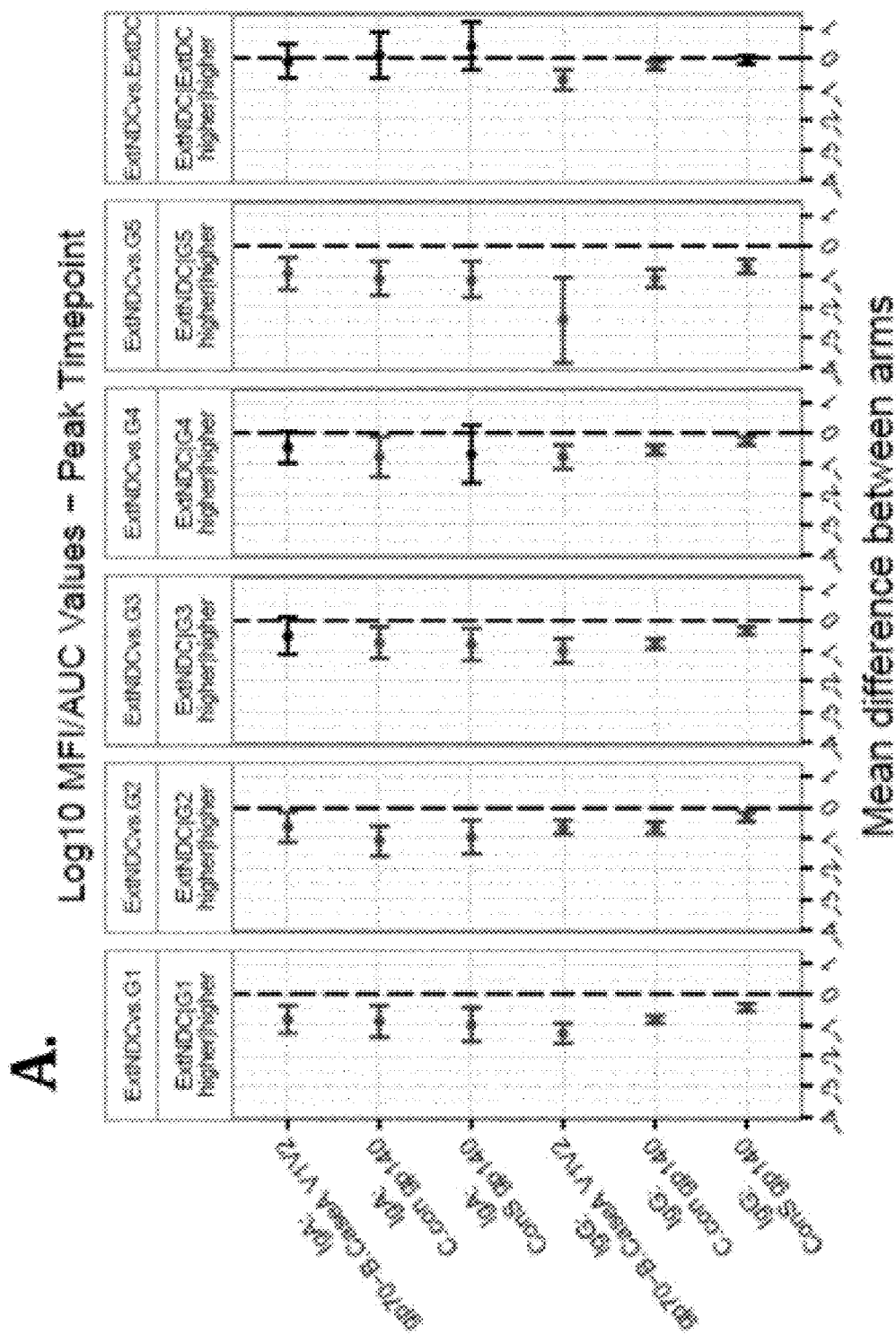
Figure 10B:
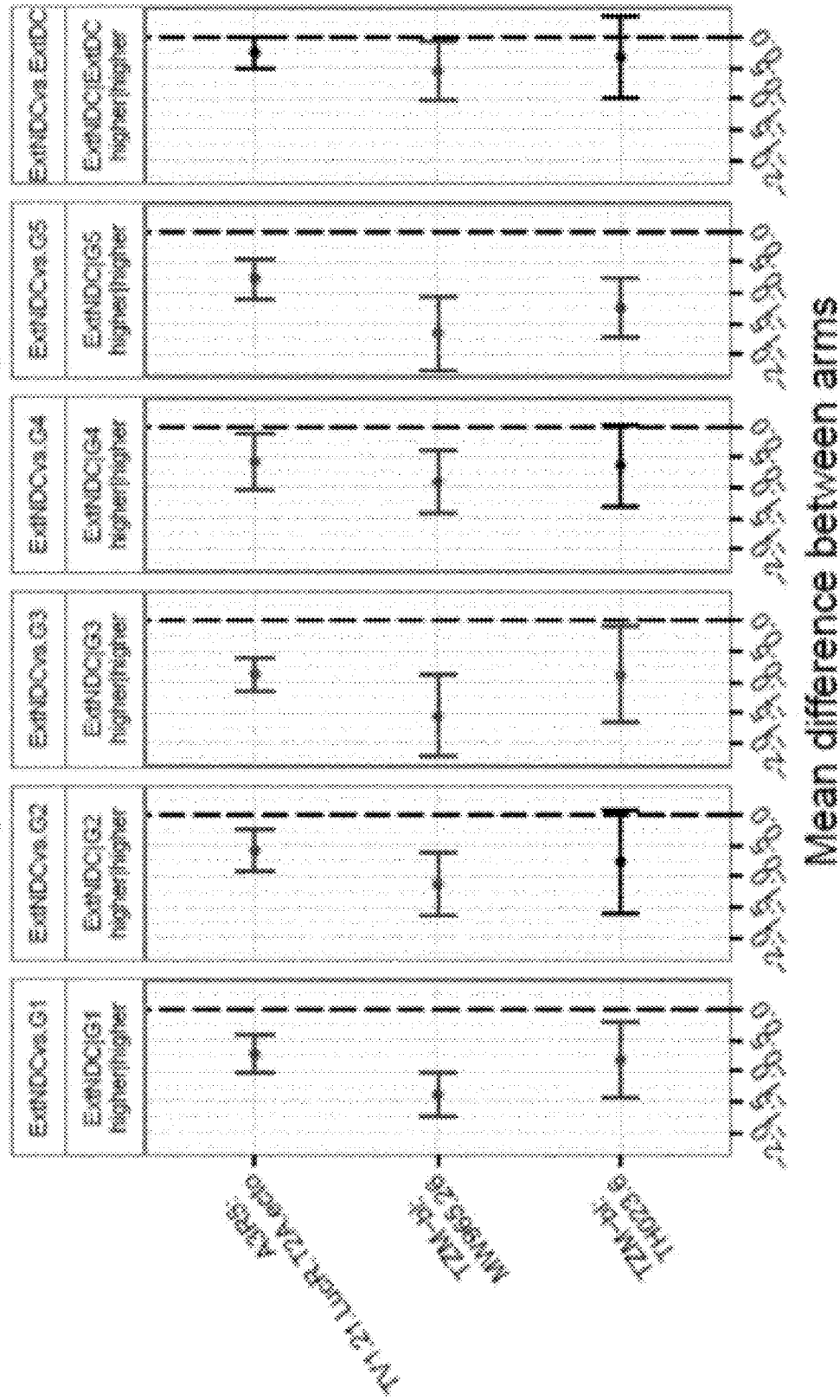
Figure 10C:
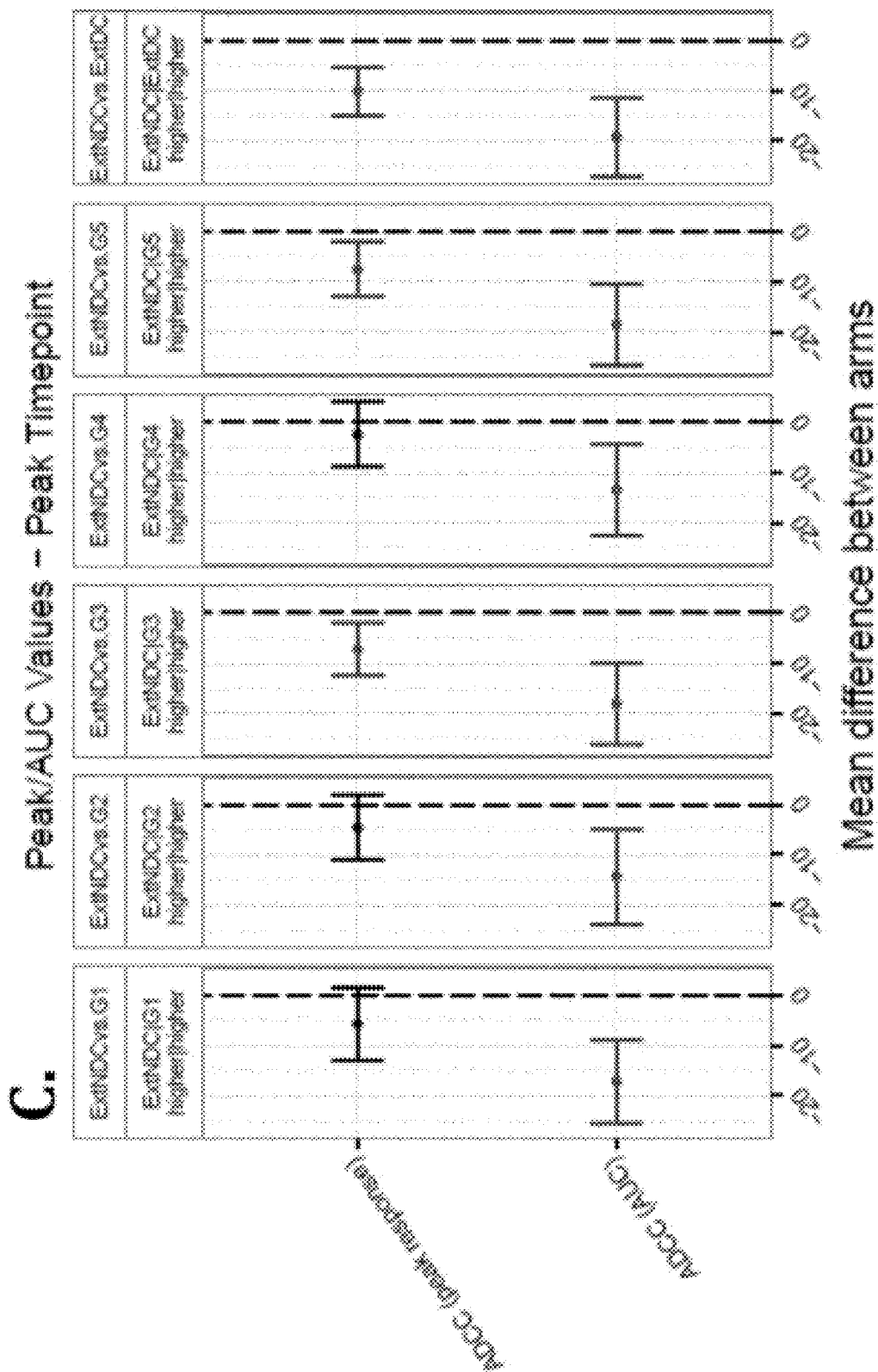
Figure 10D:
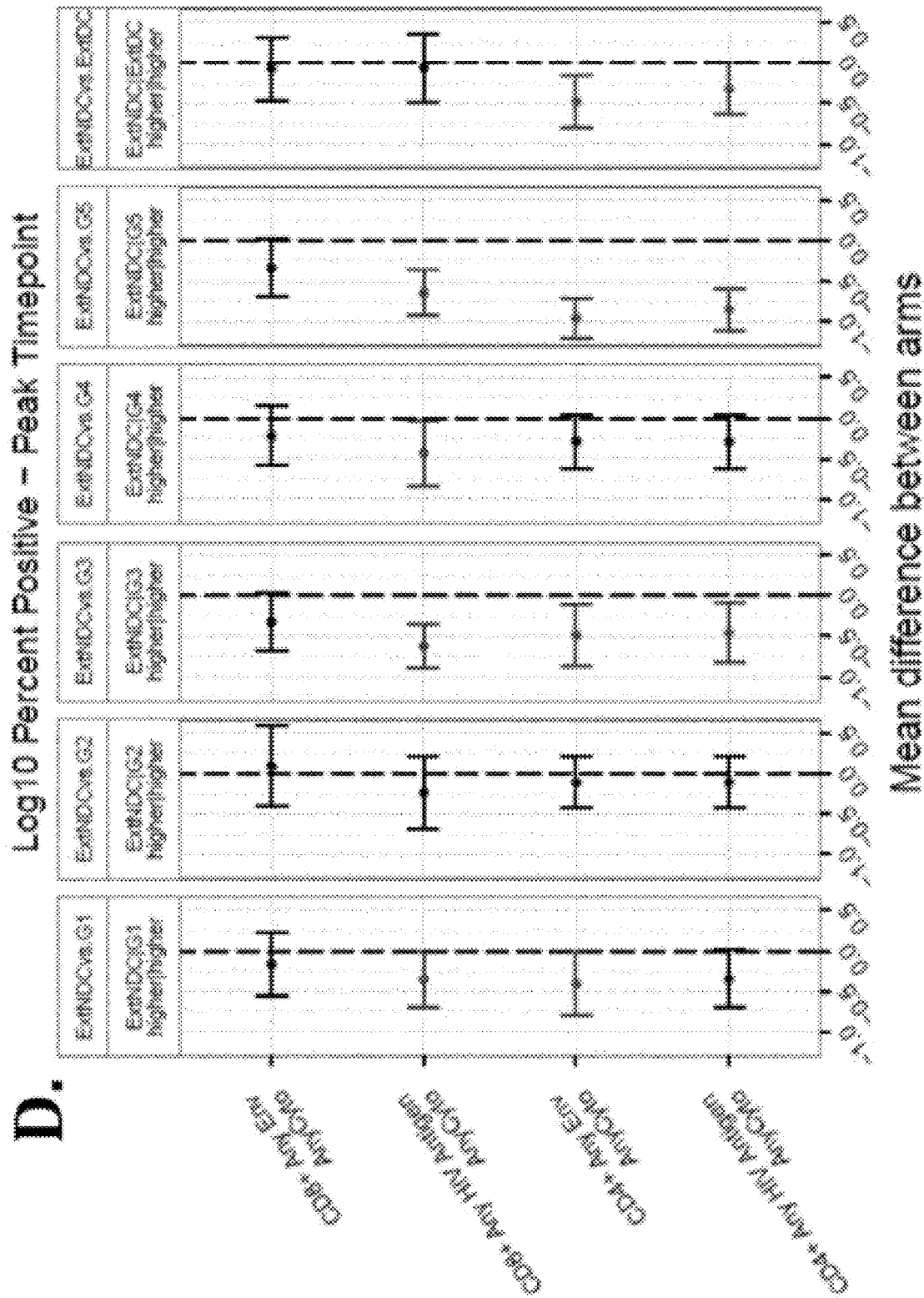

Therefore, we were able to compare immunogenicity data for the current study with data from the ExtNDC-N2[NP]2 and ExtDC-N2Lp3 immunization animals to gauge the effects of DC-targeting on the magnitude and durability of antibody responses and on the cellular response profiles, with the caveats that the adjuvant (i.e., MF59 vs. poly ICLC) and the antigens (i.e., gp120 TV1 gp120+1086 gp120 vs. gp140 Z96M) were different in the non-DC-targeted ExtNDC-N2[NP]2, and an additional dose of DC targeting vaccine was given in ExtDC-N2Lp3. These comparisons revealed that the non-DC-targeted Env (gp120) ExtNDC-N2[NP]2 immunization elicited considerably higher binding, neutralizing, and ADCC responses compared to the DC-targeting regimens in the current study at the peak immunity time point (week 26 for both studies). Both plasma IgG and IgA binding responses were significantly higher for the ExtNDC-N2[NP]2 group at week 26 (FIG. 10A; A Table 6). However, when the peak immunity time for ExtDC-N2Lp3 (same vaccine components as G3 of current study) was included in the analysis these differences were minimized. Binding response, and especially the IgA response, was significantly higher in the DCtargeting ExtDC-N2Lp3 group than G3, indicating that a third DC-targeting boost is advantageous (FIG. 10A; A Table 6). Similarly, neutralizing ID50 titers measured on TZM-bl cells and A3R5 cells against diverse virus targets were significantly higher in the ExtNDC-N2[NP]2 group than present study groups, although again the DC-targeting ExtDC-N2Lp3 group developed significantly higher neutralizing responses against two clade C strains TV1 and MW965 (FIG. 10B and Table 7), indicating an improvement of neutralizing response by a third boost. ADCC response measured with Env coated cells was significantly higher for the non-DC-targeted ExtNDC-N2[NP]2 compared to all 5 groups in the current study at week 26 and to the ExtDC-N2Lp3 (FIG. 10C and A Table 8). Despite the significantly higher antibody responses in the non-DC-targeting ExtNDCN2[NP]2 group compared to all 5 groups in the current study, differences in the levels of HIV-specific CD4+ and CD8+ T cell cytokine secreting responses were not as significant (FIG. 10D). The proportions of CD4+ T cells that express any of the 3 cytokines tested for the ExtNDC-N2 [NP]2 was comparable with the G1 (for any HIV antigen stimulation), G2, and G4 groups in current study (Table 9), though significantly higher than G3, G5 and ExtDC groups (P<0.0001 to 0.046). Meanwhile, G2 and the ExtNDC groups showed CD8+ T cell response comparable to that of the ExtDN group upon any Env antigen stimulation, and all groups from current study, and the ExtDC group, developed CD8+ T cell responses comparable to that of the ExtNDC group upon any Env stimulation (Table 9). In addition, the ExtDC group developed T cell responses significantly higher than G3 group in current study except for CD4+ response upon any Env stimulation, demonstrating the beneficial effect of the additional boost for T cell response as well. Durability for the external non-DC-targeted Env gp120 group (Ext-N2[NP]2) group was also evaluated. Durability time point was not available for the ExtDC-N2Lp3 group in these same assays, and therefore durability was not analyzed for that group. The peak time point was also week 26 for ExtNDC-N2[NP]2, whereas the durability time point was week 36 (12 weeks post the 4th immunization) instead of week 32 in current study. Comparison of proportion of change per week revealed generally better durability of binding and neutralizing responses in the ExtNDC-N2[NP]2 (FIG. 11; Tables 10 and 11). ExtNDC group showed significantly better durability compared to G1 N2[LpN]2 for all gp140s tested, significantly higher than G3 N2Lp2 and G5 N2C2 for most of the gp140s tested (P values ranged from <0.0001 to 0.034, 2-tailed t-test) (Table 10), and significantly higher durability for binding to gp70.B.CaseA V1V2 scaffold compared to G1 N2[LpN]2 and G3 N2Lp2 (P=0.007). However, no significant difference was found between ExtNDC-N2[NP]2 and either G2 N2[CpN]2 or G4 N2Cp2 for binding to any antigens (FIG. 11, Table 10), reflecting the advantage of CD40 targeting for durability noted above. Durability of neutralizing response (proportion of change per week) for G2 N2[CpN]2 and G3 N2Lp2 compared to the non-DC-targeting group was not significantly different, but ExtNDC-N2[NP]2 was higher compared to G1 N2[LpN]2, G4 N2Cp2, G5 N2C2, and ExtDC groups (FIG. 11, Table 11). One caveat of comparing the durability of DC-targeting groups in the current study and the non-DC-targeting ExtNDC-N2[NP]2 by proportion of change per week was the unequal time (weeks) between the peak and durability time points of the 2 studies. It has been shown that the decline of antibody responses after vaccination is at different rates over time, with a much faster initial decline (36). The current study had only 6 weeks between the 2 time points, whereas in the ExtNDC-N2[NP]2 study there was a 10 weeks interval. It is possible that by calculating proportion of change per week, the durability analysis gave the non-DC-targeted ExtNDC-N2[NP]2 a biased advantage; while the durability of the DC-targeting groups in the current study relative to the non-DCtargeting ExtNDC-N2[NP]2 could in fact be higher.

C. Tables

TABLE 1

Study design for testing antigenicity of αLOX-1.Env gp140 and αCD40.Env gp140 fusion proteins in NHP

| Group | Size | Week 0 | Week 4 | Week 12 | Week 24 |
|---|---|---|---|---|---|
| G1 N2[LpN]2 | 6 | NYVAC-KC | NYVAC-KC | NYVAC-KC + αLOX-1/poly ICLC | NYVAC-KC + αLOX-1/poly ICLC |
| G2 N2[CpN]2 | 6 | NYVAC-KC | NYVAC-KC | NYVAC-KC + αCD40/poly ICLC | NYVAC-KC + αCD40/poly ICLC |
| G3 N2Lp2 | 6 | NYVAC-KC | NYVAC-KC | αLOX-1/poly ICLC | αLOX-1/poly ICLC |
| G4 N2Cp2 | 6 | NYVAC-KC | NYVAC-KC | αCD40/poly ICLC | αCD40/poly ICLC |
| G5 N2C2 | 6 | NYVAC-KC | NYVAC-KC | αCD40 | αCD40 |

| | Week | | | | | | |
|---|---|---|---|---|---|---|---|
| | −4 | 0 | 2 | 4 | 6 | 14 | 26 | 32 |
| Vaccination (V) | | V | | V | V | V | V |
| Serum Collection (A) | A | A | A | A | A | A | A |
| Blood Collection (E) | E | E | E | | E | E | E | E |
| Frozen PBMC preparation (P) | P | | | | P | P | P | P |

$1^a$ The immunization regimens used in this study.
The reference codes for the five vaccination groups are:
N = NYVAC-KC,
L = αLOX-1.Env gp140,
p = poly ICLC,
2 = administered twice in sequence.
NYVAC-KC administration was i.m., DC-targeting protein administration was intradermal (i.d.), and poly ICLC administration was subcutaneous (s.c.) in proximity to the protein.
The cells below are in biweekly increments starting at week −4 through week 32.
V indicates vaccination dates;
A denotes serum collection for antibody response determination;
E denotes blood collection for IFNγ ELISPOT measurements; and
P denotes frozen PBMC preparation for antigen-specific T cell analysis via flow cytometry including intracellular cytokine staining.

TABLE 2

Comparison between paired groups for plasma IgG binding magnitudes.

| Antigen Group | Antigen | Week | Group2-1 | Group3-1 | Group4-2 | Group4-3 | Group5-4 |
|---|---|---|---|---|---|---|---|
| gp140 | 00MSA 4076 gp140 | 26 | 4144 (0.18) | **5109 (0.03\*)** | 8073 (0.24) | 7108 (0.48) | −14514 (<0.01\*\*) |
| | | 32 | 3358 (0.09) | **2252 (0.03\*)** | 3866 (0.31) | 4971 (0.24) | −7798 (**<0.01\*\***) |
| gp140 | A1.con.env03 140 CF | 26 | 3351 (0.18) | 3788 (0.13) | 4927 (0.18) | **4490 (0.04\*)** | −14802 (<0.01\*\*) |
| | | 32 | 3331 (0.09) | 3464 (0.06) | 6745 (0.18) | 6612 (0.06) | −11775 (<0.01\*\*) |
| gp140 | B.con.env03 140 CF | 26 | 7901 (0.24) | 1156 (0.48) | −1150 (1) | 5595 (0.24) | −15361 (<0.01\*\*) |
| | | 32 | 2943 (0.18) | 1360 (0.31) | 2417 (0.7) | **4000 (0.04\*)** | −7386 (**<0.01\*\***) |
| gp140 | C.con.env03 140 CF avi | 26 | 3404 (0.13) | 1347 (0.82) | 4133 (0.31) | 6190 (0.18) | −10920 (<0.01\*\*) |
| | | 32 | 1694 (0.18) | 1502 (0.31) | 6995 (0.24) | **7187 (0.03\*)** | −11436 (<0.01\*\*) |
| gp140 | Con S gp140 CFI | 26 | 5861 (0.24) | 2225 (0.24) | −1879 (0.7) | 1757 (0.39) | −13036 (<0.01\*\*) |
| | | 32 | 2517 (0.31) | 3443 (0.13) | 9369 (0.39) | 8444 (0.18) | −17893 (<0.01\*\*) |
| gp140 | ZM96 gp140-Ctag | 26 | 9319 (0.09) | 2786 (0.48) | 4198 (0.24) | 10731 (0.13) | −23761 (<0.01\*\*) |
| | | 32 | 7596 (0.09) | 5197 (0.59) | 9296 (0.31) | **11695 (0.03\*)** | −25617 (<0.01\*\*) |

TABLE 2-continued

Comparison between paired groups for plasma IgG binding magnitudes.

| Antigen Group | Antigen | Week | Group2-1 | Group3-1 | Group4-2 | Group4-3 | Group5-4 |
|---|---|---|---|---|---|---|---|
| V1V2 | AE.A244 V1V2 | 26 | 2 (0.59) | 2 (0.59) | −210 (0.09) | −210 (0.13) | −9 (0.7) |
|  |  | 32 | −4 (0.87) | 10 (0.63) | 0 (0.69) | −14 (0.81) | −1 (0.94) |
| V1V2 | AE.A244 V2 tags 293F | 26 | 373 (0.18) | −14 (0.82) | −444 (0.13) | −57 (0.69) | 4 (0.94) |
|  |  | 32 | 43 (0.42) | 9 (0.7) | −45 (0.38) | −11 (0.57) | 12 (0.57) |
| V1V2 | C.1086 V2 tags 293F | 26 | −5 (0.82) | 19 (0.94) | −20 (0.75) | −45 (0.75) | 3 (0.82) |
|  |  | 32 | 24 (0.87) | 36 (0.59) | −11 (0.63) | −22 (0.09) | −12 (0.87) |
| V1V2 | C.1086C V1 V2 Tags | 26 | 10284 (0.13) | 2331 (0.7) | −11860 (0.06) | −3906 (0.39) | −1500 (0.39) |
|  |  | 32 | 2843 (0.13) | 741 (0.59) | −2394 (0.39) | −291 (1) | −1419 (0.31) |
| V1V2 | gp70 B.CaseA V1 V2 | 26 | **7836 (<0.01\*\*)** | 2879 (0.18) | −708 (0.7) | 4249 (0.39) | **−8507 (0.02\*)** |
|  |  | 32 | **2318 (0.02\*)** | 809 (0.18) | 2951 (0.24) | **4460 (0.04\*)** | **−5629 (<0.01\*\*)** |

Test results shown are median difference between groups followed by p value in parentheses [median of differences (p values)]. P values are from Wilcoxon rank sum test. Values for comparison are AUC values as measured in BAMA (Materials and Methods) and shown in FIG. 1. Groups are G1 N2[LpN]2, G2 N2[CpN]2, G3 N2Lp2, G4 N2Cp2 and G5 N2C2 (Table 1). Significant differences are bolded and indicated by * for $p<0.05$ and ** for $p<0.01$.

TABLE 3

Binding magnitude to linear epitopes by plasma IgG from Group 1-5 animals at the peak response time point (week 26).

| Group | Boost | Animal | C1.1 23-27 | C1.2 33-36 | C2 65-68 | V3 95-106 | C3 111-112 | C4 135-139 | V5-C5 148-152 | C5.2 157-162 | gp41 ID 187-189 |
|---|---|---|---|---|---|---|---|---|---|---|---|
| 1 | NYVAC-KC+ aLox/PolyICLC | R734 | 97 | 2,830 | 202 | 4,616 | 2,686 | 1 | 573 | 1,139 | 1 |
|  |  | R745 | 54 | 3,567 | 154 | 14,430 | 1 | 1 | 2,838 | 269 | 1 |
|  |  | R758 | 1 | 4,582 | 10,900 | 47,715 | 3,074 | 1,747 | 565 | 3,937 | 1 |
| 2 | NYVAC-KC+ aLox/PolyICLC | R730 | 1 | 17,417 | 7,308 | 5,314 | 125 | 151 | 1 | 45,165 | 1 |
|  |  | R746 | 6,411 | 41,288 | 15,138 | 51,380 | 55,490 | 1,779 | 32,849 | 61,527 | 24,886 |
|  |  | R755 | 2,311 | 1 | 17,920 | 36,921 | 13,187 | 1 | 5,040 | 133 | 1 |
|  |  | R756 | 1 | 10,337 | 3,976 | 61,649 | 537 | 1 | 579 | 1,728 | 377 |
| 3 | aLox/PoluICLC | R731 | 1 | 482 | 40,485 | 22,175 | 3,355 | 3,661 | 39 | 20,533 | 1 |
|  |  | R739 | 1 | 147 | 1,030 | 1,056 | 1,013 | 733 | 14,977 | 6,623 | 1 |
|  |  | R749 | 878 | 1,194 | 4,168 | 3,796 | 17,472 | 13 | 509 | 43,939 | 1 |
| 4 | aCD40/PolyICLC | R736 | 209 | 10,941 | 12,794 | 21,838 | 19,495 | 1,578 | 1,960 | 8,829 | 1 |
|  |  | R741 | 2,821 | 1 | 3,809 | 38,028 | 6,963 | 1 | 15 | 795 | 1 |
|  |  | R748 | 65,300 | 14,777 | 7,002 | 31,993 | 9,670 | 2,705 | 8,433 | 8,244 | 682 |
|  |  | R754 | 15,305 | 2,565 | 3,304 | 65,297 | 49,294 | 497 | 2,339 | 6,115 | 17,375 |
| 5 | aCD40 | R732 | 1,820 | 189 | 4,235 | 12,947 | 1 | 5,352 | 1 | 5,218 | 1 |
|  |  | R737 | 243 | 355 | 8,480 | 4,639 | 3,836 | 2,574 | 50 | 1 | 1 |
|  |  | R759 | 1 | 821 | 1 | 62,969 | 1,046 | 1 | 168 | 1 | 1 |

Epitope regions for gp120 are as shown graphically in FIG. 3 and here include data for the gp41 immunodominant (ID) region. Magnitude shown here are maximum binding=per epitope, which is calculated as the highest signal intensity to a single peptide within a given epitope region. Data in the table are bolded with higher values in bold. The rank order in higher values was G4 N2Cp2 (n=16), G2 N2[CpN]2 (n=14), G3 N2Lp2 (n=6), G1 N2[LpN]2/G5 N2C2 (n=3).

TABLE 4

Comparison between paired groups for serum neutralizing responses.

| Comparison | Assay Type | Isolate | Week. 14 | Week. 26 | Week. 32 |
|---|---|---|---|---|---|
| Grp2-1 | TZM-bl | t.mw965 | 130 (0.037*) | 129 (0.261) | 27 (0.145) |
|  |  | t.th023 | 0 (0.462) | −16 (1) | 0 (0.462) |
| Grp3-1 | TZM-bl | t.mw965 | 98 (0.199) | 42 (1) | 0 (1) |
|  |  | t.th023 | 0 (0.462) | −16 (0.655) | 0 (0.405) |
| Grp4-1 | TZM-bl | t.mw965 | **372 (0.005*)** | **130 (0.045*)** | 68 (0.104) |
|  |  | t.th023 | 0 (0.599) | 20 (0.561) | 0 (0.462) |

TABLE 4-continued

Comparison between paired groups for serum neutralizing responses.

| Comparison | Assay Type | Isolate | Week. 14 | Week. 26 | Week. 32 |
|---|---|---|---|---|---|
| Grp5-1 | TZM-bl | t.mw965 | 35 (0.199) | −32 (0.173) | 0 (0.753) |
| | | t.th023 | 0 (0.599) | −16 (0.074) | 0 (0.405) |
| Grp3-2 | TZM-bl | t.mw965 | −32 (0.81) | −86 (0.378) | −27 (0.266) |
| | | t.th023 | 0 (0.775) | 0 (1) | 0 (0.176) |
| Grp4-2 | TZM-bl | t.mw965 | 242 (0.093) | 1 (0.378) | 41 (0.683) |
| | | t.th023 | 0 (1) | 36 (0.798) | 0 (1) |
| Grp5-2 | TZM-bl | t.mw965 | −94 (0.128) | **−160 (0.045*)** | −27 (0.18) |
| | | t.th023 | 0 (1) | 0 (0.176) | 0 (0.176) |
| Grp4-3 | TZM-bl | t.mw965 | 274 (0.173) | 88 (0.092) | 68 (0.146) |
| | | t.th023 | 0 (0.924) | 36 (0.347) | 0 (0.176) |
| Grp5-3 | TZM-bl | t.mw965 | −62 (0.471) | −74 (0.687) | 0 (0.753) |
| | | t.th023 | 0 (0.924) | 0 (0.176) | 0 (NaN) |
| Grp5-4 | TZM-bl | t.mw965 | **−336 (0.02*)** | **−162 (0.031*)** | −68 (0.181) |
| | | t.th023 | 0 (1) | **−36 (0.028*)** | 0 (0.176) |

Test results shown are median difference between groups followed by p value in parentheses [median of differences (p values)]. Analysis was by t-test assuming unequal variance between groups and calculated P values are indicated in parentheses. Values used for comparison are serum $ID_{50}$ titers as shown in FIG. 4. Significant differences (p<0.05) are bolded and indicated by *. Groups are G1 N2[LpN]2, G2 N2[CpN]2, G3 N2Lp2, G4 N2Cp2 and G5 N2C2.

TABLE 5

Analysis of paired comparisons of serum $ID_{50}$ values.

| Response Tested | Comparison | Magnitude Stats | p Value |
|---|---|---|---|
| IgG: C.con.env03 140 CF | G1 vs. G2 | −0.091 (0.028) vs. −0.045 (0.067) | 0.168 |
| | G1 vs. G3 | −0.091 (0.028) vs. −0.069 (0.029) | 0.214 |
| | G1 vs. G4 | −0.091 (0.028) vs. −0.041 (0.014) | 0.006** |
| | G1 vs. G5 | −0.091 (0.028) vs. −0.092 (0.035) | 0.930 |
| | G2 vs. G3 | −0.045 (0.067) vs. −0.069 (0.029) | 0.447 |
| | G2 vs. G4 | −0.045 (0.067) vs. −0.041 (0.014) | 0.907 |
| | G2 vs. G5 | −0.045 (0.067) vs. −0.092 (0.035) | 0.165 |
| | G3 vs. G4 | −0.069 (0.029) vs. −0.041 (0.014) | 0.073 |
| | G3 vs. G5 | −0.069 (0.029) vs. −0.092 (0.035) | 0.236 |
| | G4 vs. G5 | −0.041 (0.014) vs. −0.092 (0.035) | 0.0142* |
| IgG: Con S gp140 CFI | G1 vs. G2 | −0.097 (0.025) vs. −0.057 (0.061) | 0.180 |
| | G1 vs. G3 | −0.097 (0.025) vs. −0.075 (0.024) | 0.153 |
| | G1 vs. G4 | −0.097 (0.025) vs. −0.052 (0.031) | 0.0182* |
| | G1 vs. G5 | −0.097 (0.025) vs. −0.108 (0.028) | 0.488 |
| | G2 vs. G3 | −0.057 (0.061) vs. −0.075 (0.024) | 0.519 |
| | G2 vs. G4 | −0.057 (0.061) vs. −0.052 (0.031) | 0.856 |
| | G2 vs. G5 | −0.057 (0.061) vs. −0.108 (0.028) | 0.103 |
| | G3 vs. G4 | −0.075 (0.024) vs. −0.052 (0.031) | 0.171 |
| | G3 vs. G5 | −0.075 (0.024) vs. −0.108 (0.028) | 0.054 |
| | G4 vs. G5 | −0.052 (0.031) vs. −0.108 (0.028) | 0.007** |
| IgG: gp70.B.CaseA V1.V2 | G1 vs. G2 | −0.139 (0.036) vs. −0.107 (0.034) | 0.153 |
| | G1 vs. G3 | −0.139 (0.036) vs. −0.125 (0.029) | 0.492 |
| | G1 vs. G4 | −0.139 (0.036) vs. −0.064 (0.081) | 0.081 |
| | G1 vs. G5 | −0.139 (0.036) vs. −0.142 (0.041) | 0.915 |
| | G2 vs. G3 | −0.107 (0.034) vs. −0.125 (0.029) | 0.352 |
| | G2 vs. G4 | −0.107 (0.034) vs. −0.064 (0.081) | 0.272 |
| | G2 vs. G5 | −0.107 (0.034) vs. −0.142 (0.041) | 0.292 |
| | G3 vs. G4 | −0.125 (0.029) vs. −0.064 (0.081) | 0.134 |
| | G3 vs. G5 | −0.125 (0.029) vs. −0.142 (0.041) | 0.575 |
| | G4 vs. G5 | −0.064 (0.081) vs. −0.142 (0.041) | 0.101 |
| Neutralization: MW965.26 | G1 vs. G2 | −0.14 (0.007) vs. −0.116 (0.054) | 0.327 |
| | G1 vs. G3 | −0.14 (0.007) vs. −0.136 (0.031) | 0.790 |
| | G1 vs. G4 | −0.14 (0.007) vs. −0.124 (0.026) | 0.184 |
| | G1 vs. G5 | −0.14 (0.007) vs. −0.122 (0.018) | 0.088 |
| | G2 vs. G3 | −0.116 (0.054) vs. −0.136 (0.031) | 0.486 |
| | G2 vs. G4 | −0.116 (0.054) vs. −0.124 (0.026) | 0.760 |
| | G2 vs. G5 | −0.116 (0.054) vs. −0.122 (0.018) | 0.817 |
| | G3 vs. G4 | −0.136 (0.031) vs. −0.124 (0.026) | 0.546 |
| | G3 vs. G5 | −0.136 (0.031) vs. −0.122 (0.018) | 0.461 |
| | G4 vs. G5 | −0.124 (0.026) vs. −0.122 (0.018) | 0.881 |

Test results shown are median difference between groups followed by p value in parentheses [median of differences (p values)]. Analysis was by t-test assuming unequal variance between groups and calculated P values are indicated in parentheses. Values used for comparison are plasma binding AUC (as shown in FIG. 3) and serum neutralization $ID_{50}$ titers measured on TZM-bl cells (as shown in FIG. 4). Groups are G1 N2[LpN]2, G2 N2[CpN]2, G3 N2Lp2, G4 N2Cp2 and G5 N2C2 (Table 1). Significant differences are bolded and indicated by * for p<0.05 and ** for p<0.01.

TABLE 6

BAMA peak time point IgG (AUC) and IgA (MFI) magnitude pairwise comparison of non-DC targeting ExtNDC-N2[NP]2 against DC-targeted groups (G1 to G5 and ExtDC in the current study and ExtDC-N2Lp3) as well as ExtDC against G3.

| Isotype | Analyte | Comparison | Mean (SD) | p Value |
|---|---|---|---|---|
| IgG | 00MSA 4076 gp140 | ExtNDC vs. G1 | 29184 (9567) vs. 5334 (4248) | p = 0.0567 |
| IgG | 00MSA 4076 gp140 | ExtNDC vs. G2 | 29184 (9567) vs. 11097 (7232) | p = 0.0099 |
| IgG | 00MSA 4076 gp140 | ExtNDC vs. G3 | 29184 (9567) vs. 11454 (4469) | p = 0.0006 |
| IgG | 00MSA 4076 gp140 | ExtNDC vs. G4 | 29184 (9567) vs. 14785 (4803) | p = 0.0078 |
| IgG | 00MSA 4076 gp140 | ExtNDC vs. G5 | 29184 (9567) vs. 2729 (1299) | p < 0.0001 |
| IgG | 00MSA 4076 gp140 | ExtNDC vs. ExtDC | 29184 (9567) vs. 16819 (5849) | p = 0.016 |
| IgG | 00MSA 4076 gp140 | G3 vs. ExtDC | 11454 (4470) vs. 16819 (5850) | p = 0.0934 |
| IgG | A1.con.env03 140 CF | ExtNDC vs. G1 | 39323 (8491) vs. 11416 (4205) | p = 0.0002 |
| IgG | A1.con.env03 140 CF | ExtNDC vs. G2 | 39323 (8491) vs. 16951 (7958) | p = 0.0022 |
| IgG | A1.con.env03 140 CF | ExtNDC vs. G3 | 39323 (8491) vs. 14794 (3346) | p < 0.0001 |
| IgG | A1.con.env03 140 CF | ExtNDC vs. G4 | 39323 (8491) vs. 21629 (5953) | p = 0.001 |
| IgG | A1.con.env03 140 CF | ExtNDC vs. G5 | 39323 (8491) vs. 6165 (4560) | p = 0.0006 |
| IgG | A1.con.env03 140 CF | ExtNDC vs. ExtDC | 39323 (8491) vs. 30388 (9128) | p = 0.1032 |
| IgG | A1.con.env03 140 CF | G3 vs. ExtDC | 14794 (3346) vs. 30388 (9128) | p = 0.002 |
| IgG | B.con.env03 140 CF | ExtNDC vs. G1 | 30978 (8615) vs. 12795 (5496) | p = 0.0027 |
| IgG | B.con.env03 140 CF | ExtNDC vs. G2 | 30978 (8615) vs. 19517 (9387) | p = 0.107 |
| IgG | B.con.env03 140 CF | ExtNDC vs. G3 | 30978 (8615) vs. 16564 (6097) | p = 0.0047 |
| IgG | B.con.env03 140 CF | ExtNDC vs. G4 | 30978 (8615) vs. 20783 (5844) | p = 0.0267 |
| IgG | B.con.env03 140 CF | ExtNDC vs. G5 | 30978 (8615) vs. 4440 (1466) | p < 0.0001 |
| IgG | B.con.env03 140 CF | ExtNDC vs. ExtDC | 30978 (8615) vs. 21725 (8919) | p = 0.0549 |
| IgG | B.con.env03 140 CF | G3 vs. ExtDC | 16564 (6097) vs. 21725 (8919) | p = 0.2137 |
| IgG | C.con.env03 140 CF | ExtNDC vs. G1 | 52906 (8011) vs. 8408 (2278) | p < 0.0001 |
| IgG | C.con.env03 140 CF | ExtNDC vs. G2 | 52906 (8011) vs. 11801 (4445) | p = 0.0002 |
| IgG | C.con.env03 140 CF | ExtNDC vs. G3 | 52906 (8011) vs. 9702 (3497) | p < 0.0001 |
| IgG | C.con.env03 140 CF | ExtNDC vs. G4 | 52906 (8011) vs. 14968 (5298) | p = 0.0002 |
| IgG | C.con.env03 140 CF | ExtNDC vs. G5 | 52906 (8011) vs. 4996 (2451) | p = 0.0001 |
| IgG | C.con.env03 140 CF | ExtNDC vs. ExtDC | 52906 (8011) vs. 31053 (7462) | p = 0.0019 |
| IgG | C.con.env03 140 CF | G3 vs. ExtDC | 9702 (3497) vs. 31053 (7462) | p = 0.0001 |
| IgG | Con S gp140 CFI | ExtNDC vs. G1 | 48885 (7813) vs. 17947 (4889) | p = 0.0001 |
| IgG | Con S gp140 CFI | ExtNDC vs. G2 | 48885 (7813) vs. 23372 (7345) | p = 0.0027 |
| IgG | Con S gp140 CFI | ExtNDC vs. G3 | 48885 (7813) vs. 22509 (6103) | p = 0.0002 |
| IgG | Con S gp140 CFI | ExtNDC vs. G4 | 48885 (7813) vs. 27231 (8472) | p = 0.0027 |
| IgG | Con S gp140 CFI | ExtNDC vs. G5 | 48885 (7813) vs. 11026 (4791) | p = 0.0004 |
| IgG | Con S gp140 CFI | ExtNDC vs. ExtDC | 48885 (7813) vs. 42254 (10504) | p = 0.2161 |
| IgG | Con S gp140 CFI | G3 vs. ExtDC | 22510 (6103) vs. 42254 (10504) | p = 0.0018 |
| IgG | gp70.B.CaseA V1.V2 | ExtNDC vs. G1 | 43424 (7370) vs. 2764 (1709) | p < 0.0001 |
| IgG | gp70.B.CaseA V1.V2 | ExtNDC vs. G2 | 43424 (7370) vs. 10488 (4754) | p = 0.0004 |
| IgG | gp70.B.CaseA V1.V2 | ExtNDC vs. G3 | 43424 (7370) vs. 5563 (3734) | p = 0.0008 |
| IgG | gp70.B.CaseA V1.V2 | ExtNDC vs. G4 | 43424 (7370) vs. 8720 (4527) | p = 0.0036 |
| IgG | gp70.B.CaseA V1.V2 | ExtNDC vs. G5 | 43424 (7370) vs. 1591 (2327) | p = 0.0068 |
| IgG | gp70.B.CaseA V1.V2 | ExtNDC vs. ExtDC | 43424 (7370) vs. 10166 (5334) | p = 0.0019 |
| IgG | gp70.B.CaseA V1.V2 | G3 vs. ExtDC | 5563 (3734) vs. 10166 (5334) | p = 0.149 |
| IgA | 00MSA 4076 gp140 | ExtNDC vs. G1 | 134 (135) vs. 10 (3) | p = 0.0002 |
| IgA | 00MSA 4076 gp140 | ExtNDC vs. G2 | 134 (135) vs. 9 (3) | p < 0.0001 |
| IgA | 00MSA 4076 gp140 | ExtNDC vs. G3 | 134 (135) vs. 13 (5) | p = 0.0003 |
| IgA | 00MSA 4076 gp140 | ExtNDC vs. G4 | 134 (135) vs. 21 (31) | p = 0.0036 |
| IgA | 00MSA 4076 gp140 | ExtNDC vs. G5 | 134 (135) vs. 13 (3) | p = 0.0005 |
| IgA | 00MSA 4076 gp140 | ExtNDC vs. ExtDC | 134 (135) vs. 261 (202) | p = 0.1233 |
| IgA | 00MSA 4076 gp140 | G3 vs. ExtDC | 13 (5) vs. 261 (202) | p = 0.0001 |
| IgA | A1.con.env03 140 CF | ExtNDC vs. G1 | 312 (614) vs. 9 (5) | p = 0.002 |
| IgA | A1.con.env03 140 CF | ExtNDC vs. G2 | 312 (614) vs. 8 (6) | p = 0.0017 |
| IgA | A1.con.env03 140 CF | ExtNDC vs. G3 | 312 (614) vs. 16 (5) | p = 0.0107 |
| IgA | A1.con.env03 140 CF | ExtNDC vs. G4 | 312 (614) vs. 42 (49) | p = 0.0788 |
| IgA | A1.con.env03 140 CF | ExtNDC vs. G5 | 312 (614) vs. 12 (8) | p = 0.0038 |
| IgA | A1.con.env03 140 CF | ExtNDC vs. ExtDC | 312 (614) vs. 313 (577) | p = 0.9877 |
| IgA | A1.con.env03 140 CF | G3 vs. ExtDC | 16 (5) vs. 313 (577) | p = 0.0391 |
| IgA | B.con.env03 140 CF | ExtNDC vs. G1 | 125 (94) vs. 10 (3) | p < 0.0001 |
| IgA | B.con.env03 140 CF | ExtNDC vs. G2 | 125 (94) vs. 9 (4) | p < 0.0001 |
| IgA | B.con.env03 140 CF | ExtNDC vs. G3 | 125 (94) vs. 11 (4) | p < 0.0001 |
| IgA | B.con.env03 140 CF | ExtNDC vs. G4 | 125 (94) vs. 25 (24) | p = 0.0037 |
| IgA | B.con.env03 140 CF | ExtNDC vs. G5 | 125 (94) vs. 10 (4) | p < 0.0001 |
| IgA | B.con.env03 140 CF | ExtNDC vs. ExtDC | 125 (94) vs. 454 (316) | p = 0.0065 |
| IgA | B.con.env03 140 CF | G3 vs. ExtDC | 11 (4) vs. 454 (316) | p < 0.0001 |
| IgA | C.con.env03 140 CF | ExtNDC vs. G1 | 427 (683) vs. 29 (19) | p = 0.0033 |
| IgA | C.con.env03 140 CF | ExtNDC vs. G2 | 427 (683) vs. 17 (8) | p = 0.0007 |
| IgA | C.con.env03 140 CF | ExtNDC vs. G3 | 427 (683) vs. 38 (25) | p = 0.008 |
| IgA | C.con.env03 140 CF | ExtNDC vs. G4 | 427 (683) vs. 60 (81) | p = 0.0255 |

TABLE 6-continued

BAMA peak time point IgG (AUC) and IgA (MFI) magnitude pairwise comparison of non-DC targeting ExtNDC-N2[NP]2 against DC-targeted groups (G1 to G5 and ExtDC in the current study and ExtDC-N2Lp3) as well as ExtDC against G3.

| Isotype | Analyte | Comparison | Mean (SD) | p Value |
|---|---|---|---|---|
| IgA | C.con.env03 140 CF | ExtNDC vs. G5 | 427 (683) vs. 20 (15) | p = 0.0011 |
| IgA | C.con.env03 140 CF | ExtNDC vs. ExtDC | 427 (683) vs. 450 (448) | p = 0.8141 |
| IgA | C.con.env03 140 CF | G3 vs. ExtDC | 38 (25) vs. 450 (448) | p = 0.0271 |
| IgA | Con S gp140 CFI | ExtNDC vs. G1 | 390 (779) vs. 18 (17) | p = 0.0032 |
| IgA | Con S gp140 CFI | ExtNDC vs. G2 | 390 (779) vs. 16 (8) | p = 0.0024 |
| IgA | Con S gp140 CFI | ExtNDC vs. G3 | 390 (779) vs. 24 (11) | p = 0.008 |
| IgA | Con S gp140 CFI | ExtNDC vs. G4 | 390 (779) vs. 111 (197) | p = 0.1235 |
| IgA | Con S gp140 CFI | ExtNDC vs. G5 | 390 (779) vs. 13 (13) | p = 0.0012 |
| IgA | Con S gp140 CFI | ExtNDC vs. ExtDC | 390 (779) vs. 850 (1136) | p = 0.3007 |
| IgA | Con S gp140 CFI | G3 vs. ExtDC | 24 (11) vs. 850 (1136) | p = 0.0078 |
| IgA | gp70.B.CaseA V1.V2 | ExtNDC vs. G1 | 64 (57) vs. 9 (7) | p = 0.0019 |
| IgA | gp70.B.CaseA V1.V2 | ExtNDC vs. G2 | 64 (57) vs. 13 (9) | p = 0.0136 |
| IgA | gp70.B.CaseA V1.V2 | ExtNDC vs. G3 | 64 (57) vs. 28 (43) | p = 0.0831 |
| IgA | gp70.B.CaseA V1.V2 | ExtNDC vs. G4 | 64 (57) vs. 22 (22) | p = 0.0679 |
| IgA | gp70.B.CaseA V1.V2 | ExtNDC vs. G5 | 64 (57) vs. 7 (5) | p = 0.0027 |
| IgA | gp70.B.CaseA V1.V2 | ExtNDC vs. ExtDC | 64 (57) vs. 48 (34) | p = 0.6556 |
| IgA | gp70.B.CaseA V1.V2 | G3 vs. ExtDC | 28 (43) vs. 48 (34) | p = 0.1912 |

*p values are from t-test assuming unequal variance between groups.

TABLE 7

Peak time point neutralization ID50 titers pair-wise comparison of non-DC targeting ExtNDC-N2[NP]2 against DC-targeted groups (G1 to G5 in the current study and ExtDC-N2Lp3) as well as ExtDC against G3.

| Assay: Isolate | Comparison | Mean (SD) | p Value* |
|---|---|---|---|
| A3R5: TV1.21.LucR.T2A.ecto | ExtNDC vs. G1 | 103.87 (64.25) vs. 18.17 (9.52) | p = 0.0002 |
| A3R5: TV1.21.LucR.T2A.ecto | ExtNDC vs. G2 | 103.87 (64.25) vs. 26.83 (14.11) | p = 0.0037 |
| A3R5: TV1.21.LucR.T2A.ecto | ExtNDC vs. G3 | 103.87 (64.25) vs. 12.67 (6.53) | p < 0.0001 |
| A3R5: TV1.21.LucR.T2A.ecto | ExtNDC vs. G4 | 103.87 (64.25) vs. 32.67 (29.47) | p = 0.0173 |
| A3R5: TV1.21.LucR.T2A.ecto | ExtNDC vs. G5 | 103.87 (64.25) vs. 17.5 (11.62) | p = 0.0003 |
| A3R5: TV1.21.LucR.T2A.ecto | ExtNDC vs. ExtDC | 103.87 (64.25) vs. 49.5 (12.06) | p = 0.0531 |
| A3R5: TV1.21.LucR.T2A.ecto | G3 vs. ExtDC | 12.67 (6.53) vs. 49.5 (12.06) | p < 0.0001 |
| TZM-bl: MN.3 | ExtNDC vs. G1 | 60.38 (68.86) vs. 14.33 (10.61) | p = 0.0272 |
| TZM-bl: MN.3 | ExtNDC vs. G2 | 60.38 (68.86) vs. 10 (0) | p = 0.0098 |
| TZM-bl: MN.3 | ExtNDC vs. G3 | 60.38 (68.86) vs. 10 (0) | p = 0.0098 |
| TZM-bl: MN.3 | ExtNDC vs. G4 | 60.38 (68.86) vs. 10 (0) | p = 0.0098 |
| TZM-bl: MN.3 | ExtNDC vs. G5 | 60.38 (68.86) vs. 10 (0) | p = 0.0098 |
| TZM-bl: MN.3 | ExtNDC vs. ExtDC | 60.38 (68.86) vs. 10 (0) | p = 0.0098 |
| TZM-bl: MN.3 | G3 vs. ExtDC | 10 (0) vs. 10 (0) | |
| TZM-bl: MW965.26 | ExtNDC vs. G1 | 3049.38 (2653.11) vs. 104.67 (62.34) | p < 0.0001 |
| TZM-bl: MW965.26 | ExtNDC vs. G2 | 3049.38 (2653.11) vs. 248.17 (204.56) | p = 0.0006 |
| TZM-bl: MW965.26 | ExtNDC vs. G3 | 3049.38 (2653.11) vs. 110 (86.89) | p = 0.0007 |
| TZM-bl: MW965.26 | ExtNDC vs. G4 | 3049.38 (2653.11) vs. 453.33 (564.57) | p = 0.0026 |
| TZM-bl: MW965.26 | ExtNDC vs. G5 | 3049.38 (2653.11) vs. 105.67 (167.7) | p = 0.0002 |
| TZM-bl: MW965.26 | ExtNDC vs. ExtDC | 3049.38 (2653.11) vs. 915.17 (898.84) | p = 0.0281 |
| TZM-bl: MW965.26 | G3 vs. ExtDC | 110 (86.89) vs. 915.17 (898.84) | p = 0.0105 |
| TZM-bl: SF162.LS | ExtNDC vs. G1 | 92.37 (93.54) vs. 10 (0) | p = 0.0076 |
| TZM-bl: SF162.LS | ExtNDC vs. G2 | 92.37 (93.54) vs. 10 (0) | p = 0.0076 |
| TZM-bl: SF162.LS | ExtNDC vs. G3 | 92.37 (93.54) vs. 10 (0) | p = 0.0076 |
| TZM-bl: SF162.LS | ExtNDC vs. G4 | 92.37 (93.54) vs. 10 (0) | p = 0.0076 |
| TZM-bl: SF162.LS | ExtNDC vs. G5 | 92.37 (93.54) vs. 10 (0) | p = 0.0076 |
| TZM-bl: SF162.LS | ExtNDC vs. ExtDC | 92.37 (93.54) vs. 10 (0) | p = 0.0076 |
| TZM-bl: SF162.LS | G3 vs. ExtDC | 10 (0) vs. 10 (0) | |
| TZM-bl: TH023.6 | ExtNDC vs. G1 | 406.5 (657.58) vs. 42.5 (41.11) | p = 0.0136 |
| TZM-bl: TH023.6 | ExtNDC vs. G2 | 406.5 (657.58) vs. 108.33 (160.32) | p = 0.073 |
| TZM-bl: TH023.6 | ExtNDC vs. G3 | 406.5 (657.58) vs. 98.33 (207.2) | p = 0.0301 |
| TZM-bl: TH023.6 | ExtNDC vs. G4 | 406.5 (657.58) vs. 71.83 (75.34) | p = 0.0588 |
| TZM-bl: TH023.6 | ExtNDC vs. G5 | 406.5 (657.58) vs. 10 (0) | p = 0.0005 |
| TZM-bl: TH023.6 | ExtNDC vs. ExtDC | 406.5 (657.58) vs. 173.83 (228.74) | p = 0.3105 |
| TZM-bl: TH023.6 | G3 vs. ExtDC | 98.33 (207.2) vs. 173.83 (228.74) | p = 0.1586 |

*p values are from t-test assuming unequal variance between groups.

TABLE 8

Peak time point ADCC ID50 titers pair-wise comparison of non-DC targeting ExtNDC-N2[NP]2 against DC-targeted groups (G1 to G5 in the current study and ExtDC N2Lp3) as well as ExtDC against G3.

| Parameter | Comparison | Mean (SD) | p Value* |
|---|---|---|---|
| GTL ADCC: peak | ExtNDC vs. G1 | 11.023 (5.75) vs. 5.22 (6.202) | p = 0.103 |
| GTL ADCC: peak | ExtNDC vs. G2 | 11.023 (5.75) vs. 6.364 (5.121) | p = 0.1371 |
| GTL ADCC: peak | ExtNDC vs. G3 | 11.023 (5.75) vs. 3.81 (3.099) | p = 0.0117 |
| GTL ADCC: peak | ExtNDC vs. G4 | 11.023 (5.75) vs. 8.568 (5.331) | p = 0.4266 |
| GTL ADCC: peak | ExtNDC vs. G5 | 11.023 (5.75) vs. 3.469 (3.527) | p = 0.0107 |
| GTL ADCC: peak | ExtNDC vs. ExtDC | 11.023 (5.75) vs. 1.002 (0.207) | p = 0.0017 |
| GTL ADCC: peak | G3 vs. ExtDC | 3.81 (3.099) vs. 1.002 (0.207) | p = 0.0772 |
| GTL ADCC: auc | ExtNDC vs. G1 | 20.24 (9.508) vs. 3.063 (3.796) | p = 0.001 |
| GTL ADCC: auc | ExtNDC vs. G2 | 20.24 (9.508) vs. 5.908 (6.776) | p = 0.0064 |
| GTL ADCC: auc | ExtNDC vs. G3 | 20.24 (9.508) vs. 2.292 (1.972) | p = 0.0009 |
| GTL ADCC: auc | ExtNDC vs. G4 | 20.24 (9.508) vs. 6.805 (5.879) | p = 0.0071 |
| GTL ADCC: auc | ExtNDC vs. G5 | 20.24 (9.508) vs. 1.678 (1.612) | p = 0.0008 |
| GTL ADCC: auc | ExtNDC vs. ExtDC | 20.24 (9.508) vs. 1.082 (0.405) | p = 0.0007 |
| GTL ADCC: auc | G3 vs. ExtDC | 2.292 (1.972) vs. 1.082 (0.405) | p = 0.1974 |

*p values are from t-test assuming unequal variance between groups

TABLE 9

Peak time point CD4+ and CD8+ T 62 cells HIV-specific cytokine secreting response pair-wise comparison of non-DC targeting ExtNDC-N2[NP]2 against DC-targeted groups (G1 to G5 in the current study and ExtDC N2Lp3) as well as ExtDC against G3.

| Parameter | Comparison | Mean (SD) | p Value* |
|---|---|---|---|
| CD4+ Any Env AnyCyto | ExtNDC vs. G1 | 0.87 (0.514) vs. 0.387 (0.361) | p = 0.0451 |
| CD4+ Any Env AnyCyto | ExtNDC vs. G2 | 0.87 (0.514) vs. 0.642 (0.343) | p = 0.4529 |
| CD4+ Any Env AnyCyto | ExtNDC vs. G3 | 0.87 (0.514) vs. 0.305 (0.228) | p = 0.0184 |
| CD4+ Any Env AnyCyto | ExtNDC vs. G4 | 0.87 (0.514) vs. 0.447 (0.287) | p = 0.0847 |
| CD4+ Any Env AnyCyto | ExtNDC vs. G5 | 0.87 (0.514) vs. 0.082 (0.023) | p < 0.0001 |
| CD4+ Any Env AnyCyto | ExtNDC vs. ExtDC | 0.87 (0.514) vs. 0.278 (0.146) | p = 0.0083 |
| CD4+ Any Env AnyCyto | G3 vs ExtDC | 0.305 (0.228) vs. 0.278 (0.146) | p = 0.9744 |
| CD4+ Any HIV Antigen AnyCyto | ExtNDC vs. G1 | 0.919 (0.501) vs. 0.441 (0.355) | p = 0.0555 |
| CD4+ Any HIV Antigen AnyCyto | ExtNDC vs. G2 | 0.919 (0.501) vs. 0.693 (0.359) | p = 0.4711 |
| CD4+ Any HIV Antigen AnyCyto | ExtNDC vs. G3 | 0.919 (0.501) vs. 0.338 (0.23) | p = 0.0199 |
| CD4+ Any HIV Antigen AnyCyto | ExtNDC vs. G4 | 0.919 (0.501) vs. 0.471 (0.289) | p = 0.0784 |
| CD4+ Any HIV Antigen AnyCyto | ExtNDC vs. G5 | 0.919 (0.501) vs. 0.115 (0.036) | p < 0.0001 |
| CD4+ Any HIV Antigen AnyCyto | ExtNDC vs. ExtDC | 0.919 (0.501) vs. 0.428 (0.246) | p = 0.0465 |
| CD4+ Any HIV Antigen AnyCyto | G3 vs ExtDC | 0.338 (0.23) vs. 0.428 (0.246) | p = 0.4299 |
| CD8+ Any Env AnyCyto | ExtNDC vs. G1 | 0.184 (0.226) vs. 0.091 (0.063) | p = 0.3725 |
| CD8+ Any Env AnyCyto | ExtNDC vs. G2 | 0.184 (0.226) vs. 0.197 (0.169) | p = 0.6862 |
| CD8+ Any Env AnyCyto | ExtNDC vs. G3 | 0.184 (0.226) vs. 0.054 (0.01) | p = 0.0634 |
| CD8+ Any Env AnyCyto | ExtNDC vs. G4 | 0.184 (0.226) vs. 0.074 (0.033) | p = 0.2111 |
| CD8+ Any Env AnyCyto | ExtNDC vs. G5 | 0.184 (0.226) vs. 0.052 (0.006) | p = 0.0554 |
| CD8+ Any Env AnyCyto | ExtNDC vs. ExtDC | 0.184 (0.226) vs. 0.108 (0.056) | p = 0.6869 |
| CD8+ Any Env AnyCyto | G3 vs ExtDC | 0.054 (0.01) vs. 0.108 (0.056) | p = 0.0436 |
| CD8+ Any HIV Antigen AnyCyto | ExtNDC vs. G1 | 0.333 (0.243) vs. 0.148 (0.111) | p = 0.0462 |
| CD8+ Any HIV Antigen AnyCyto | ExtNDC vs. G2 | 0.333 (0.243) vs. 0.212 (0.147) | p = 0.2487 |
| CD8+ Any HIV Antigen AnyCyto | ExtNDC vs. G3 | 0.333 (0.243) vs. 0.071 (0.032) | p = 0.0003 |
| CD8+ Any HIV Antigen AnyCyto | ExtNDC vs. G4 | 0.333 (0.243) vs. 0.139 (0.122) | p = 0.0399 |
| CD8+ Any HIV Antigen AnyCyto | ExtNDC vs. G5 | 0.333 (0.243) vs. 0.069 (0.045) | p = 0.0003 |
| CD8+ Any HIV Antigen AnyCyto | ExtNDC vs. ExtDC | 0.333 (0.243) vs. 0.313 (0.227) | p = 0.7621 |
| CD8+ Any HIV Antigen AnyCyto | G3 vs ExtDC | 0.071 (0.032) vs. 0.313 (0.227) | p = 0.015 |

*p values are from t-test assuming unequal variance between groups

TABLE 10

Pair-wise comparison of durability (proportion of change per week) of binding antibody response among G1-G5 of the current study and ExtNDC-N2[NP]2.

| Analyte | Comparison | Mean (SD) | p Value* |
|---|---|---|---|
| 00MSA 4076 gp140 | ExtNDC vs. G1 | −0.075 (0.019) vs. −0.118 (0.032) | p = 0.0343 |
| 00MSA 4076 gp140 | ExtNDC vs. G2 | −0.075 (0.019) vs. −0.091 (0.037) | p = 0.3704 |
| 00MSA 4076 gp140 | ExtNDC vs. G3 | −0.075 (0.019) vs. −0.099 (0.016) | p = 0.0268 |
| 00MSA 4076 gp140 | ExtNDC vs. G4 | −0.075 (0.019) vs. −0.077 (0.035) | p = 0.9317 |

TABLE 10-continued

Pair-wise comparison of durability (proportion of change per week) of binding antibody response among G1-G5 of the current study and ExtNDC-N2[NP]2.

| Analyte | Comparison | Mean (SD) | p Value* |
|---|---|---|---|
| 00MSA 4076 gp140 | ExtNDC vs. G5 | −0.075 (0.019) vs. −0.108 (0.021) | p = 0.0119 |
| 00MSA 4076 gp140 | ExtNDC vs. ExtDC | −0.075 (0.019) vs. −0.063 (0.009) | p = 0.129 |
| 00MSA 4076 gp140 | G1 vs. G2 | −0.118 (0.032) vs. −0.091 (0.037) | p = 0.2238 |
| 00MSA 4076 gp140 | G1 vs. G3 | −0.118 (0.032) vs. −0.099 (0.016) | p = 0.2571 |
| 00MSA 4076 gp140 | G1 vs. G4 | −0.118 (0.032) vs. −0.077 (0.035) | p = 0.0691 |
| 00MSA 4076 gp140 | G1 vs. G5 | −0.118 (0.032) vs. −0.108 (0.021) | p = 0.5668 |
| 00MSA 4076 gp140 | G1 vs. ExtDC | −0.118 (0.032) vs. −0.063 (0.009) | p = 0.0151 |
| 00MSA 4076 gp140 | G2 vs. G3 | −0.091 (0.037) vs. −0.099 (0.016) | p = 0.6634 |
| 00MSA 4076 gp140 | G2 vs. G4 | −0.091 (0.037) vs. −0.077 (0.035) | p = 0.5044 |
| 00MSA 4076 gp140 | G2 vs. G5 | −0.091 (0.037) vs. −0.108 (0.021) | p = 0.3546 |
| 00MSA 4076 gp140 | G2 vs. ExtDC | −0.091 (0.037) vs. −0.063 (0.009) | p = 0.1241 |
| 00MSA 4076 gp140 | G3 vs. G4 | −0.099 (0.016) vs. −0.077 (0.035) | p = 0.2052 |
| 00MSA 4076 gp140 | G3 vs. G5 | −0.099 (0.016) vs. −0.108 (0.021) | p = 0.3927 |
| 00MSA 4076 gp140 | G3 vs. ExtDC | −0.099 (0.016) vs. −0.063 (0.009) | p = 0.0014 |
| 00MSA 4076 gp140 | G4 vs. G5 | −0.077 (0.035) vs. −0.108 (0.021) | p = 0.0941 |
| 00MSA 4076 gp140 | G4 vs. ExtDC | −0.077 (0.035) vs. −0.063 (0.009) | p = 0.3884 |
| 00MSA 4076 gp140 | G5 vs. ExtDC | −0.108 (0.021) vs. −0.063 (0.009) | p = 0.002 |
| A1.con.env03 140 CF | ExtNDC vs. G1 | −0.064 (0.016) vs. −0.117 (0.016) | p < 0.0001 |
| A1.con.env03 140 CF | ExtNDC vs. G2 | −0.064 (0.016) vs. −0.09 (0.031) | p = 0.1011 |
| A1.con.env03 140 CF | ExtNDC vs. G3 | −0.064 (0.016) vs. −0.095 (0.019) | p = 0.0088 |
| A1.con.env03 140 CF | ExtNDC vs. G4 | −0.064 (0.016) vs. −0.071 (0.029) | p = 0.6128 |
| A1.con.env03 140 CF | ExtNDC vs. G5 | −0.064 (0.016) vs. −0.116 (0.02) | p = 0.0004 |
| A1.con.env03 140 CF | ExtNDC vs. ExtDC | −0.064 (0.016) vs. −0.059 (0.008) | p = 0.4713 |
| A1.con.env03 140 CF | G1 vs. G2 | −0.117 (0.016) vs. −0.09 (0.031) | p = 0.1003 |
| A1.con.env03 140 CF | G1 vs. G3 | −0.117 (0.016) vs. −0.095 (0.019) | p = 0.0537 |
| A1.con.env03 140 CF | G1 vs. G4 | −0.117 (0.016) vs. −0.071 (0.029) | p = 0.0095 |
| A1.con.env03 140 CF | G1 vs. G5 | −0.117 (0.016) vs. −0.116 (0.02) | p = 0.9043 |
| A1.con.env03 140 CF | G1 vs. ExtDC | −0.117 (0.016) vs. −0.059 (0.008) | p < 0.0001 |
| A1.con.env03 140 CF | G2 vs. G3 | −0.09 (0.031) vs. −0.095 (0.019) | p = 0.7586 |
| A1.con.env03 140 CF | G2 vs. G4 | −0.09 (0.031) vs. −0.071 (0.029) | p = 0.292 |
| A1.con.env03 140 CF | G2 vs. G5 | −0.09 (0.031) vs. −0.116 (0.02) | p = 0.1262 |
| A1.con.env03 140 CF | G2 vs. ExtDC | −0.09 (0.031) vs. −0.059 (0.008) | p = 0.0585 |
| A1.con.env03 140 CF | G3 vs. G4 | −0.095 (0.019) vs. −0.071 (0.029) | p = 0.1241 |
| A1.con.env03 140 CF | G3 vs. G5 | −0.095 (0.019) vs. −0.116 (0.02) | p = 0.0906 |
| A1.con.env03 140 CF | G3 vs. ExtDC | −0.095 (0.019) vs. −0.059 (0.008) | p = 0.0039 |
| A1.con.env03 140 CF | G4 vs. G5 | −0.071 (0.029) vs. −0.116 (0.02) | p = 0.0123 |
| A1.con.env03 140 CF | G4 vs. ExtDC | −0.071 (0.029) vs. −0.059 (0.008) | p = 0.3783 |
| A1.con.env03 140 CF | G5 vs. ExtDC | −0.116 (0.02) vs. −0.059 (0.008) | p = 0.0004 |
| B.con.env03 140 CF | ExtNDC vs. G1 | −0.084 (0.012) vs. −0.129 (0.021) | p = 0.0017 |
| B.con.env03 140 CF | ExtNDC vs. G2 | −0.084 (0.012) vs. −0.103 (0.04) | p = 0.3158 |
| B.con.env03 140 CF | ExtNDC vs. G3 | −0.084 (0.012) vs. −0.12 (0.013) | p = 0.0004 |
| B.con.env03 140 CF | ExtNDC vs. G4 | −0.084 (0.012) vs. −0.1 (0.017) | p = 0.0895 |
| B.con.env03 140 CF | ExtNDC vs. G5 | −0.084 (0.012) vs. −0.132 (0.015) | p = 0.0001 |
| B.con.env03 140 CF | ExtNDC vs. ExtDC | −0.084 (0.012) vs. −0.068 (0.011) | p = 0.023 |
| B.con.env03 140 CF | G1 vs. G2 | −0.129 (0.021) vs. −0.103 (0.04) | p = 0.2008 |
| B.con.env03 140 CF | G1 vs. G3 | −0.129 (0.021) vs. −0.12 (0.013) | p = 0.3956 |
| B.con.env03 140 CF | G1 vs. G4 | −0.129 (0.021) vs. −0.1 (0.017) | p = 0.0268 |
| B.con.env03 140 CF | G1 vs. G5 | −0.129 (0.021) vs. −0.132 (0.015) | p = 0.7818 |
| B.con.env03 140 CF | G1 vs. ExtDC | −0.129 (0.021) vs. −0.068 (0.011) | p = 0.0003 |
| B.con.env03 140 CF | G2 vs. G3 | −0.103 (0.04) vs. −0.12 (0.013) | p = 0.3641 |
| B.con.env03 140 CF | G2 vs. G4 | −0.103 (0.04) vs. −0.1 (0.017) | p = 0.8826 |
| B.con.env03 140 CF | G2 vs. G5 | −0.103 (0.04) vs. −0.132 (0.015) | p = 0.1481 |
| B.con.env03 140 CF | G2 vs. ExtDC | −0.103 (0.04) vs. −0.068 (0.011) | p = 0.0878 |
| B.con.env03 140 CF | G3 vs. G4 | −0.12 (0.013) vs. −0.1 (0.017) | p = 0.0538 |
| B.con.env03 140 CF | G3 vs. G5 | −0.12 (0.013) vs. −0.132 (0.015) | p = 0.1764 |
| B.con.env03 140 CF | G3 vs. ExtDC | −0.12 (0.013) vs. −0.068 (0.011) | p < 0.0001 |
| B.con.env03 140 CF | G4 vs. G5 | −0.1 (0.017) vs. −0.132 (0.015) | p = 0.0073 |
| B.con.env03 140 CF | G4 vs. ExtDC | −0.1 (0.017) vs. −0.068 (0.011) | p = 0.0045 |
| B.con.env03 140 CF | G5 vs. ExtDC | −0.132 (0.015) vs. −0.068 (0.011) | p < 0.0001 |
| C.con.env03 140 CF | ExtNDC vs. G1 | −0.058 (0.016) vs. −0.091 (0.028) | p = 0.035 |
| C.con.env03 140 CF | ExtNDC vs. G2 | −0.058 (0.016) vs. −0.045 (0.067) | p = 0.6572 |
| C.con.env03 140 CF | ExtNDC vs. G3 | −0.058 (0.016) vs. −0.069 (0.029) | p = 0.4269 |
| C.con.env03 140 CF | ExtNDC vs. G4 | −0.058 (0.016) vs. −0.041 (0.014) | p = 0.0646 |
| C.con.env03 140 CF | ExtNDC vs. G5 | −0.058 (0.016) vs. −0.092 (0.035) | p = 0.0625 |
| C.con.env03 140 CF | ExtNDC vs. ExtDC | −0.058 (0.016) vs. −0.062 (0.007) | p = 0.5735 |
| C.con.env03 140 CF | G1 vs. G2 | −0.091 (0.028) vs. −0.045 (0.067) | p = 0.1682 |
| C.con.env03 140 CF | G1 vs. G3 | −0.091 (0.028) vs. −0.069 (0.029) | p = 0.2139 |
| C.con.env03 140 CF | G1 vs. G4 | −0.091 (0.028) vs. −0.041 (0.014) | p = 0.0056 |
| C.con.env03 140 CF | G1 vs. G5 | −0.091 (0.028) vs. −0.092 (0.035) | p = 0.9297 |
| C.con.env03 140 CF | G1 vs. ExtDC | −0.091 (0.028) vs. −0.062 (0.007) | p = 0.0511 |
| C.con.env03 140 CF | G2 vs. G3 | −0.045 (0.067) vs. −0.069 (0.029) | p = 0.4468 |
| C.con.env03 140 CF | G2 vs. G4 | −0.045 (0.067) vs. −0.041 (0.014) | p = 0.9069 |
| C.con.env03 140 CF | G2 vs. G5 | −0.045 (0.067) vs. −0.092 (0.035) | p = 0.1649 |
| C.con.env03 140 CF | G2 vs. ExtDC | −0.045 (0.067) vs. −0.062 (0.007) | p = 0.5685 |
| C.con.env03 140 CF | G3 vs. G4 | −0.069 (0.029) vs. −0.041 (0.014) | p = 0.0734 |

TABLE 10-continued

Pair-wise comparison of durability (proportion of change per week) of binding antibody response among G1-G5 of the current study and ExtNDC-N2[NP]2.

| Analyte | Comparison | Mean (SD) | p Value* |
|---|---|---|---|
| C.con.env03 140 CF | G3 vs. G5 | −0.069 (0.029) vs. −0.092 (0.035) | p = 0.2355 |
| C.con.env03 140 CF | G3 vs. ExtDC | −0.069 (0.029) vs. −0.062 (0.007) | p = 0.5723 |
| C.con.env03 140 CF | G4 vs. G5 | −0.041 (0.014) vs. −0.092 (0.035) | p = 0.0142 |
| C.con.env03 140 CF | G4 vs. ExtDC | −0.041 (0.014) vs. −0.062 (0.007) | p = 0.0172 |
| C.con.env03 140 CF | G5 vs. ExtDC | −0.092 (0.035) vs. −0.062 (0.007) | p = 0.0848 |
| Con S gp140 CFI | ExtNDC vs. G1 | −0.055 (0.017) vs. −0.097 (0.025) | p = 0.0068 |
| Con S gp140 CFI | ExtNDC vs. G2 | −0.055 (0.017) vs. −0.057 (0.061) | p = 0.9456 |
| Con S gp140 CFI | ExtNDC vs. G3 | −0.055 (0.017) vs. −0.075 (0.024) | p = 0.1181 |
| Con S gp140 CFI | ExtNDC vs. G4 | −0.055 (0.017) vs. −0.052 (0.031) | p = 0.8115 |
| Con S gp140 CFI | ExtNDC vs. G5 | −0.055 (0.017) vs. −0.108 (0.028) | p = 0.0034 |
| Con S gp140 CFI | ExtNDC vs. ExtDC | −0.055 (0.017) vs. −0.052 (0.01) | p = 0.7156 |
| Con S gp140 CFI | G1 vs. G2 | −0.097 (0.025) vs. −0.057 (0.061) | p = 0.1803 |
| Con S gp140 CFI | G1 vs. G3 | −0.097 (0.025) vs. −0.075 (0.024) | p = 0.1527 |
| Con S gp140 CFI | G1 vs. G4 | −0.097 (0.025) vs. −0.052 (0.031) | p = 0.0182 |
| Con S gp140 CFI | G1 vs. G5 | −0.097 (0.025) vs. −0.108 (0.028) | p = 0.4876 |
| Con S gp140 CFI | G1 vs. ExtDC | −0.097 (0.025) vs. −0.052 (0.01) | p = 0.0053 |
| Con S gp140 CFI | G2 vs. G3 | −0.057 (0.061) vs. −0.075 (0.024) | p = 0.5186 |
| Con S gp140 CFI | G2 vs. G4 | −0.057 (0.061) vs. −0.052 (0.031) | p = 0.8562 |
| Con S gp140 CFI | G2 vs. G5 | −0.057 (0.061) vs. −0.108 (0.028) | p = 0.1033 |
| Con S gp140 CFI | G2 vs. ExtDC | −0.057 (0.061) vs. −0.052 (0.01) | p = 0.8649 |
| Con S gp140 CFI | G3 vs. G4 | −0.075 (0.024) vs. −0.052 (0.031) | p = 0.1712 |
| Con S gp140 CFI | G3 vs. G5 | −0.075 (0.024) vs. −0.108 (0.028) | p = 0.0536 |
| Con S gp140 CFI | G3 vs. ExtDC | −0.075 (0.024) vs. −0.052 (0.01) | p = 0.0737 |
| Con S gp140 CFI | G4 vs. G5 | −0.052 (0.031) vs. −0.108 (0.028) | p = 0.0072 |
| Con S gp140 CFI | G4 vs. ExtDC | −0.052 (0.031) vs. −0.052 (0.01) | p = 0.9582 |
| Con S gp140 CFI | G5 vs. ExtDC | −0.108 (0.028) vs. −0.052 (0.01) | p = 0.0031 |
| gp70.B.CaseA V1.V2 | ExtNDC vs. G1 | −0.076 (0.012) vs. −0.139 (0.036) | p = 0.0069 |
| gp70.B.CaseA V1.V2 | ExtNDC vs. G2 | −0.076 (0.012) vs. −0.107 (0.034) | p = 0.0725 |
| gp70.B.CaseA V1.V2 | ExtNDC vs. G3 | −0.076 (0.012) vs. −0.125 (0.029) | p = 0.007 |
| gp70.B.CaseA V1.V2 | ExtNDC vs. G4 | −0.076 (0.012) vs. −0.064 (0.081) | p = 0.7421 |
| gp70.B.CaseA V1.V2 | ExtNDC vs. G5 | −0.076 (0.012) vs. −0.142 (0.041) | p = 0.1063 |
| gp70.B.CaseA V1.V2 | ExtNDC vs. ExtDC | −0.076 (0.012) vs. −0.085 (0.011) | p = 0.1501 |
| gp70.B.CaseA V1.V2 | G1 vs. G2 | −0.139 (0.036) vs. −0.107 (0.034) | p = 0.1533 |
| gp70.B.CaseA V1.V2 | G1 vs. G3 | −0.139 (0.036) vs. −0.125 (0.029) | p = 0.4923 |
| gp70.B.CaseA V1.V2 | G1 vs. G4 | −0.139 (0.036) vs. −0.064 (0.081) | p = 0.081 |
| gp70.B.CaseA V1.V2 | G1 vs. G5 | −0.139 (0.036) vs. −0.142 (0.041) | p = 0.9146 |
| gp70.B.CaseA V1.V2 | G1 vs. ExtDC | −0.139 (0.036) vs. −0.085 (0.011) | p = 0.014 |
| gp70.B.CaseA V1.V2 | G2 vs. G3 | −0.107 (0.034) vs. −0.125 (0.029) | p = 0.3521 |
| gp70.B.CaseA V1.V2 | G2 vs. G4 | −0.107 (0.034) vs. −0.064 (0.081) | p = 0.2721 |
| gp70.B.CaseA V1.V2 | G2 vs. G5 | −0.107 (0.034) vs. −0.142 (0.041) | p = 0.2918 |
| gp70.B.CaseA V1.V2 | G2 vs. ExtDC | −0.107 (0.034) vs. −0.085 (0.011) | p = 0.1795 |
| gp70.B.CaseA V1.V2 | G3 vs. G4 | −0.125 (0.029) vs. −0.064 (0.081) | p = 0.1336 |
| gp70.B.CaseA V1.V2 | G3 vs. G5 | −0.125 (0.029) vs. −0.142 (0.041) | p = 0.5754 |
| gp70.B.CaseA V1.V2 | G3 vs. ExtDC | −0.125 (0.029) vs. −0.085 (0.011) | p = 0.0183 |
| gp70.B.CaseA V1.V2 | G4 vs. G5 | −0.064 (0.081) vs. −0.142 (0.041) | p = 0.101 |
| gp70.B.CaseA V1.V2 | G4 vs. ExtDC | −0.064 (0.081) vs. −0.085 (0.011) | p = 0.5557 |
| gp70.B.CaseA V1.V2 | G5 vs. ExtDC | −0.142 (0.041) vs. −0.085 (0.011) | p = 0.1386 |

*p values are from t-test assuming unequal variance between groups

TABLE 11

Pair-wise comparison of durability (proportion of change per week) of neutralizing activity among G1-G5 of the current study and ExtNDC-N2[NP]2.

| Parameter | Comparison | Mean (SD) | p Value* |
|---|---|---|---|
| TZM-bl: MW965.26 | ExtNDC vs. G1 | −0.09 (0.006) vs. −0.14 (0.007) | p < 0.0001 |
| TZM-bl: MW965.26 | ExtNDC vs. G2 | −0.09 (0.006) vs. −0.116 (0.054) | p = 0.3022 |
| TZM-bl: MW965.26 | ExtNDC vs. G3 | −0.09 (0.006) vs. −0.136 (0.031) | p = 0.0586 |
| TZM-bl: MW965.26 | ExtNDC vs. G4 | −0.09 (0.006) vs. −0.124 (0.026) | p = 0.0239 |
| TZM-bl: MW965.26 | ExtNDC vs. G5 | −0.09 (0.006) vs. −0.122 (0.018) | p = 0.017 |
| TZM-bl: MW965.26 | ExtNDC vs. ExtDC | −0.09 (0.006) vs. −0.078 (0.011) | p = 0.0473 |
| TZM-bl: MW965.26 | G1 vs. G2 | −0.14 (0.007) vs. −0.116 (0.054) | p = 0.3268 |
| TZM-bl: MW965.26 | G1 vs. G3 | −0.14 (0.007) vs. −0.136 (0.031) | p = 0.7903 |
| TZM-bl: MW965.26 | G1 vs. G4 | −0.14 (0.007) vs. −0.124 (0.026) | p = 0.1843 |
| TZM-bl: MW965.26 | G1 vs. G5 | −0.14 (0.007) vs. −0.122 (0.018) | p = 0.0875 |
| TZM-bl: MW965.26 | G1 vs. ExtDC | −0.14 (0.007) vs. −0.078 (0.011) | p < 0.0001 |
| TZM-bl: MW965.26 | G2 vs. G3 | −0.116 (0.054) vs. −0.136 (0.031) | p = 0.486 |
| TZM-bl: MW965.26 | G2 vs. G4 | −0.116 (0.054) vs. −0.124 (0.026) | p = 0.7603 |
| TZM-bl: MW965.26 | G2 vs. G5 | −0.116 (0.054) vs. −0.122 (0.018) | p = 0.8167 |
| TZM-bl: MW965.26 | G2 vs. ExtDC | −0.116 (0.054) vs. −0.078 (0.011) | p = 0.1522 |

TABLE 11-continued

Pair-wise comparison of durability (proportion of change per week) of neutralizing activity among G1-G5 of the current study and ExtNDC-N2[NP]2.

| Parameter | Comparison | Mean (SD) | p Value* |
|---|---|---|---|
| TZM-bl: MW965.26 | G3 vs. G4 | −0.136 (0.031) vs. −0.124 (0.026) | p = 0.5462 |
| TZM-bl: MW965.26 | G3 vs. G5 | −0.136 (0.031) vs. −0.122 (0.018) | p = 0.4605 |
| TZM-bl: MW965.26 | G3 vs. ExtDC | −0.136 (0.031) vs. −0.078 (0.011) | p = 0.0282 |
| TZM-bl: MW965.26 | G4 vs. G5 | −0.124 (0.026) vs. −0.122 (0.018) | p = 0.8805 |
| TZM-bl: MW965.26 | G4 vs. ExtDC | −0.124 (0.026) vs. −0.078 (0.011) | p = 0.0057 |
| TZM-bl: MW965.26 | G5 vs. ExtDC | −0.122 (0.018) vs. −0.078 (0.011) | p = 0.0031 |

*p values are from t-test assuming unequal variance between groups.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509
U.S. Pat. No. 4,938,948
U.S. Pat. No. 5,196,066
U.S. Pat. No. 5,741,957
U.S. Pat. No. 5,750,172
U.S. Pat. No. 5,756,687
U.S. Pat. No. 5,827,690
U.S. Pat. No. 6,091,001
U.S. Patent Publication No. 2005/0106660
U.S. Patent Publication No. 2006/0058510
U.S. Patent Publication No. 2006/0088908
U.S. Patent Publication No. 2010/0285564
U.S. Patent Application No. 61/332,465
PCT/US1992/009965
WO 1994/13804
WO 2006/056464
WO 2008/103947
WO 2008/103953
WO 2008/118587
WO 2010/104747
WO 2010/104761
WO 2012/021834
Atherton, et al., *Biol Reprod.* 32(1):155-71, 1985.
Ausubel, et al., *PNAS USA.* 93(26):15317-22, 1996.
Banchereau, et al., *Annu Rev Immunol.* 18:767-811, 2000.
Banchereau, et al., *Cell.* 106(3):271-4, 2001.
Barany & Merrifield, *Anal Biochem.* 95(1):160-70, 1979.
Bird, et al., *Science.* 242(4877):423-6, 1988.
Burke, et al., *J Virol.* 68(5):2803-10, 1994.
Cella, et al., *Curr Opin Immunol.* 9(1):10-6, 1997.
Cumber, et al., *J Immunol.* 149(1):12-6, 1992.
Dholakia, et al., *J Biol Chem.* 264(34):20638-42, 1989.
Glennie, et al., *J Immunol.* 139:2367-2375, 1987.
Goding, "Monoclonal antibodies," Academic Press: London, pp. 60-61, 1986.
Holliger, et al, *PNAS USA.* 90:6444-6448, 1993.
Holliger & Winter, *Cancer Metastasis Rev.* 18:411–419, 1999.
Holt, et al., *Trends Biotechnol.* 21(11):484-90, 2003.
Hu, et al., *Cancer Res.* 56(13):3055-61, 1996.
Huston, et al., *Int Rev Immunol.* 10(2-3): 195-217, 1988.
Khatoon, et al., *Prog Clin Biol Res.* 317:801-7, 1989.
King, et al., *Biochemistry.* 28(22):8833-9, 1989.
Kohl, et al., *PNAS USA.* 100(4):1700-5, 2003.
Liu, et al., *Cell Mol Biol.* 49(2):209-16, 2003.
McCafferty, et al., *Nature.* 348(6301):552-4, 1990.
Mellman & Steinman, *Cell.* 106(3):255-8, 2001.
Merchand, et al., *Nature Biotech.* 16:677-681, 1998.
Merrifield, *Science.* 232(4748):341-7, 1986.
O'Shannessy, et al., *Biotechnol Appl Biochem.* 9(6):488-96, 1987.
Owens & Haley, *Biochem Biophys Res Commun.* 142(3): 964-71, 1987.
Pack, et al., *Biochemistry.* 31:1579-84, 1992.
Panicali, et al., *Proc. Natl. Acad. Sci. USA.* 80: 53645368, 1983.
Potter & Haley, *Methods Enzymol.* 91:614-33, 1983.
Reiter, et al., *Nat Biotechnol.* 14(1):1239–45, 1996.
Repp, et al., *J Hemat.* 377-382, 1995.
Ridgeway et al., *Protein Eng.* 9:616-621, 1996.
Skerra, *J Mol Recognit.* 13(4):167-87, 2000.
Skerra, *J Biotechnol.* 74(4):257-75, 2001.
Staerz & Bevan, *PNAS.* 83(5):1453-7, 1986.
Suresh, et al., *Method Enzymol.* 121:210-228, 1986.
Steinman & Dhodapkar, *J Exp Med.* 193(2):233-8, 2001.
Steinman, et al., *Ann Rev Immunol.* 9:271, 1991.
Stewart & Young, "Solid Phase Peptide Synthesis," Freeman: SF, 1984.
Tam, et al., *Aust J Exp Biol Med Sci.* 61(Pt 6):629-36, 1983.
Tigges, et al., *J Immunol.* 156(10):3901-10, 1996.
Ward, et al., *J Biol Chem.* 264:8164-70, 1989.
Steinman R M., et al., *Annu Rev Immunol.* 30:1-22, 2012.
Zurawski G, et al., *PLoS One.* 11:e0153484, 2016.
Joo H, et al., 2014. C-type lectin-like receptor LOX-1 promotes dendritic cell-mediated class-switched B cell responses. Immunity 41:592-604.

Kastenmuller W, et al., *Nat Rev Immunol.* 14:705-711, 2014.
Cohn L, et al., *Front Immunol.* 5, 2014.
Apostolopoulos V, et al., *Clin Transl Immunology.* 3:e21, 2014.
Schjetne K W, et al., *J Immunol.* 178:4169-4176, 2007.
Chatterjee B, et al., *Blood.* 120:2011-2020, 2012.
Flamar A L, et al., *AIDS.* 27:2041-2051, 2013.
Chen J, et al., *J Hematol Oncol.* 8:35, 2015.
Rosalia R A, et al., *Biomaterials.* 40:88-97, 2015.
Yin W, et al., *EBioMed.* 5:46-58, 2016.
Elgueta R, et al., *Immunol Rev.* 229:152-172, 2009.
Flamar A L, et al., *J Immunol.* 189:2645-2655, 2012.
Li D, et al., *J Exp Med.* 209:109-121, 2012.
Skinner J A, et al., *Clin Vaccine Immunol.* 21:1668-1680, 2014.
Kibler K V, et al., *PLoS One.* 6:e25674, 2011.
Montefiori D C. *Methods Mol Biol.* 485:395-405, 2009.
Sarzotti-Kelsoe M, et al., *J Immunol Methods.* 409:147-160, 2014.
Todd C A, et al., *J Immunol Methods.* 375:57-67, 2012.
Huang Y, et al., *Stat Biopharm Res.* 1:81-91, 2009.
Liao H X, et al., *Immunity:*38: 176-186, 2013.
Tomaras G D, et al., *J Virol.* 82:12449-12463, 2008.
Gaschen B1, et al., *Science.* 296:2354-2360, 2002.
Liao H X, et al., *Virology.* 353:268-282, 2006.
Haynes B F, et al., *N Engl J Med.* 366:1275-1286, 2012.
Tomaras G D, et al., *J Virol.* 85:11502-11519, 2011.
Gottardo R, et al., *PLoS One.* 8:e75665, 2013.
Shen X, et al., *J Virol.* 89:8643-8650, 2015.
Donaldson M M, et al., *J Immunol Methods.* 386:10-21, 2012.
Foulds K E, et al., *Cytometry A.* 81:360-361, 2012.
Pollara J, et al., *Cytometry. A* 79:603-612, 2011.
Zolla-Pazner S, et al., *PLoS One.* 9:e87572, 2014.
Yates N L, et al., *Sci Transl Med.* 6:228ra239, 2014.
Garcia-Arriaza J, et al., *J Virol.* 89:8525-8539, 2015.
Lewis G K, et al., *Proc Natl Acad Sci USA.* 111:15614-15621, 2014.
Tomaras G D, et al., *Proc Natl Acad Sci USA.* 110:9019-9024, 2013.
Flynn B J, et al., *Proc Natl Acad Sci USA.* 108:7131-7136, 2011.
Wille-Reece U, et al., *J Exp Med.* 213:1249-1258, 2006.
Park H, et al., *J Immunol.* 190:4103-4115, 2103.

What is claimed is:

1. A polynucleotide encoding a fusion protein, wherein said fusion protein is an anti-Dendritic Cell (DC) receptor antibody-HIV antigen fusion protein comprising,
   (i) an anti-DC receptor heavy chain (HDCR)-HIV antigen (Ag) fusion protein comprising the formula: HDCR-Ag, wherein Ag is a polypeptide with at least 80% sequence identity to SEQ ID NO:1; and
   (ii) an anti-DC receptor light chain (LDCR).

2. The polynucleotide of claim 1, wherein the fusion protein further comprises one or more peptide linkers (PL).

3. The fusion protein of claim 1, wherein the fusion protein comprises:
   (i) HDCR-PL-Ag; and
   (ii) LDCR.

4. The polynucleotide of claim 1, wherein the fusion protein further comprises one or more joining sites (JS), wherein the joining site comprises alanine and serine residues.

5. The polynucleotide of claim 1, wherein the fusion protein further comprises one or more joining sites (JS), wherein the joining site consists of alanine and serine residues.

6. The polynucleotide of claim 1, wherein the fusion protein comprises:
   (i) HDCR-JS-PL-JS-Ag-JS; and
   (ii) LCD40;
   wherein JS is a joining site and PL is a peptide linker, and LCD40 is an anti-CD40 light chain.

7. The polynucleotide of claim 2, wherein the peptide linker comprises a polypeptide with at least 80% sequence identity to SEQ ID NO:2.

8. The polynucleotide of claim 3, wherein PL-Ag comprises a polypeptide with at least 80% identity to SEQ ID NO:3.

9. The polynucleotide of claim 3, wherein the fusion protein is an anti-CD40 antibody-HIV antigen fusion protein comprising
   (i) an anti-CD40 heavy chain (HCD40)-HIV antigen (Ag) fusion protein comprising the formula: HCD40-Ag, wherein Ag is a polypeptide with at least 80% sequence identity to SEQ ID NO:1; and
   (ii) an anti-CD40 light chain (LCD40).

10. The polynucleotide of claim 9, wherein the anti-CD40 antibody is a human or humanized anti-CD40 antibody.

11. The polynucleotide of claim 9, wherein the anti-CD40 antibody comprises human IgG4 heavy chain constant region.

12. The polynucleotide of claim 11, wherein the human IgG4 heavy chain constant region comprises one or both of S241P and L248E substitutions.

13. The polynucleotide of claim 9, wherein the HCD40 comprises a polypeptide with at least 80% sequence identity to SEQ ID NO:4.

14. The polynucleotide of claim 9, wherein the LCD40 comprises a polypeptide with at least 80% sequence identity to SEQ ID NO:5.

15. The polynucleotide of claim 9, wherein HCDR comprises the complementarity determining regions CDR1H, CDR2H and CDR3H, the CDR1H having the amino acid sequence GFTFSDYYMY (SEQ ID NO:10), the CDR2H having the amino acid sequence YINSGGGSTYYPDTVKG (SEQ ID NO.:11), and the CDR3H having the amino acid sequence RGLPFHAMDY (SEQ ID NO.:12).

16. The polynucleotide of claim 9, wherein LCD40 comprises the complementarity determining regions CDR1L, CDR2L and CDR3L, the CDR1L having the amino acid sequence SASQGISNYLN (SEQ ID NO.:13) the CDR2L having the amino acid sequence YTSILHS (SEQ ID NO.: 14) and the CDR3L having the amino acid sequence QQFNKLPPT (SEQ ID NO.:15).

17. The polynucleotide of claim 9, comprising
    (i) a HCD40-Ag fusion protein comprising an amino acid sequence with at least 80% sequence identity to SEQ ID NO:6; and
    (ii) a LCD40 comprising an amino acid sequence with at least 80% identity to SEQ ID NO:5.

18. The polynucleotide of claim 9, wherein HCDR comprises the complementarity determining regions CDR1H, CDR2H and CDR3H, the CDR1H having the amino acid sequence GYSFTGYYMH (SEQ ID NO.:18), the CDR2H having the amino acid sequence RINPYNGATSYNQNFKD (SEQ ID NO.:19), and the CDR3H having the amino acid sequence EDYVY (SEQ ID NO.:20).

19. The polynucleotide of claim 9, wherein LCD40 comprises the complementarity determining regions CDR1L, CDR2L and CDR3L, the CDR1L having the amino acid sequence RSSQSLVHSNGNTYLH (SEQ ID NO.:21) the CDR2L having the amino acid sequence KVSNRFS (SEQ ID NO.:22) and the CDR3L having the amino acid sequence SQSTHVPWT (SEQ ID NO.:23).

20. The polynucleotide of claim 9, wherein HCDR comprises the complementarity determining regions CDR1H, CDR2H and CDR3H, the CDR1H having the amino acid sequence GYTFTDYVLH (SEQ ID NO.:26), the CDR2H having the amino acid sequence YINPYNDGTKYNEKFKG (SEQ ID NO.:27), and the CDR3H having the amino acid sequence GYPAYSGYAMDY (SEQ ID NO.:28).

21. The polynucleotide of claim 9, wherein LCD40 comprises the complementarity determining regions CDR1L, CDR2L and CDR3L, the CDR1L having the amino acid sequence RASQDISNYLN (SEQ ID NO.:29) the CDR2L having the amino acid sequence YTSRLHS (SEQ ID NO.:30) and the CDR3L having the amino acid sequence HHGNTLPWT (SEQ ID NO.:31).

22. A polynucleotide comprising a nucleotide sequence that is at least 80% identical to SEQ ID NO: 7.

23. A polynucleotide comprising a nucleotide sequence that is at least 80% identical to SEQ ID NO: 8.

24. An expression vector comprising the polynucleotides of claim 22, and wherein the the expression vector further comprises a polynucleotide comprising a nucleotide sequence that is at least 80% identical to SEQ ID NO: 8.

25. An expression vector comprising the polynucleotide of claim 1.

26. A host cell comprising the polynucleotide of claim 1.

27. The host cell of claim 26, wherein the host cell is a mammalian cell.

28. The host cell of claim 27, wherein the mammalian cell is a CHO cell.

29. A fusion protein produced from the host cell of claim 26.

* * * * *

UNITED STATES PATENT AND TRADEMARK OFFICE
CERTIFICATE OF CORRECTION

PATENT NO. : 10,722,572 B2
APPLICATION NO. : 16/708787
DATED : July 28, 2020
INVENTOR(S) : Levy et al.

Page 1 of 1

It is certified that error appears in the above-identified patent and that said Letters Patent is hereby corrected as shown below:

In the Claims

In Claim 24, Column 127, Line 2, please delete "the the" and insert --the-- therefore.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 32

<210> SEQ ID NO 1
<211> LENGTH: 657
<212> TYPE: PRT
<213> ORGANISM: Human immunodeficiency virus 1

<400> SEQUENCE: 1

```
Asn Leu Trp Val Thr Val Tyr Tyr Gly Val Pro Val Trp Lys Glu Ala
1               5                   10                  15

Lys Thr Thr Leu Phe Cys Ala Ser Asp Ala Lys Ser Tyr Glu Lys Glu
            20                  25                  30

Val His Asn Val Trp Ala Thr His Ala Cys Val Pro Thr Asp Pro Asn
        35                  40                  45

Pro Gln Glu Ile Val Leu Gly Asn Val Thr Glu Asn Phe Asn Met Trp
    50                  55                  60

Lys Asn Asp Met Val Asp Gln Met His Glu Asp Ile Ile Ser Leu Trp
65                  70                  75                  80

Asp Gln Ser Leu Lys Pro Cys Val Lys Leu Thr Pro Leu Cys Val Thr
                85                  90                  95

Leu Asn Cys Thr Glu Val Asn Val Thr Arg Asn Val Asn Asn Ser Val
            100                 105                 110

Val Asn Asn Thr Thr Asn Val Asn Asn Ser Met Asn Gly Asp Met Lys
        115                 120                 125

Asn Cys Ser Phe Asn Ile Thr Thr Glu Leu Lys Asp Lys Lys Lys Asn
    130                 135                 140

Val Tyr Ala Leu Phe Tyr Lys Leu Asp Ile Val Ser Leu Asn Glu Thr
145                 150                 155                 160

Asp Asp Ser Glu Thr Gly Asn Ser Ser Lys Tyr Tyr Arg Leu Ile Asn
                165                 170                 175

Cys Asn Thr Ser Ala Leu Thr Gln Ala Cys Pro Lys Val Ser Phe Asp
            180                 185                 190

Pro Ile Pro Ile His Tyr Cys Ala Pro Ala Gly Tyr Ala Ile Leu Lys
        195                 200                 205

Cys Asn Asn Lys Thr Phe Asn Gly Thr Gly Pro Cys His Asn Val Ser
    210                 215                 220
```

```
Thr Val Gln Cys Thr His Gly Ile Lys Pro Val Ser Thr Gln Leu
225                 230                 235                 240

Leu Leu Asn Gly Ser Leu Ala Glu Glu Gly Ile Ile Ile Arg Ser Glu
            245                 250                 255

Asn Leu Thr Asn Asn Val Lys Thr Ile Ile Val His Leu Asn Arg Ser
                260                 265                 270

Ile Glu Ile Val Cys Val Arg Pro Asn Asn Asn Thr Arg Gln Ser Ile
            275                 280                 285

Arg Ile Gly Pro Gly Gln Thr Phe Tyr Ala Thr Gly Asp Ile Ile Gly
            290                 295                 300

Asp Ile Arg Gln Ala His Cys Asn Ile Ser Arg Thr Asn Trp Thr Lys
305                 310                 315                 320

Thr Leu Arg Glu Val Arg Asn Lys Leu Arg Glu His Phe Pro Asn Lys
                325                 330                 335

Asn Ile Thr Phe Lys Pro Ser Ser Gly Gly Asp Leu Glu Ile Thr Thr
            340                 345                 350

His Ser Phe Asn Cys Arg Gly Glu Phe Phe Tyr Cys Asn Thr Ser Gly
            355                 360                 365

Leu Phe Ser Ile Asn Tyr Thr Glu Asn Asn Thr Asp Gly Thr Pro Ile
370                 375                 380

Thr Leu Pro Cys Arg Ile Arg Gln Ile Ile Asn Met Trp Gln Glu Val
385                 390                 395                 400

Gly Arg Ala Met Tyr Ala Pro Pro Ile Glu Gly Asn Ile Ala Cys Lys
                405                 410                 415

Ser Asp Ile Thr Gly Leu Leu Leu Val Arg Asp Gly Gly Ser Thr Asn
            420                 425                 430

Asp Ser Thr Asn Asn Asn Thr Glu Ile Phe Arg Pro Ala Gly Gly Asp
            435                 440                 445

Met Arg Asp Asn Trp Arg Ser Glu Leu Tyr Lys Tyr Lys Val Val Glu
450                 455                 460

Ile Lys Pro Leu Gly Ile Ala Pro Thr Glu Ala Lys Arg Arg Val Val
465                 470                 475                 480

Glu Arg Glu Lys Arg Ala Val Gly Ile Gly Ala Val Phe Leu Gly Phe
                485                 490                 495

Leu Gly Ala Ala Gly Ser Thr Met Gly Ala Ala Ser Ile Thr Leu Thr
            500                 505                 510

Ala Gln Ala Arg Gln Val Leu Ser Gly Ile Val Gln Gln Gln Ser Asn
            515                 520                 525

Leu Leu Arg Ala Ile Glu Ala Gln Gln His Leu Leu Gln Leu Thr Val
            530                 535                 540

Trp Gly Ile Lys Gln Leu Gln Thr Arg Val Leu Ala Ile Glu Arg Tyr
545                 550                 555                 560

Leu Lys Asp Gln Gln Leu Leu Gly Leu Trp Gly Cys Ser Gly Lys Leu
                565                 570                 575

Ile Cys Thr Thr Ala Val Pro Trp Asn Ile Ser Trp Ser Asn Lys Ser
            580                 585                 590

Lys Thr Asp Ile Trp Asp Asn Met Thr Trp Met Gln Trp Asp Arg Glu
            595                 600                 605

Ile Ser Asn Tyr Thr Asn Thr Ile Tyr Arg Leu Leu Glu Asp Ser Gln
            610                 615                 620

Ser Gln Gln Glu Gln Asn Glu Lys Asp Leu Leu Ala Leu Asp Ser Trp
625                 630                 635                 640
```

```
Asn Asn Leu Trp Asn Trp Phe Asp Ile Thr Lys Trp Leu Trp Tyr Ile
                645                 650                 655

Lys

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Thr Pro Thr Asn Thr Ile Ser Val Thr Pro Thr Asn Asn Ser Thr
1               5                   10                  15

Pro Thr Asn Asn Ser Asn Pro Lys Pro Asn Pro
            20                  25

<210> SEQ ID NO 3
<211> LENGTH: 690
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Ser Gln Thr Pro Thr Asn Thr Ile Ser Val Thr Pro Thr Asn Asn
1               5                   10                  15

Ser Thr Pro Thr Asn Asn Ser Asn Pro Lys Pro Asn Pro Ala Ser Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ser Tyr Glu Lys Glu Val
    50                  55                  60

His Asn Val Trp Ala Thr His Ala Cys Val Pro Thr Asp Pro Asn Pro
65                  70                  75                  80

Gln Glu Ile Val Leu Gly Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Glu Val Asn Val Thr Arg Asn Val Asn Asn Ser Val Val
    130                 135                 140

Asn Asn Thr Thr Asn Val Asn Asn Ser Met Asn Gly Asp Met Lys Asn
145                 150                 155                 160

Cys Ser Phe Asn Ile Thr Thr Glu Leu Lys Asp Lys Lys Lys Asn Val
                165                 170                 175

Tyr Ala Leu Phe Tyr Lys Leu Asp Ile Val Ser Leu Asn Glu Thr Asp
            180                 185                 190

Asp Ser Glu Thr Gly Asn Ser Ser Lys Tyr Tyr Arg Leu Ile Asn Cys
        195                 200                 205

Asn Thr Ser Ala Leu Thr Gln Ala Cys Pro Lys Val Ser Phe Asp Pro
    210                 215                 220

Ile Pro Ile His Tyr Cys Ala Pro Ala Gly Tyr Ala Ile Leu Lys Cys
225                 230                 235                 240

Asn Asn Lys Thr Phe Asn Gly Thr Gly Pro Cys His Asn Val Ser Thr
```

-continued

```
                245                 250                 255
Val Gln Cys Thr His Gly Ile Lys Pro Val Val Ser Thr Gln Leu Leu
                260                 265                 270
Leu Asn Gly Ser Leu Ala Glu Glu Gly Ile Ile Ile Arg Ser Glu Asn
                275                 280                 285
Leu Thr Asn Asn Val Lys Thr Ile Ile Val His Leu Asn Arg Ser Ile
                290                 295                 300
Glu Ile Val Cys Val Arg Pro Asn Asn Asn Thr Arg Gln Ser Ile Arg
305                 310                 315                 320
Ile Gly Pro Gly Gln Thr Phe Tyr Ala Thr Gly Asp Ile Ile Gly Asp
                325                 330                 335
Ile Arg Gln Ala His Cys Asn Ile Ser Arg Thr Asn Trp Thr Lys Thr
                340                 345                 350
Leu Arg Glu Val Arg Asn Lys Leu Arg Glu His Phe Pro Asn Lys Asn
                355                 360                 365
Ile Thr Phe Lys Pro Ser Ser Gly Gly Asp Leu Glu Ile Thr Thr His
                370                 375                 380
Ser Phe Asn Cys Arg Gly Glu Phe Phe Tyr Cys Asn Thr Ser Gly Leu
385                 390                 395                 400
Phe Ser Ile Asn Tyr Thr Glu Asn Asn Thr Asp Gly Thr Pro Ile Thr
                405                 410                 415
Leu Pro Cys Arg Ile Arg Gln Ile Ile Asn Met Trp Gln Glu Val Gly
                420                 425                 430
Arg Ala Met Tyr Ala Pro Pro Ile Glu Gly Asn Ile Ala Cys Lys Ser
                435                 440                 445
Asp Ile Thr Gly Leu Leu Leu Val Arg Asp Gly Gly Ser Thr Asn Asp
                450                 455                 460
Ser Thr Asn Asn Thr Glu Ile Phe Arg Pro Ala Gly Gly Asp Met
465                 470                 475                 480
Arg Asp Asn Trp Arg Ser Glu Leu Tyr Lys Tyr Lys Val Val Glu Ile
                485                 490                 495
Lys Pro Leu Gly Ile Ala Pro Thr Glu Ala Lys Arg Arg Val Val Glu
                500                 505                 510
Arg Glu Lys Arg Ala Val Gly Ile Gly Ala Val Phe Leu Gly Phe Leu
                515                 520                 525
Gly Ala Ala Gly Ser Thr Met Gly Ala Ala Ser Ile Thr Leu Thr Ala
                530                 535                 540
Gln Ala Arg Gln Val Leu Ser Gly Ile Val Gln Gln Ser Asn Leu
545                 550                 555                 560
Leu Arg Ala Ile Glu Ala Gln Gln His Leu Leu Gln Leu Thr Val Trp
                565                 570                 575
Gly Ile Lys Gln Leu Gln Thr Arg Val Leu Ala Ile Glu Arg Tyr Leu
                580                 585                 590
Lys Asp Gln Gln Leu Leu Gly Leu Trp Gly Cys Ser Gly Lys Leu Ile
                595                 600                 605
Cys Thr Thr Ala Val Pro Trp Asn Ile Ser Trp Ser Asn Lys Ser Lys
                610                 615                 620
Thr Asp Ile Trp Asp Asn Met Thr Trp Met Gln Trp Asp Arg Glu Ile
625                 630                 635                 640
Ser Asn Tyr Thr Asn Thr Ile Tyr Arg Leu Leu Glu Asp Ser Gln Ser
                645                 650                 655
Gln Gln Glu Gln Asn Glu Lys Asp Leu Leu Ala Leu Asp Ser Trp Asn
                660                 665                 670
```

```
Asn Leu Trp Asn Trp Phe Asp Ile Thr Lys Trp Leu Trp Tyr Ile Lys
        675                 680                 685

Ala Ser
    690

<210> SEQ ID NO 4
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Pro Phe His Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
```

```
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
            435                 440                 445

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15
Asp Arg Val Thr Ile Thr Cys Ser Ala Ser Gln Gly Ile Ser Asn Tyr
            20                  25                  30
Leu Asn Trp Tyr Gln Gln Lys Pro Gly Lys Ala Val Lys Leu Leu Ile
        35                  40                  45
Tyr Tyr Thr Ser Ile Leu His Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Phe Asn Lys Leu Pro Pro
                85                  90                  95
Thr Phe Gly Gly Gly Thr Lys Leu Glu Ile Lys Gly Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 6
<211> LENGTH: 1136
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Pro Phe His Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Ser Leu Gly Lys Ala Ser
            435                 440                 445

Gln Thr Pro Thr Asn Thr Ile Ser Val Thr Pro Thr Asn Asn Ser Thr
        450                 455                 460

Pro Thr Asn Asn Ser Asn Pro Lys Pro Asn Pro Ala Ser Asn Leu Trp
465                 470                 475                 480

Val Thr Val Tyr Tyr Gly Val Pro Val Trp Lys Glu Ala Lys Thr Thr
            485                 490                 495

Leu Phe Cys Ala Ser Asp Ala Lys Val Tyr Glu Lys Glu Val His Asn
        500                 505                 510

Val Trp Ala Thr His Ala Cys Val Pro Thr Asp Pro Asn Pro Gln Glu
            515                 520                 525

Ile Val Leu Gly Asn Val Thr Glu Asn Phe Asn Met Trp Lys Asn Asp
530                 535                 540

Met Val Asp Gln Met His Glu Asp Ile Ile Ser Leu Trp Asp Gln Ser
545                 550                 555                 560

Leu Lys Pro Cys Val Lys Leu Thr Pro Leu Cys Val Thr Leu Asn Cys
            565                 570                 575

Thr Glu Val Asn Val Thr Arg Asn Val Asn Asn Ser Val Val Asn Asn
        580                 585                 590

Thr Thr Asn Val Asn Asn Ser Met Asn Gly Asp Met Lys Asn Cys Ser
        595                 600                 605

Phe Asn Ile Thr Thr Glu Leu Lys Asp Lys Lys Lys Asn Val Tyr Ala
        610                 615                 620

Leu Phe Tyr Lys Leu Asp Ile Val Ser Leu Asn Glu Thr Asp Asp Ser
625                 630                 635                 640

Glu Thr Gly Asn Ser Ser Lys Tyr Tyr Arg Leu Ile Asn Cys Asn Thr
            645                 650                 655

Ser Ala Leu Thr Gln Ala Cys Pro Lys Val Ser Phe Asp Pro Ile Pro
        660                 665                 670

Ile His Tyr Cys Ala Pro Ala Gly Tyr Ala Ile Leu Lys Cys Asn Asn
    675                 680                 685

Lys Thr Phe Asn Gly Thr Gly Pro Cys His Asn Val Ser Thr Val Gln
        690                 695                 700

Cys Thr His Gly Ile Lys Pro Val Val Ser Thr Gln Leu Leu Leu Asn
705                 710                 715                 720

Gly Ser Leu Ala Glu Glu Gly Ile Ile Ile Arg Ser Glu Asn Leu Thr
            725                 730                 735

Asn Asn Val Lys Thr Ile Ile Val His Leu Asn Arg Ser Ile Glu Ile
        740                 745                 750

Val Cys Val Arg Pro Asn Asn Asn Thr Arg Gln Ser Ile Arg Ile Gly
        755                 760                 765

Pro Gly Gln Thr Phe Tyr Ala Thr Gly Asp Ile Ile Gly Asp Ile Arg
        770                 775                 780

Gln Ala His Cys Asn Ile Ser Arg Thr Asn Trp Thr Lys Thr Leu Arg
785                 790                 795                 800
```

```
Glu Val Arg Asn Lys Leu Arg Glu His Phe Pro Asn Lys Asn Ile Thr
            805                 810                 815

Phe Lys Pro Ser Ser Gly Gly Asp Leu Glu Ile Thr Thr His Ser Phe
        820                 825                 830

Asn Cys Arg Gly Glu Phe Phe Tyr Cys Asn Thr Ser Gly Leu Phe Ser
        835                 840                 845

Ile Asn Tyr Thr Glu Asn Asn Thr Asp Gly Thr Pro Ile Thr Leu Pro
850                 855                 860

Cys Arg Ile Arg Gln Ile Ile Asn Met Trp Gln Glu Val Gly Arg Ala
865                 870                 875                 880

Met Tyr Ala Pro Pro Ile Glu Gly Asn Ile Ala Cys Lys Ser Asp Ile
                885                 890                 895

Thr Gly Leu Leu Leu Val Arg Asp Gly Gly Ser Thr Asn Asp Ser Thr
            900                 905                 910

Asn Asn Asn Thr Glu Ile Phe Arg Pro Ala Gly Gly Asp Met Arg Asp
        915                 920                 925

Asn Trp Arg Ser Glu Leu Tyr Lys Tyr Lys Val Val Glu Ile Lys Pro
    930                 935                 940

Leu Gly Ile Ala Pro Thr Glu Ala Lys Arg Arg Val Val Glu Arg Glu
945                 950                 955                 960

Lys Arg Ala Val Gly Ile Gly Ala Val Phe Leu Gly Phe Leu Gly Ala
                965                 970                 975

Ala Gly Ser Thr Met Gly Ala Ala Ser Ile Thr Leu Thr Ala Gln Ala
            980                 985                 990

Arg Gln Val Leu Ser Gly Ile Val  Gln Gln Gln Ser Asn  Leu Leu Arg
        995                 1000                1005

Ala Ile  Glu Ala Gln Gln His  Leu Leu Gln Leu Thr  Val Trp Gly
        1010                1015                1020

Ile Lys  Gln Leu Gln Thr Arg  Val Leu Ala Ile Glu  Arg Tyr Leu
        1025                1030                1035

Lys Asp  Gln Gln Leu Leu Gly  Leu Trp Gly Cys Ser  Gly Lys Leu
        1040                1045                1050

Ile Cys  Thr Thr Ala Val Pro  Trp Asn Ile Ser Trp  Ser Asn Lys
        1055                1060                1065

Ser Lys  Thr Asp Ile Trp Asp  Asn Met Thr Trp Met  Gln Trp Asp
        1070                1075                1080

Arg Glu  Ile Ser Asn Tyr Thr  Asn Thr Ile Tyr Arg  Leu Leu Glu
        1085                1090                1095

Asp Ser  Gln Ser Gln Gln Glu  Gln Asn Glu Lys Asp  Leu Leu Ala
        1100                1105                1110

Leu Asp  Ser Trp Asn Asn Leu  Trp Asn Trp Phe Asp  Ile Thr Lys
        1115                1120                1125

Trp Leu  Trp Tyr Ile Lys Ala  Ser
        1130                1135

<210> SEQ ID NO 7
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgagggtcc ccgctcagct cctggggctc ctgctgctct ggctcccagg cgcgcgatgt    60
```

```
gatatccaga tgacacagag cccttcctcc ctgtctgcct ctgtgggaga cagagtcacc    120
atcacctgca gtgcaagtca gggcattagc aattatttaa actggtatca gcagaaacca    180
ggcaaggccg ttaaactcct gatctattac acatcaattt tacactcagg agtcccatca    240
aggttcagtg gcagtgggtc tgggacagat tataccctca ccatcagctc cctgcagcct    300
gaagatttcg ccacttacta ttgtcagcag tttaataagc ttcctccgac gttcggtgga    360
ggcaccaagc tggagatcaa ggaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag               705

<210> SEQ ID NO 8
<211> LENGTH: 3468
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgggttgga gcctcatctt gctcttcctt gtcgctgttg ctacgcgtgt ccactccgaa    60
gtgcagctgg tggagtctgg gggaggctta gtgcagcccg agggtccct gaaactctcc    120 tgtgcaacct ctggattcac tttcagtgac tattatatgt attgggttcg ccaggcccca    180
ggcaagggcc tggagtgggt cgcatacatt aattctggtg gtggtagcac ctattatcca    240
gacactgtaa agggccgatt caccatctcc agagacaatg ccaagaacac cctgtacctg    300
caaatgaaca gcctgagggc cgaggacaca gccgtgtatt actgtgcaag acggggggtta    360 ccgttccatg ctatggacta ttggggtcaa ggaaccctgg tcaccgtctc ctcagcttcc    420
accaagggcc catccgtctt ccccctggcg ccctgctcca ggagcacctc cgagagcaca    480
gccgccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcacgaa gacctacacc    660 tgcaatgtag atcacaagcc cagcaacacc aaggtggaca gagagttga gtccaaatat    720 ggtcccccat gcccaccatg cccagcacct gagttcgagg ggggaccatc agtcttcctg    780 ttcccccaa acccaagga cactctcatg atctcccgga cccctgaggt cacgtgcgtg    840
gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag    1020
gtctccaaca aaggcctccc gtcctccatc gagaaaacca tctccaaagc caaagggcag    1080
ccccgagagc cacaggtgta caccctgccc ccatcccagg aggagatgac caagaaccag    1140
gtcagcctga cctgcctggt caaaggcttc taccccagcg acatcgccgt ggagtgggag    1200
agcaatgggc agccggagaa caactacaag accacgcctc ccgtgctgga ctccgacggc    1260
tccttcttcc tctacagcag gctaaccgtg gacaagagca ggtggcagga ggggaatgtc    1320
ttctcatgct ccgtgatgca tgaggctctg cacaaccact acacacagaa gagcctctcc    1380
```

| | |
|---|---|
| ctgtctctgg gtaaagctag ccagacccccg accaacacca tttccgtgac ccccaccaac | 1440 |
| aatagcactc cgacgaacaa cagcaacccc aagcccaacc cggcatcaaa cctctgggtg | 1500 |
| accgtgtact atggcgtccc tgtgtggaaa gaagccaaga ccaccctgtt ctgcgcgtcc | 1560 |
| gacgccaagg tctacgaaaa ggaggtgcac aatgtctggg ccactcacgc ctgcgtcccc | 1620 |
| actgacccaa acccacaaga aatcgtgctg gggaacgtga ccgagaactt caatatgtgg | 1680 |
| aagaacgaca tggtggacca gatgcatgag gatatcatca gcctgtggga ccagtcgctc | 1740 |
| aagccttgcg tcaagctgac tcctctgtgt gtgaccttga actgtactga agtgaacgtg | 1800 |
| accaggaacg tcaacaacag cgtggtcaac aacactacca acgtgaacaa ctccatgaac | 1860 |
| ggagacatga agaattgctc cttcaacatc accaccgaac tcaaggacaa gaagaagaat | 1920 |
| gtgtacgccc tgttctacaa gttggacatc gtgtccctca acgaaactga cgattccgaa | 1980 |
| accgggaact cgtccaagta ttaccggctc atcaactgca acacctccgc cctgactcag | 2040 |
| gcttgtccga aagtgtcctt cgacccaatt ccgatccatt actgcgcccc cgccggttac | 2100 |
| gccattctga gtgcaacaa taagaccttc aacggaacag gccctgcca caacgtgtcg | 2160 |
| accgtgcagt gcacacacgg tatcaaaccc gtcgtgtcca cccaactcct gctgaacggc | 2220 |
| tcactggctg aggagggtat tatcatccgg tccgagaacc tgactaacaa cgtgaaaacc | 2280 |
| attatcgtgc acctgaaccg atcgatcgaa atcgtctgcg tgcgccctaa caacaatact | 2340 |
| cggcagtcca tccggatcgg gcctggacag actttctacg cgaccggaga tatcattgga | 2400 |
| gatatcagac aggcgcactg taacatctcc cgcaccaact ggaccaagac cctgagagaa | 2460 |
| gtcaggaaca agctccggga gcacttcccc aacaagaaca tcacctttaa gccgtcctcc | 2520 |
| ggcggcgacc tggagattac cactcattcg ttcaactgcc gcggggaatt cttctactgt | 2580 |
| aataccctccg gactgttttc catcaactac actgaaaaca caccgatgg cacccccgatt | 2640 |
| acccttccgt gccggattag gcagatcatt aatatgtggc aggaggtcgg acgggctatg | 2700 |
| tacgccccgc cgattgaggg aaatatcgcc tgcaaatccg acattactgg cctgctgctc | 2760 |
| gtgcgcgacg gaggctcgac caacgacagc accaacaaca cactgagat cttccggccc | 2820 |
| gccggcggag atatgagaga taactggagg tccgaacttt acaagtacaa ggtcgtggaa | 2880 |
| atcaagccgc ttggtattgc acctaccgag gccaagagaa gagtggtgga gcgggagaag | 2940 |
| cgggcagtgg ggatcggagc cgtgttcctg ggattcctgg gcgcggcggg ctcgaccatg | 3000 |
| ggagcggcct ctattaccct gacggctcag gcccgccaag tgctgagcgg aatcgtgcag | 3060 |
| cagcaatcga atctgctgcg ggccatcgaa gcccagcagc acctcttgca acttactgtg | 3120 |
| tggggtatca agcagcttca aactcgcgtg ttggccatag aacgctacct gaaggaccag | 3180 |
| cagttgctcg gactctgggg atgcagcggg aagctgattt gcactactgc cgtgccgtgg | 3240 |
| aacatctcct ggtcaaacaa gagcaaaacc gacatttggg acaacatgac gtggatgcag | 3300 |
| tgggatcggg agatctcaaa ctacactaac accatctacc gcctgctgga ggactcccag | 3360 |
| tcacaacagg aacagaacga aaaggatctg ctggcactgg actcatgaa caacctgtgg | 3420 |
| aactgggttg acatcaccaa gtggctgtgg tacatcaagg cgtcttga | 3468 |

<210> SEQ ID NO 9
<211> LENGTH: 1155
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 9

Met Gly Trp Ser Leu Ile Leu Leu Phe Leu Val Ala Val Ala Thr Arg
1               5                   10                  15

Val His Ser Glu Val Gln Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Tyr Met Tyr Trp Val Arg Gln Ala Pro Gly Lys Gly Leu
    50                  55                  60

Glu Trp Val Ala Tyr Ile Asn Ser Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Asn Ser Leu Arg Ala Glu Asp Thr Ala Val
                100                 105                 110

Tyr Tyr Cys Ala Arg Arg Gly Leu Pro Phe His Ala Met Asp Tyr Trp
            115                 120                 125

Gly Gln Gly Thr Leu Val Thr Val Ser Ser Ala Ser Thr Lys Gly Pro
        130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Lys Thr Tyr Thr Cys Asn Val Asp
        210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser Gln Glu Asp
            275                 280                 285

Pro Glu Val Gln Phe Asn Trp Tyr Val Asp Gly Val Glu Val His Asn
        290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415
```

```
Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
        450                 455                 460

Lys Ala Ser Gln Thr Pro Thr Asn Thr Ile Ser Val Thr Pro Thr Asn
465                 470                 475                 480

Asn Ser Thr Pro Thr Asn Asn Ser Asn Pro Lys Pro Asn Pro Ala Ser
                485                 490                 495

Asn Leu Trp Val Thr Val Tyr Tyr Gly Val Pro Val Trp Lys Glu Ala
                500                 505                 510

Lys Thr Thr Leu Phe Cys Ala Ser Asp Ala Lys Val Tyr Glu Lys Glu
            515                 520                 525

Val His Asn Val Trp Ala Thr His Ala Cys Val Pro Thr Asp Pro Asn
    530                 535                 540

Pro Gln Glu Ile Val Leu Gly Asn Val Thr Glu Asn Phe Asn Met Trp
545                 550                 555                 560

Lys Asn Asp Met Val Asp Gln Met His Glu Asp Ile Ile Ser Leu Trp
                565                 570                 575

Asp Gln Ser Leu Lys Pro Cys Val Lys Leu Thr Pro Leu Cys Val Thr
            580                 585                 590

Leu Asn Cys Thr Glu Val Asn Val Thr Arg Asn Val Asn Asn Ser Val
        595                 600                 605

Val Asn Asn Thr Thr Asn Val Asn Asn Ser Met Asn Gly Asp Met Lys
    610                 615                 620

Asn Cys Ser Phe Asn Ile Thr Thr Glu Leu Lys Asp Lys Lys Asn
625                 630                 635                 640

Val Tyr Ala Leu Phe Tyr Lys Leu Asp Ile Val Ser Leu Asn Glu Thr
                645                 650                 655

Asp Asp Ser Glu Thr Gly Asn Ser Ser Lys Tyr Tyr Arg Leu Ile Asn
            660                 665                 670

Cys Asn Thr Ser Ala Leu Thr Gln Ala Cys Pro Lys Val Ser Phe Asp
        675                 680                 685

Pro Ile Pro Ile His Tyr Cys Ala Pro Ala Gly Tyr Ala Ile Leu Lys
    690                 695                 700

Cys Asn Asn Lys Thr Phe Asn Gly Thr Gly Pro Cys His Asn Val Ser
705                 710                 715                 720

Thr Val Gln Cys Thr His Gly Ile Lys Pro Val Val Ser Thr Gln Leu
                725                 730                 735

Leu Leu Asn Gly Ser Leu Ala Glu Glu Gly Ile Ile Ile Arg Ser Glu
            740                 745                 750

Asn Leu Thr Asn Asn Val Lys Thr Ile Ile Val His Leu Asn Arg Ser
        755                 760                 765

Ile Glu Ile Val Cys Val Arg Pro Asn Asn Asn Thr Arg Gln Ser Ile
    770                 775                 780

Arg Ile Gly Pro Gly Gln Thr Phe Tyr Ala Thr Gly Asp Ile Ile Gly
785                 790                 795                 800

Asp Ile Arg Gln Ala His Cys Asn Ile Ser Arg Thr Asn Trp Thr Lys
                805                 810                 815

Thr Leu Arg Glu Val Arg Asn Lys Leu Arg Glu His Phe Pro Asn Lys
            820                 825                 830
```

Asn Ile Thr Phe Lys Pro Ser Gly Gly Asp Leu Glu Ile Thr Thr
              835                 840                 845

His Ser Phe Asn Cys Arg Gly Glu Phe Phe Tyr Cys Asn Thr Ser Gly
    850                 855                 860

Leu Phe Ser Ile Asn Tyr Thr Glu Asn Asn Thr Asp Gly Thr Pro Ile
865                 870                 875                 880

Thr Leu Pro Cys Arg Ile Arg Gln Ile Ile Asn Met Trp Gln Glu Val
                885                 890                 895

Gly Arg Ala Met Tyr Ala Pro Pro Ile Glu Gly Asn Ile Ala Cys Lys
                900                 905                 910

Ser Asp Ile Thr Gly Leu Leu Leu Val Arg Asp Gly Gly Ser Thr Asn
                915                 920                 925

Asp Ser Thr Asn Asn Asn Thr Glu Ile Phe Arg Pro Ala Gly Gly Asp
    930                 935                 940

Met Arg Asp Asn Trp Arg Ser Glu Leu Tyr Lys Tyr Lys Val Val Glu
945                 950                 955                 960

Ile Lys Pro Leu Gly Ile Ala Pro Thr Glu Ala Lys Arg Arg Val Val
                965                 970                 975

Glu Arg Glu Lys Arg Ala Val Gly Ile Gly Ala Val Phe Leu Gly Phe
                980                 985                 990

Leu Gly Ala Ala Gly Ser Thr Met Gly Ala Ala Ser Ile Thr Leu Thr
    995                 1000                1005

Ala Gln Ala Arg Gln Val Leu Ser Gly Ile Val Gln Gln Gln Ser
    1010                1015                1020

Asn Leu Leu Arg Ala Ile Glu Ala Gln Gln His Leu Leu Gln Leu
    1025                1030                1035

Thr Val Trp Gly Ile Lys Gln Leu Gln Thr Arg Val Leu Ala Ile
    1040                1045                1050

Glu Arg Tyr Leu Lys Asp Gln Gln Leu Leu Gly Leu Trp Gly Cys
    1055                1060                1065

Ser Gly Lys Leu Ile Cys Thr Thr Ala Val Pro Trp Asn Ile Ser
    1070                1075                1080

Trp Ser Asn Lys Ser Lys Thr Asp Ile Trp Asp Asn Met Thr Trp
    1085                1090                1095

Met Gln Trp Asp Arg Glu Ile Ser Asn Tyr Thr Asn Thr Ile Tyr
    1100                1105                1110

Arg Leu Leu Glu Asp Ser Gln Ser Gln Gln Glu Gln Asn Glu Lys
    1115                1120                1125

Asp Leu Leu Ala Leu Asp Ser Trp Asn Asn Leu Trp Asn Trp Phe
    1130                1135                1140

Asp Ile Thr Lys Trp Leu Trp Tyr Ile Lys Ala Ser
    1145                1150                1155

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Thr Phe Ser Asp Tyr Tyr Met Tyr
1               5                   10

<210> SEQ ID NO 11

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ile Asn Ser Gly Gly Gly Ser Thr Tyr Tyr Pro Asp Thr Val Lys
1               5                   10                  15
Gly

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Gly Leu Pro Phe His Ala Met Asp Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Ala Ser Gln Gly Ile Ser Asn Tyr Leu Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Thr Ser Ile Leu His Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Phe Asn Lys Leu Pro Pro Thr
1               5

<210> SEQ ID NO 16
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 16

| | | | | | | | | | | | | | | | |
|---|---|---|---|---|---|---|---|---|---|---|---|---|---|---|---|
|Glu|Val|Gln|Leu|Gln|Gln|Ser|Gly|Pro|Glu|Leu|Val|Lys|Pro|Gly|Ala|
|1| | | |5| | | | |10| | | | |15| |
|Ser|Val|Lys|Ile|Ser|Cys|Lys|Ala|Ser|Gly|Tyr|Ser|Phe|Thr|Gly|Tyr|
| | | | |20| | | | |25| | | | |30| |
|Tyr|Met|His|Trp|Val|Lys|Gln|Ser|His|Val|Lys|Ser|Leu|Glu|Trp|Ile|
| | | |35| | | | |40| | | | |45| | |
|Gly|Arg|Ile|Asn|Pro|Tyr|Asn|Gly|Ala|Thr|Ser|Tyr|Asn|Gln|Asn|Phe|
| |50| | | | |55| | | | |60| | | | |
|Lys|Asp|Lys|Ala|Ser|Leu|Thr|Val|Asp|Lys|Ser|Ser|Ser|Thr|Ala|Tyr|
|65| | | | |70| | | | |75| | | | |80|
|Met|Glu|Leu|His|Ser|Leu|Thr|Ser|Glu|Asp|Ser|Ala|Val|Tyr|Tyr|Cys|
| | | | |85| | | | |90| | | | |95| |
|Ala|Arg|Glu|Asp|Tyr|Val|Tyr|Trp|Gly|Gln|Gly|Thr|Thr|Leu|Thr|Val|
| | | |100| | | | |105| | | | |110| | |
|Ser|Ser|Ala|Lys|Thr|Lys|Gly|Pro|Ser|Val|Phe|Pro|Leu|Ala|Pro|Cys|
| | | |115| | | | |120| | | | |125| | |
|Ser|Arg|Ser|Thr|Ser|Glu|Ser|Thr|Ala|Ala|Leu|Gly|Cys|Leu|Val|Lys|
| |130| | | | |135| | | | |140| | | | |
|Asp|Tyr|Phe|Pro|Glu|Pro|Val|Thr|Val|Ser|Trp|Asn|Ser|Gly|Ala|Leu|
|145| | | | |150| | | | |155| | | | |160|
|Thr|Ser|Gly|Val|His|Thr|Phe|Pro|Ala|Val|Leu|Gln|Ser|Ser|Gly|Leu|
| | | | |165| | | | |170| | | | |175| |
|Tyr|Ser|Leu|Ser|Ser|Val|Val|Thr|Val|Pro|Ser|Ser|Ser|Leu|Gly|Thr|
| | | |180| | | | |185| | | | |190| | |
|Lys|Thr|Tyr|Thr|Cys|Asn|Val|Asp|His|Lys|Pro|Ser|Asn|Thr|Lys|Val|
| | | |195| | | | |200| | | | |205| | |
|Asp|Lys|Arg|Val|Glu|Ser|Lys|Tyr|Gly|Pro|Pro|Cys|Pro|Pro|Cys|Pro|
| |210| | | | |215| | | | |220| | | | |
|Ala|Pro|Glu|Phe|Glu|Gly|Gly|Pro|Ser|Val|Phe|Leu|Phe|Pro|Pro|Lys|
|225| | | | |230| | | | |235| | | | |240|
|Pro|Lys|Asp|Thr|Leu|Met|Ile|Ser|Arg|Thr|Pro|Glu|Val|Thr|Cys|Val|
| | | | |245| | | | |250| | | | |255| |
|Val|Val|Asp|Val|Ser|Gln|Glu|Asp|Pro|Glu|Val|Gln|Phe|Asn|Trp|Tyr|
| | | |260| | | | |265| | | | |270| | |
|Val|Asp|Gly|Val|Glu|Val|His|Asn|Ala|Lys|Thr|Lys|Pro|Arg|Glu|Glu|
| | | |275| | | | |280| | | | |285| | |
|Gln|Phe|Asn|Ser|Thr|Tyr|Arg|Val|Val|Ser|Val|Leu|Thr|Val|Leu|His|
| |290| | | | |295| | | | |300| | | | |
|Gln|Asp|Trp|Leu|Asn|Gly|Lys|Glu|Tyr|Lys|Cys|Lys|Val|Ser|Asn|Lys|
|305| | | | |310| | | | |315| | | | |320|
|Gly|Leu|Pro|Ser|Ser|Ile|Glu|Lys|Thr|Ile|Ser|Lys|Ala|Lys|Gly|Gln|
| | | | |325| | | | |330| | | | |335| |
|Pro|Arg|Glu|Pro|Gln|Val|Tyr|Thr|Leu|Pro|Pro|Ser|Gln|Glu|Glu|Met|
| | | |340| | | | |345| | | | |350| | |
|Thr|Lys|Asn|Gln|Val|Ser|Leu|Thr|Cys|Leu|Val|Lys|Gly|Phe|Tyr|Pro|
| | | |355| | | | |360| | | | |365| | |
|Ser|Asp|Ile|Ala|Val|Glu|Trp|Glu|Ser|Asn|Gly|Gln|Pro|Glu|Asn|Asn|
| | | |370| | | | |375| | | | |380| | |
|Tyr|Lys|Thr|Thr|Pro|Pro|Val|Leu|Asp|Ser|Asp|Gly|Ser|Phe|Phe|Leu|
|385| | | | |390| | | | |395| | | | |400|
|Tyr|Ser|Arg|Leu|Thr|Val|Asp|Lys|Ser|Arg|Trp|Gln|Glu|Gly|Asn|Val|
| | | | |405| | | | |410| | | | |415| |

Phe Ser Cys Ser Val Met His Glu Ala Leu His Asn His Tyr Thr Gln
                420                 425                 430

Lys Ser Leu Ser Leu Ser Leu Gly Lys Ala Ser
        435                 440

<210> SEQ ID NO 17
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Ala Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Tyr Ser Phe Thr Gly Tyr Tyr Met His
1               5                   10

<210> SEQ ID NO 19
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 19

Arg Ile Asn Pro Tyr Asn Gly Ala Thr Ser Tyr Asn Gln Asn Phe Lys
1               5                   10                  15

Asp

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Asp Tyr Val Tyr
1               5

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ser Ser Gln Ser Leu Val His Ser Asn Gly Asn Thr Tyr Leu His
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Val Ser Asn Arg Phe Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gln Ser Thr His Val Pro Trp Thr
1               5

<210> SEQ ID NO 24
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Gln Gln Ser Gly Pro Glu Leu Val Lys Pro Gly Ala
```

-continued

```
1               5                   10                  15
Ser Val Lys Met Ser Cys Lys Ala Ser Gly Tyr Thr Phe Thr Asp Tyr
            20                  25                  30
Val Leu His Trp Val Lys Gln Lys Pro Gly Gln Gly Leu Glu Trp Ile
            35                  40                  45
Gly Tyr Ile Asn Pro Tyr Asn Asp Gly Thr Lys Tyr Asn Glu Lys Phe
            50                  55                  60
Lys Gly Lys Ala Thr Leu Thr Ser Asp Lys Ser Ser Thr Ala Tyr
65                  70                  75                  80
Met Glu Leu Ser Ser Leu Thr Ser Glu Asp Ser Ala Val Tyr Tyr Cys
            85                  90                  95
Ala Arg Gly Tyr Pro Ala Tyr Ser Gly Tyr Ala Met Asp Tyr Trp Gly
            100                 105                 110
Gln Gly Thr Ser Val Thr Val Ser Ser Ala Lys Thr Lys Gly Pro Ser
            115                 120                 125
Val Phe Pro Leu Ala Pro Cys Ser Arg Ser Thr Ser Glu Ser Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
            195                 200                 205
Lys Pro Ser Asn Thr Lys Val Asp Lys Arg Val Glu Ser Lys Tyr Gly
            210                 215                 220
Pro Pro Cys Pro Pro Cys Pro Ala Pro Glu Phe Glu Gly Gly Pro Ser
225                 230                 235                 240
Val Phe Leu Phe Pro Pro Lys Pro Lys Asp Thr Leu Met Ile Ser Arg
            245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
            275                 280                 285
Lys Thr Lys Pro Arg Glu Glu Gln Phe Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
            325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
            405                 410                 415
Arg Trp Gln Glu Gly Asn Val Phe Ser Cys Ser Val Met His Glu Ala
            420                 425                 430
```

```
Leu His Asn His Tyr Thr Gln Lys Ser Leu Ser Leu Ser Leu Gly Lys
        435                 440                 445

Ala Ser
    450

<210> SEQ ID NO 25
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys His His Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Tyr Thr Phe Thr Asp Tyr Val Leu His
1               5                   10

<210> SEQ ID NO 27
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 27

Tyr Ile Asn Pro Tyr Asn Asp Gly Thr Lys Tyr Asn Glu Lys Phe Lys
1               5                   10                  15
Gly

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Pro Ala Tyr Ser Gly Tyr Ala Met Asp Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala Ser Gln Asp Ile Ser Asn Tyr Leu Asn
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Thr Ser Arg Leu His Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

His His Gly Asn Thr Leu Pro Trp Thr
1               5

<210> SEQ ID NO 32
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      6xHis tag

<400> SEQUENCE: 32

His His His His His His
1               5
```